United States Patent
Choe et al.

(10) Patent No.: US 11,116,818 B2
(45) Date of Patent: Sep. 14, 2021

(54) COMPOSITIONS AND METHODS FOR INHIBITING VIRAL ENTRY

(71) Applicants: Children's Medical Center Corporation, Boston, MA (US); Dana-Farber Cancer Institute, Inc., Boston, MA (US)

(72) Inventors: Hyeryun Choe, Juno Beach, FL (US); Stephanie Jemielity, Waban, MA (US); Dale T. Umetsu, Newton, MA (US); Rosemarie H. De Kruyff, Newton, MA (US); Gordon J. Freeman, Brookline, MA (US)

(73) Assignee: Children's Medical Center Corporation Dana-Farber Cancer Institute, Boston, MA (US)

( * ) Notice: Subject to any disclaimer, the term of this patent is extended or adjusted under 35 U.S.C. 154(b) by 0 days.

(21) Appl. No.: 14/651,934

(22) PCT Filed: Dec. 12, 2013

(86) PCT No.: PCT/US2013/074678
§ 371 (c)(1),
(2) Date: Jun. 12, 2015

(87) PCT Pub. No.: WO2014/093627
PCT Pub. Date: Jun. 19, 2014

(65) Prior Publication Data
US 2015/0297677 A1 Oct. 22, 2015

Related U.S. Application Data

(60) Provisional application No. 61/737,070, filed on Dec. 13, 2012.

(51) Int. Cl.
*A61K 31/00* (2006.01)
*A61K 9/127* (2006.01)
(Continued)

(52) U.S. Cl.
CPC ........ *A61K 38/1774* (2013.01); *A61K 31/685* (2013.01); *A61K 31/713* (2013.01);
(Continued)

(58) Field of Classification Search
None
See application file for complete search history.

(56) References Cited

U.S. PATENT DOCUMENTS 4,666,893 A * 5/1987 Tsuchiya .............. A61K 31/685
514/78
2005/0276756 A1  12/2005 Hoo et al.
(Continued)

OTHER PUBLICATIONS

Rennert, PD. Novel roles for TIM-1 in immunity and infection. Immunol Lett. Dec. 30, 2011;141(1):28-35. (Year: 2011).*
(Continued)

*Primary Examiner* — Michelle S Horning
(74) *Attorney, Agent, or Firm* — Mintz Levin Cohn Ferris Glovsky and Popeo, P.C.; Peter F. Corless

(57) ABSTRACT

The invention provides methods, compositions, and kits featuring agents that inhibit viral entry mediated by T-cell Immunoglobulin and Mucin-domain containing proteins (TIM proteins) and other phosphatidylserine receptors.

7 Claims, 19 Drawing Sheets

Specification includes a Sequence Listing.

(51) Int. Cl.
- *A61K 39/00* (2006.01)
- *A61K 38/17* (2006.01)
- *A61K 31/685* (2006.01)
- *A61K 31/7105* (2006.01)
- *C12N 15/113* (2010.01)
- *A61K 31/713* (2006.01)
- *A61K 45/00* (2006.01)
- *C07K 14/705* (2006.01)
- *C07K 16/28* (2006.01)

(52) U.S. Cl.
CPC .......... *A61K 31/7105* (2013.01); *A61K 45/00* (2013.01); *C07K 14/70503* (2013.01); *C07K 16/2803* (2013.01); *C12N 15/113* (2013.01); *C12N 15/1138* (2013.01); *C07K 2317/76* (2013.01); *C07K 2319/30* (2013.01); *C12N 2310/11* (2013.01); *C12N 2310/14* (2013.01); *C12N 2310/17* (2013.01); *C12N 2310/531* (2013.01)

(56) References Cited

U.S. PATENT DOCUMENTS

| | | |
|---|---|---|
| 2010/0247521 A1 | 9/2010 | Jones et al. |
| 2012/0039978 A1 | 2/2012 | Moscona et al. |
| 2016/0017035 A1* | 1/2016 | Amara ............... C07K 16/2803 424/139.1 |

OTHER PUBLICATIONS

Meertens et al. The TIM and TAM families of phosphatidylserine receptors mediate dengue virus entry. Cell Host Microbe. Oct. 18, 2012;12(4):544-57. (Year: 2012).*

Kobayashi et al. TIM-1 and TIM-4 Glycoproteins Bind Phosphatidylserine and Mediate Uptake of Apoptotic Cells, Immunity, vol. 27, Issue 6, 2007,pp. 927-940 (Year: 2007).*

Rennert. Novel roles for TIM-1 in immunity and infection. Immunol Lett. Dec. 30, 2011;141(1):28-35. (Year: 2011).*

Jemielity et al. TIM-family proteins promote infection of multiple enveloped viruses through virion-associated phosphatidylserine. PLoS Pathog. Mar. 2013;9(3):e1003232. pp. 1-14. (Year: 2013).*

Richard et al. Virion-associated phosphatidylethanolamine promotes TIM1-mediated infection by Ebola, dengue, and West Nile viruses. Proc Natl Acad Sci U S A. Nov. 24, 2015;112(47):14682-7. doi: 10.1073/pnas.1508095112. (Year: 2015).*

Meertens, L., et al., "The TIM and TAM families of phosphatidylserine receptors mediate dengue virus entry", Oct. 18, 2012, Cell Host & Microbe, vol. 12, pp. 544-557.

Kondratowicz, A>S>, et al., "T-cell immunoglubulin and mucin domain 1 (TIM-1) is a receptor for Zaire Ebolavirus and Lake Victoria Marburgvirus", Proceedings of the National Academy of Sciences of the United States of America, May 17, 2011, vol. 108, No. 20, pp. 8426-8431.

International Search Report issued in corresponding International Application Serial No. PCT/US2013/074678, dated Sep. 24, 2014, 4 pages.

* cited by examiner

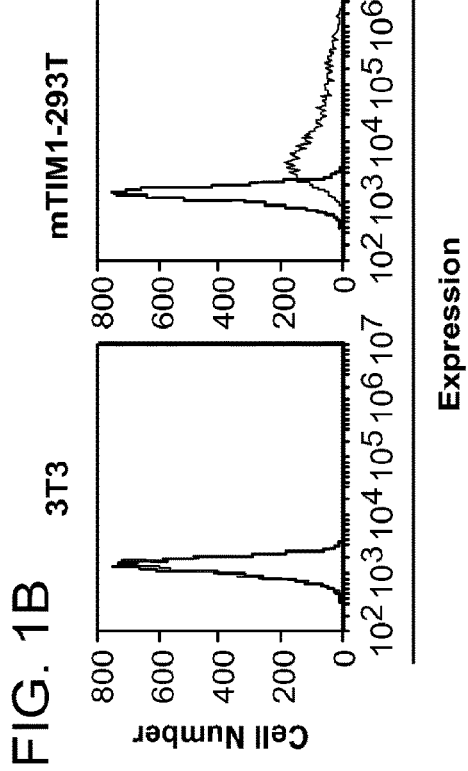
FIG. 1A
FIG. 1B
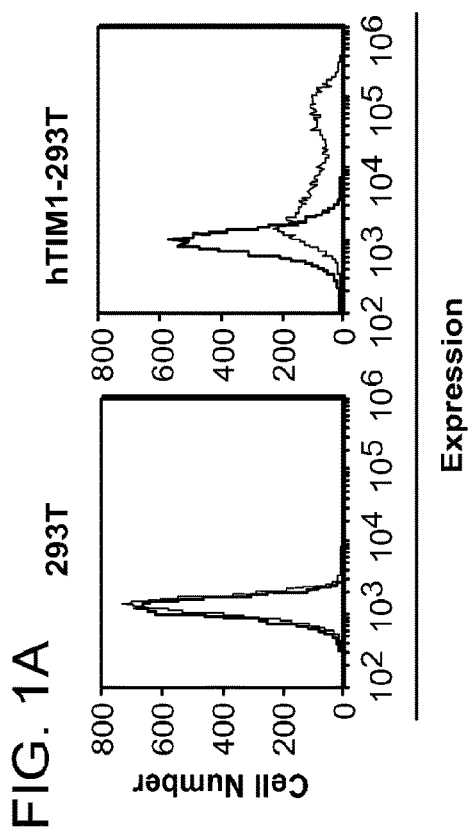
FIG. 1C
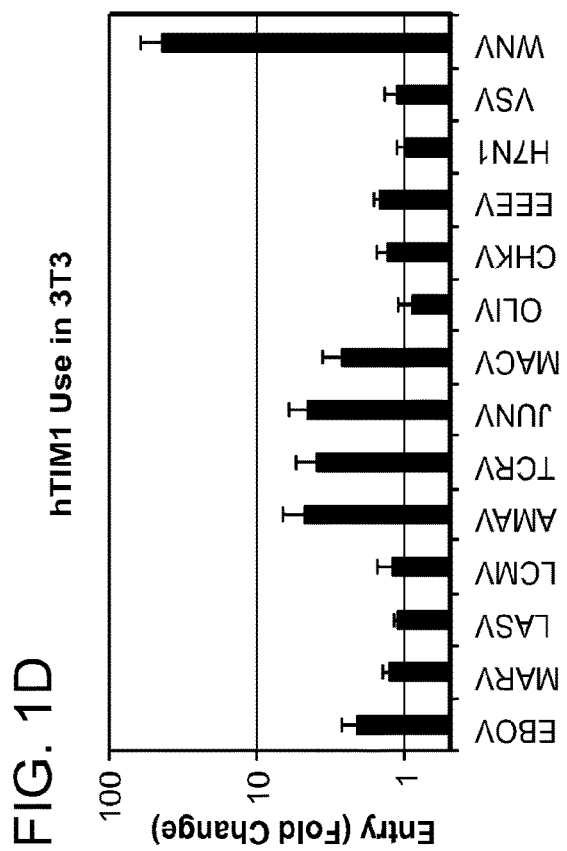
FIG. 1D
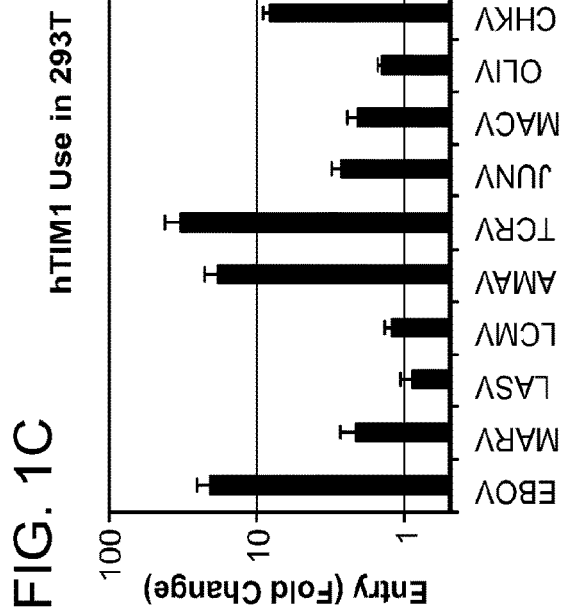

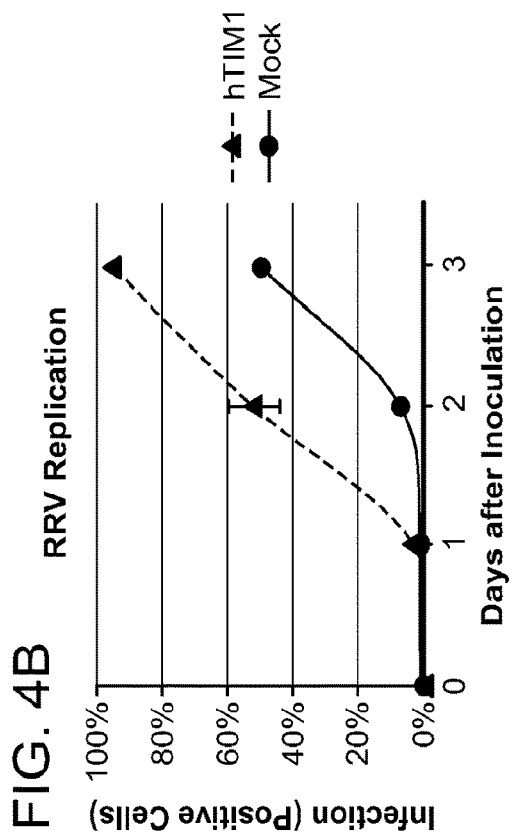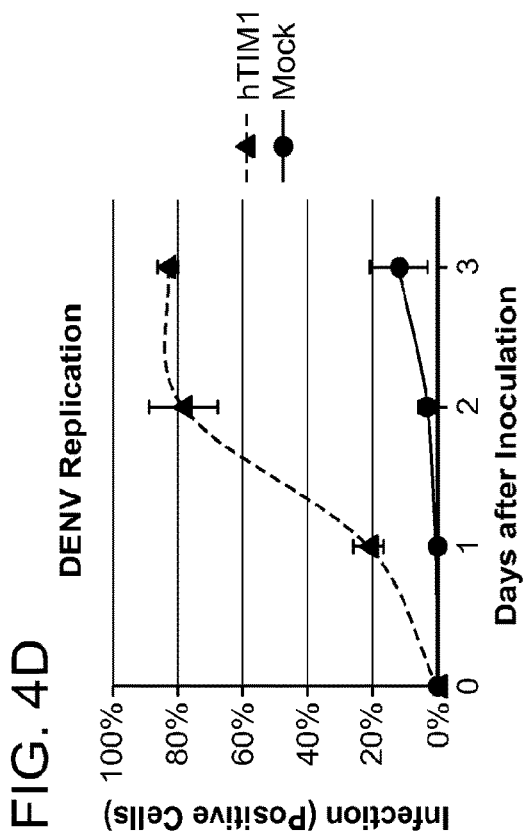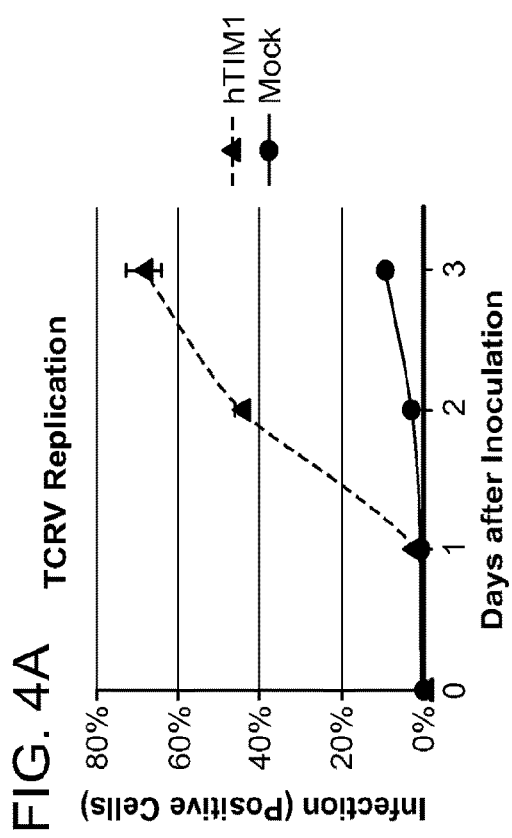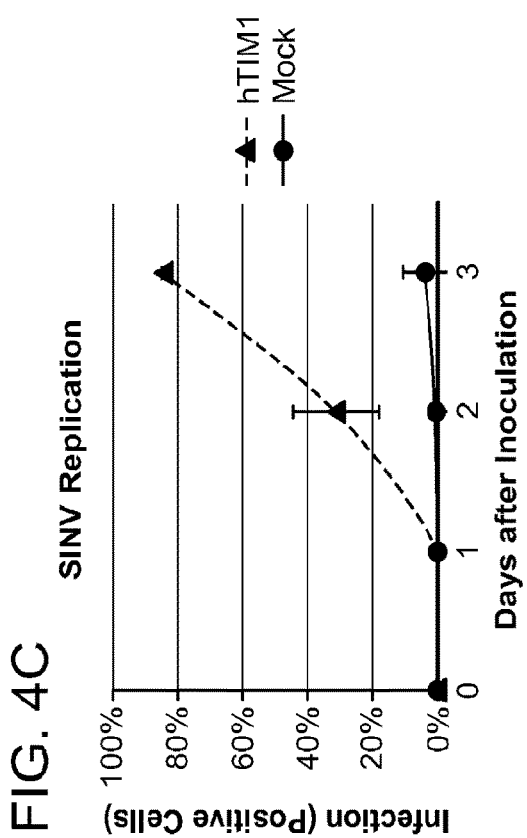
FIG. 4A TCRV Replication
FIG. 4B RRV Replication
FIG. 4C SINV Replication
FIG. 4D DENV Replication

FIG. 6

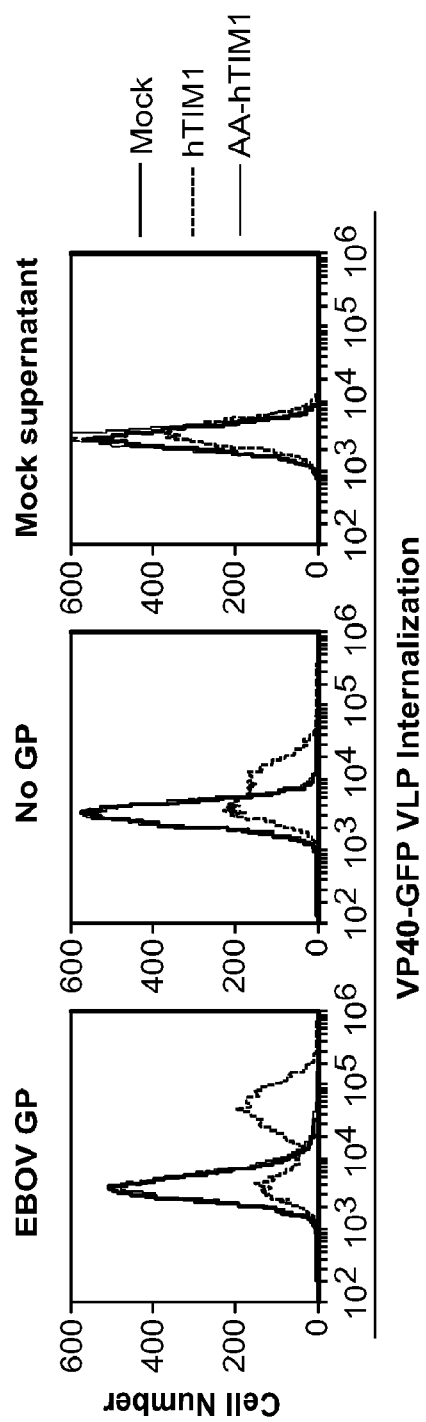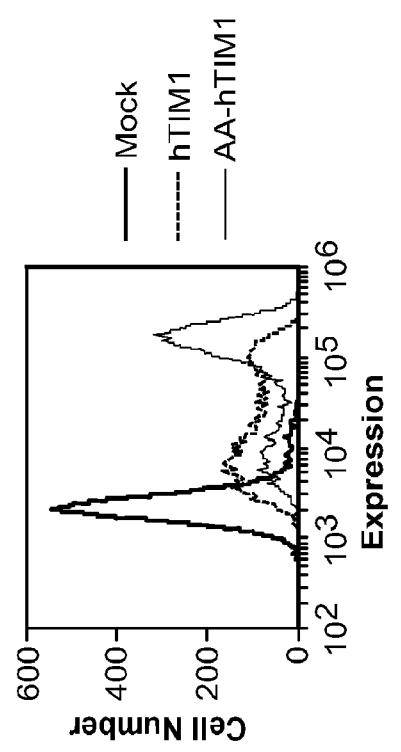
FIG. 7A
FIG. 7B

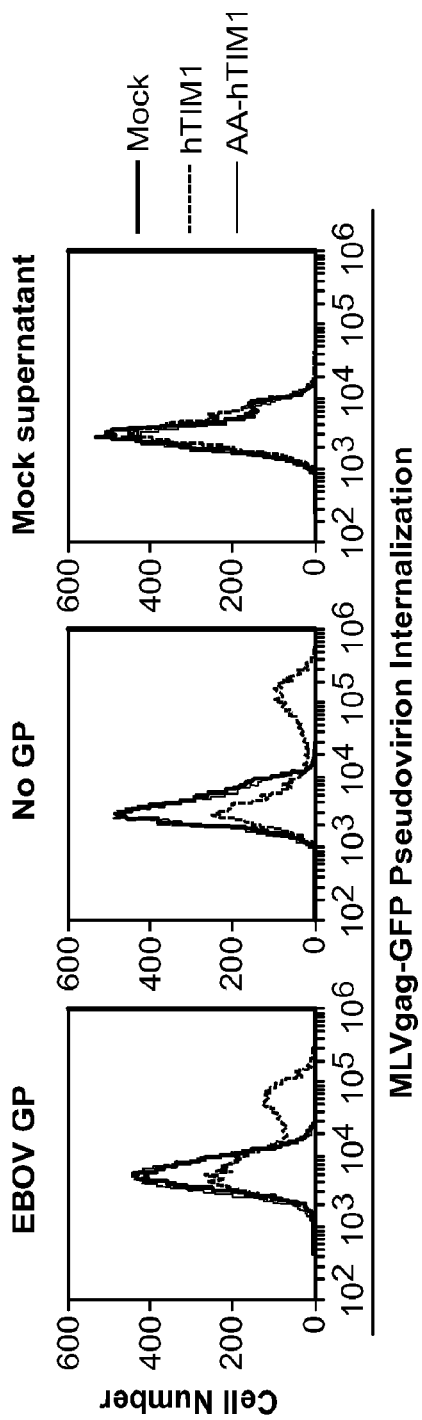
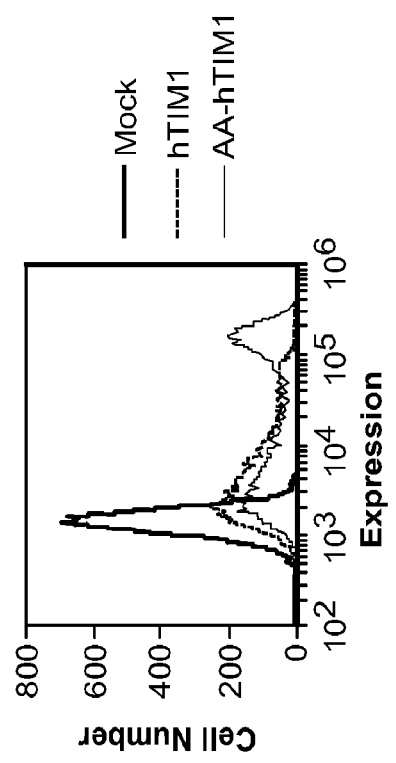
FIG. 7C
FIG. 7D

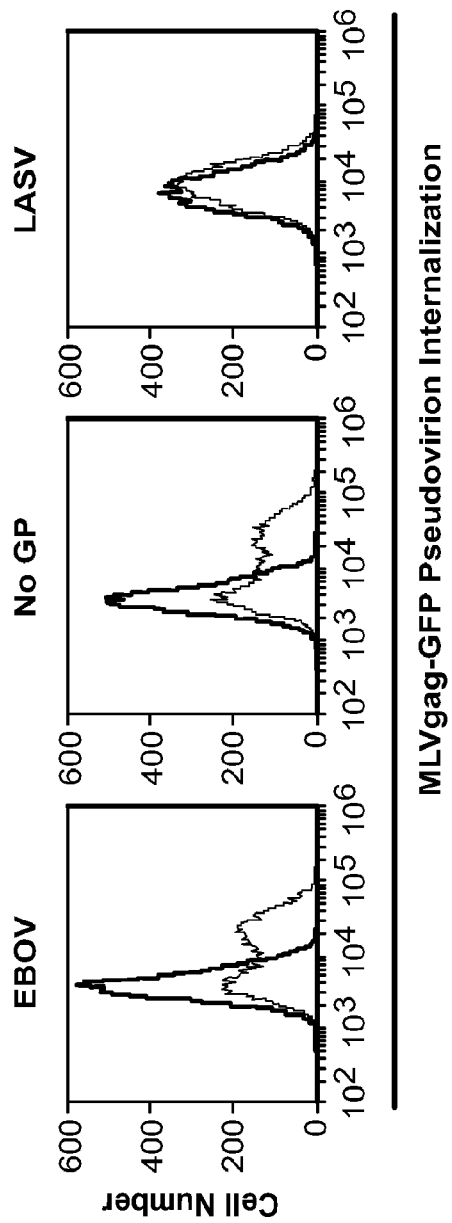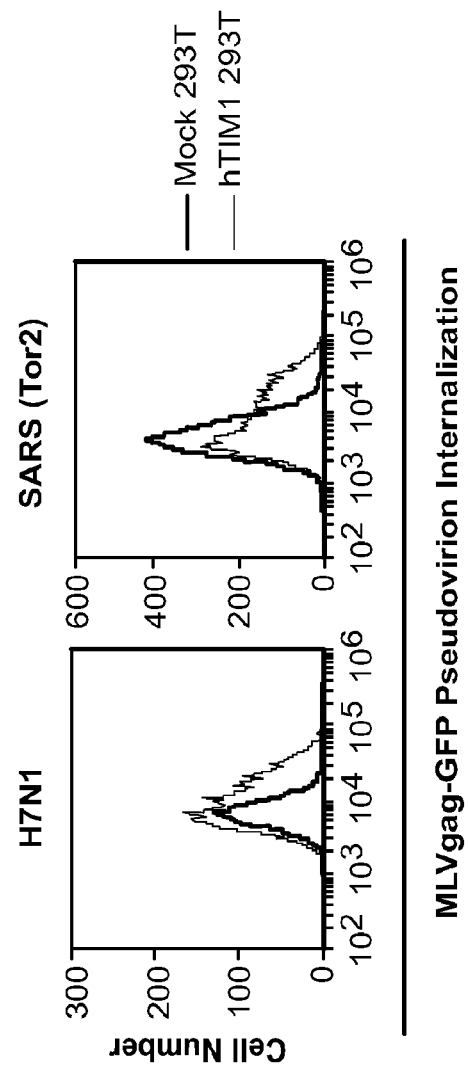
FIG. 8A

FIG. 8B Liposome Blocking Internalization

FIG. 9 Entry of Various SARS-CoV Isolates in 293T

FIG. 13

Anti-hTim4 antibody 9F4 blocks the entry of various enveloped viruses.

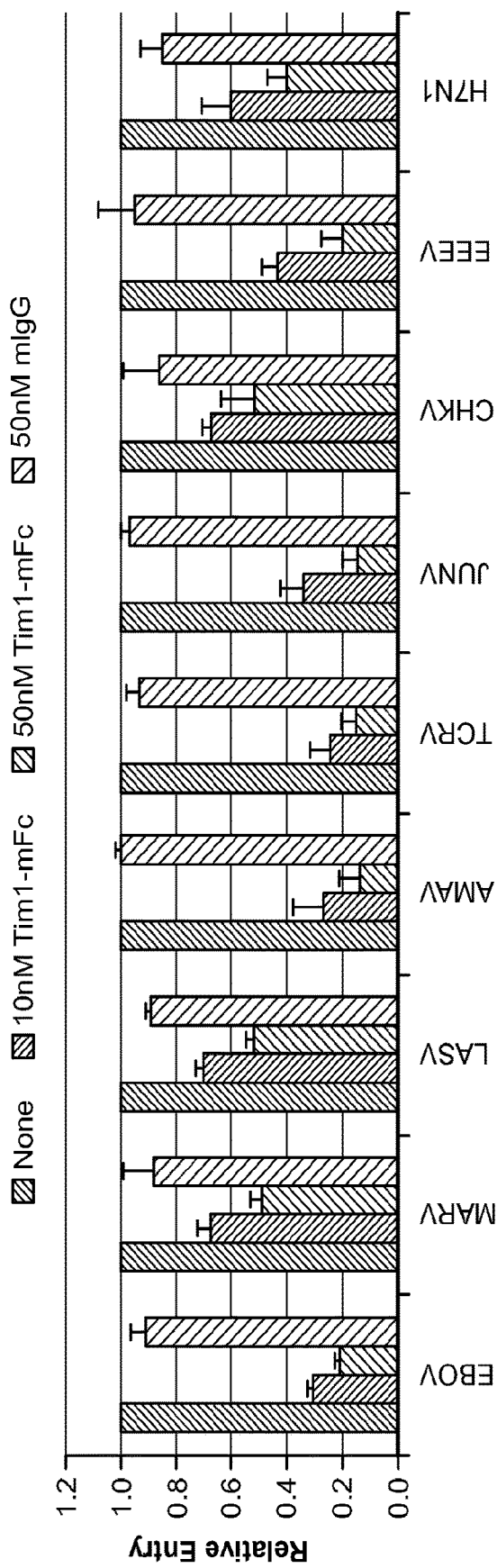

TIM1-mFc inhibits the entry of various pseudoviruses.

Huh7 cells were preincubated for 30 min at room temperature with medium alone (none), purified TIM1-mFc or purified mIgG (negative control), and incubated overnight at 37°C with the indicated pseudoviruses in the presence of the respective blocking agents. Infection levels were assessed 48h later by measuring GFP expression and normalized to those of untreated cells. Figure shows mean + SD from two independent, duplicated experiments.

FIG. 15

SEQUENCE LISTING

<160> NUMBER OF SEQ ID NOS: 6

<210> SEQ ID NO 1
<211> LENGTH: 359
<212> TYPE: PRT
<213> ORGANISM: Homo sapiens

<400> SEQUENCE: 1

Met His Pro Gln Val Val Ile Leu Ser Leu Ile Leu His Leu Ala Asp
1               5                   10                  15

Ser Val Ala Gly Ser Val Lys Val Gly Gly Glu Ala Gly Pro Ser Val
            20                  25                  30

```
Thr Leu Pro Cys His Tyr Ser Gly Ala Val Thr Ser Met Cys Trp Asn
         35                  40                  45
Arg Gly Ser Cys Ser Leu Phe Thr Cys Gln Asn Gly Ile Val Trp Thr
 50                  55                  60
Asn Gly Thr His Val Thr Tyr Arg Lys Asp Thr Arg Tyr Lys Leu Leu
 65                  70                  75                  80
Gly Asp Leu Ser Arg Arg Asp Val Ser Leu Thr Ile Glu Asn Thr Ala
                 85                  90                  95
Val Ser Asp Ser Gly Val Tyr Cys Cys Arg Val Glu His Arg Gly Trp
             100                 105                 110
Phe Asn Asp Met Lys Ile Thr Val Ser Leu Glu Ile Val Pro Pro Lys
         115                 120                 125
Val Thr Thr Thr Pro Ile Val Thr Thr Val Pro Thr Val Thr Thr Val
     130                 135                 140
Arg Thr Ser Thr Thr Val Pro Thr Thr Thr Val Pro Thr Thr Thr
145                 150                 155                 160
Val Pro Thr Thr Met Ser Ile Pro Thr Thr Thr Val Pro Thr Thr
                165                 170                 175
Met Thr Val Ser Thr Thr Thr Ser Val Pro Thr Thr Thr Ser Ile Pro
            180                 185                 190
Thr Thr Thr Ser Val Pro Val Thr Thr Thr Val Ser Thr Phe Val Pro
        195                 200                 205
Pro Met Pro Leu Pro Arg Gln Asn His Glu Pro Val Ala Thr Ser Pro
    210                 215                 220
Ser Ser Pro Gln Pro Ala Glu Thr His Pro Thr Thr Leu Gln Gly Ala
225                 230                 235                 240
Ile Arg Arg Glu Pro Thr Ser Ser Pro Leu Tyr Ser Tyr Thr Thr Asp
                245                 250                 255
Gly Asn Asp Thr Val Thr Glu Ser Ser Asp Gly Leu Trp Asn Asn Asn
            260                 265                 270
Gln Thr Gln Leu Phe Leu Glu His Ser Leu Leu Thr Ala Asn Thr Thr
        275                 280                 285
Lys Gly Ile Tyr Ala Gly Val Cys Ile Ser Val Leu Val Leu Leu Ala
    290                 295                 300
Leu Leu Gly Val Ile Ile Ala Lys Lys Tyr Phe Phe Lys Lys Glu Val
305                 310                 315                 320
Gln Gln Leu Ser Val Ser Phe Ser Ser Leu Gln Ile Lys Ala Leu Gln
                325                 330                 335
Asn Ala Val Glu Lys Glu Val Gln Ala Glu Asp Asn Ile Tyr Ile Glu
            340                 345                 350
Asn Ser Leu Tyr Ala Thr Asp
        355

<210> SEQ ID NO 2
<211> LENGTH: 1080
<212> TYPE: DNA
<213> ORGANISM: Homo sapiens

<400> SEQUENCE: 2
atgcatcctc aagtggtcat cttaagcctc atcctacatc tggcagattc tgtagctggt      60
tctgtaaagg ttggtggaga ggcaggtcca tctgtcacac taccctgcca ctacagtgga     120
gctgtcacat caatgtgctg gaatagaggc tcatgttctc tattcacatg ccaaaatggc     180
attgtctgga ccaatggaac ccacgtcacc tatcggaagg acacacgcta taagctattg     240
```

-continued

```
ggggaccttt caagaaggga tgtctctttg accatagaaa atacagctgt gtctgacagt    300
ggcgtatatt gttgccgtgt tgagcaccgt gggtggttca atgacatgaa atcaccgta    360
tcattggaga ttgtgccacc caaggtcacg actactccaa ttgtcacaac tgttccaacc    420
gtcacgactg ttcgaacgag caccactgtt ccaacgacaa cgactgttcc aacgacaact    480
gttccaacaa caatgagcat tccaacgaca acgactgttc cgacgacaat gactgtttca    540
acgacaacga gcgttccaac gacaacgagc attccaacaa caacaagtgt tccagtgaca    600
acaacggtct ctacctttgt tcctccaatg cctttgccca ggcagaacca tgaaccagta    660
gccacttcac catcttcacc tcagccagca gaaacccacc ctacgacact gcagggagca    720
ataaggagag aacccaccag ctcaccattg tactcttaca acagatggg gaatgacacc    780
gtgacagagt cttcagatgg cctttggaat aacaatcaaa ctcaactgtt cctagaacat    840
agtctactga cggccaatac cactaaagga atctatgctg gagtctgtat ttctgtcttg    900
gtgcttcttg ctcttttggg tgtcatcatt gccaaaaagt atttcttcaa aaaggaggtt    960
caacaactaa gtgtttcatt tagcagcctt caaattaaag ctttgcaaaa tgcagttgaa   1020
aaggaagtcc aagcagaaga caatatctac attgagaata gtctttatgc cacggattaa   1080
```

<210> SEQ ID NO 3
<211> LENGTH: 301
<212> TYPE: PRT
<213> ORGANISM: Homo sapiens

<400> SEQUENCE: 3

```
Met Phe Ser His Leu Pro Phe Asp Cys Val Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
        35                  40                  45

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125

Ile Lys Pro Ala Lys Val Thr Pro Ala Pro Thr Leu Gln Arg Asp Phe
    130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Ile Gly Ile Tyr Ile Gly Ala Gly
        195                 200                 205

Ile Cys Ala Gly Leu Ala Leu Ala Leu Ile Phe Gly Ala Leu Ile Phe
    210                 215                 220
```

```
Lys Trp Tyr Ser His Ser Lys Glu Lys Ile Gln Asn Leu Ser Leu Ile
225                 230                 235                 240

Ser Leu Ala Asn Leu Pro Pro Ser Gly Leu Ala Asn Ala Val Ala Glu
            245                 250                 255

Gly Ile Arg Ser Glu Glu Asn Ile Tyr Thr Ile Glu Glu Asn Val Tyr
        260                 265                 270

Glu Val Glu Glu Pro Asn Glu Tyr Tyr Cys Tyr Val Ser Ser Arg Gln
    275                 280                 285

Gln Pro Ser Gln Pro Leu Gly Cys Arg Phe Ala Met Pro
    290                 295                 300
```

<210> SEQ ID NO 4
<211> LENGTH: 906
<212> TYPE: DNA
<213> ORGANISM: Homo sapiens

<400> SEQUENCE: 4

```
atgttttcac atcttccctt tgactgtgtc ctgctgctgc tgctgctact acttacaagg     60
tcctcagaag tggaatacag agcggaggtc ggtcagaatg cctatctgcc ctgcttctac    120
accccagccg ccccagggaa cctcgtgccc gtctgctggg gcaaaggagc ctgtcctgtg    180
tttgaatgtg gcaacgtggt gctcaggact gatgaaaggg atgtgaatta ttggacatcc    240
agatactggc taaatgggga tttccgcaaa ggagatgtgt ccctgaccat agagaatgtg    300
actctagcag acagtgggat ctactgctgc cggatccaaa tcccaggcat aatgaatgat    360
gaaaaattta acctgaagtt ggtcatcaaa ccagccaagg tcaccctgc accgactctg    420
cagagagact tcactgcagc ctttccaagg atgcttacca ccaggggaca tggcccagca    480
gagacacaga cactggggag cctccctgat ataaatctaa cacaaatatc cacattggcc    540
aatgagttac gggactctag attggccaat gacttacggg actctggagc aaccatcaga    600
ataggcatct acatcggagc agggatctgt gctgggctgg ctctggctct tatcttcggc    660
gctttaattt tcaaatggta ttctcatagc aaagagaaga tacagaattt aagcctcatc    720
tctttggcca acctccctcc ctcaggattg gcaaatgcag tagcagaggg aattcgctca    780
gaagaaaaca tctataccat tgaagagaac gtatatgaag tggaggagcc caatgagtat    840
tattgctatg tcagcagcag gcagcaaccc tcacaacctt ggggttgtcg ctttgcaatg    900
ccatag                                                              906
```

<210> SEQ ID NO 5
<211> LENGTH: 378
<212> TYPE: PRT
<213> ORGANISM: Homo sapiens

<400> SEQUENCE: 5

```
Met Ser Lys Glu Pro Leu Ile Leu Trp Leu Met Ile Glu Phe Trp Trp
1               5                   10                  15

Leu Tyr Leu Thr Pro Val Thr Ser Glu Thr Val Val Thr Glu Val Leu
            20                  25                  30

Gly His Arg Val Thr Leu Pro Cys Leu Tyr Ser Ser Trp Ser His Asn
        35                  40                  45

Ser Asn Ser Met Cys Trp Gly Lys Asp Gln Cys Pro Tyr Ser Gly Cys
    50                  55                  60

Lys Glu Ala Leu Ile Arg Thr Asp Gly Met Arg Val Thr Ser Arg Lys
65                  70                  75                  80

Ser Ala Lys Tyr Arg Leu Gln Gly Thr Ile Pro Arg Gly Asp Val Ser
```

```
                   85                  90                  95
Leu Thr Ile Leu Asn Pro Ser Glu Ser Asp Ser Gly Val Tyr Cys Cys
            100                 105                 110

Arg Ile Glu Val Pro Gly Trp Phe Asn Asp Val Lys Ile Asn Val Arg
        115                 120                 125

Leu Asn Leu Gln Arg Ala Ser Thr Thr Thr His Arg Thr Ala Thr Thr
130                 135                 140

Thr Thr Arg Arg Thr Thr Thr Ser Pro Thr Thr Thr Arg Gln Met
145                 150                 155                 160

Thr Thr Thr Pro Ala Ala Leu Pro Thr Thr Val Val Thr Thr Pro Asp
                165                 170                 175

Leu Thr Thr Gly Thr Pro Leu Gln Met Thr Thr Ile Ala Val Phe Thr
            180                 185                 190

Thr Ala Asn Thr Cys Leu Ser Leu Thr Pro Ser Thr Leu Pro Glu Glu
        195                 200                 205

Ala Thr Gly Leu Leu Thr Pro Glu Pro Ser Lys Glu Gly Pro Ile Leu
    210                 215                 220

Thr Ala Glu Ser Glu Thr Val Leu Pro Ser Asp Ser Trp Ser Ser Val
225                 230                 235                 240

Glu Ser Thr Ser Ala Asp Thr Val Leu Leu Thr Ser Lys Glu Ser Lys
                245                 250                 255

Val Trp Asp Leu Pro Ser Thr Ser His Val Ser Met Trp Lys Thr Ser
            260                 265                 270

Asp Ser Val Ser Ser Pro Gln Pro Gly Ala Ser Asp Thr Ala Val Pro
        275                 280                 285

Glu Gln Asn Lys Thr Thr Lys Thr Gly Gln Met Asp Gly Ile Pro Met
    290                 295                 300

Ser Met Lys Asn Glu Met Pro Ile Ser Gln Leu Leu Met Ile Ile Ala
305                 310                 315                 320

Pro Ser Leu Gly Phe Val Leu Phe Ala Leu Phe Val Ala Phe Leu Leu
                325                 330                 335

Arg Gly Lys Leu Met Glu Thr Tyr Cys Ser Gln Lys His Thr Arg Leu
            340                 345                 350

Asp Tyr Ile Gly Asp Ser Lys Asn Val Leu Asn Asp Val Gln His Gly
        355                 360                 365

Arg Glu Asp Glu Asp Gly Leu Phe Thr Leu
    370                 375

<210> SEQ ID NO 6
<211> LENGTH: 1137
<212> TYPE: DNA
<213> ORGANISM: Homo sapiens

<400> SEQUENCE: 6
atgtccaaag aacctctcat tctctggctg atgattgagt tttggtggct ttacctgaca      60
ccagtcactt cagagactgt tgtgacggag gttttgggtc accgggtgac tttgccctgt      120
ctgtactcat cctggtctca aacagcaac  agcatgtgct gggggaaaga ccagtgcccc      180
tactccggtt gcaaggaggc gctcatccgc actgatggaa tgagggtgac ctcaagaaag      240
tcagcaaaat atagacttca ggggactatc cgagaggtg  atgtctcctt gaccatctta      300
aaccccagtg aaagtgacag cggtgtgtac tgctgccgca tagaagtgcc tggctggttc      360
aacgatgtaa agataaacgt gcgcctgaat ctacagagag cctcaacaac cacgcacaga      420
acagcaacca ccaccacacg cagaacaaca acaacaagcc ccaccaccac ccgacaaatg      480
```

```
acaacaaccc cagctgcact tccaacaaca gtcgtgacca cacccgatct cacaaccgga    540
acaccactcc agatgacaac cattgccgtc ttcacaacag caaacacgtg cctttcacta    600
accccaagca cccttccgga ggaagccaca ggtcttctga ctcccgagcc ttctaaggaa    660
gggcccatcc tcactgcaga atcagaaact gtcctcccca gtgattcctg gagtagtgct    720
gagtctactt ctgctgacac tgtcctgctg acatccaaag agtccaaagt ttgggatctc    780
ccatcaacat cccacgtgtc aatgtggaaa acgagtgatt ctgtgtcttc tcctcagcct    840
ggagcatctg atacagcagt tcctgagcag aacaaaacaa caaaaacagg acagatggat    900
ggaataccca tgtcaatgaa gaatgaaatg cccatctccc aactactgat gatcatcgcc    960
ccctccttgg gatttgtgct cttcgcattg tttgtggcgt ttctcctgag agggaaactc    1020
atggaaacct attgttcgca gaaacacaca aggctagact acattggaga tagtaaaaat    1080
gtcctcaatg acgtgcagca tggaagggaa gacgaagacg gccttttttac cctctaa     1137
```

COMPOSITIONS AND METHODS FOR INHIBITING VIRAL ENTRY

CROSS REFERENCE TO RELATED APPLICATIONS

This application is the U.S. national phase, pursuant to 35 U.S.C. § 371, of international application Ser. No. PCT/US2013/074678, filed Dec. 12, 2013, designating the United States and published in English on Jun. 19, 2014 as publication No. WO 2014/093627 A2 which claims priority to U.S. Provisional application No. 61/737,070, filed Dec. 13, 2012. The entire contents of the aforementioned patent applications are incorporated by reference herein.

STATEMENT OF RIGHTS TO INVENTIONS MADE UNDER FEDERALLY SPONSORED RESEARCH

This invention was made with government support under Grant Nos: 2R01A1074879; U54 AI057159; P01 AI054456; and R01 AI089955, awarded by The National Institutes of Health. The government has certain rights in the invention.

SEQUENCE LISTING

This instant application contains a Sequence Listing which has been submitted electronically in ASCII format and is hereby incorporated by reference in its entirety. Said ASCII copy, created Apr. 19, 2021 is named 048218-527N01US_SL.txt and is 13,782 bytes.

BACKGROUND OF THE INVENTION

The development of antiviral therapies based on similar characteristics of a wide range of enveloped viruses (e.g., alphavirus, flavivirus, Filovirus, and New World arenavirus) has the potential to provide a broad-spectrum antiviral therapy.

Alphaviruses comprise a set of genetically, structurally, and serologically related mosquito-borne viruses of the Togaviridae family. Twenty-seven known viruses and virus subtypes have been classified within the alphavirus genus, eleven of which are recognized to be pathogenic to humans. Infection by Eastern equine encephalitis virus (EEEV) and Chikungunya virus (CHKV) result in acute onset of flu-like fever, followed by the development of a rash and arthritis. The evolution and spread of alphaviruses into new geographic areas, and the disease severity resulting from alphavirus infection present a serious public health issue in the absence of vaccines or anti-viral therapies.

Flaviviruses comprise a set of genetically, structurally, and serologically related mosquito-borne or tick-borne viruses of the Flaviviridae family that also pose current or potential threats to global public health. Dengue Virus (DENV) and West Nile Virus (WNV) result in a range of symptoms ranging from flu-like symptoms such as fever, chills, and vomitting to severe symptoms such as muscular rigidity, photophobia, hyperexcitability, abnormal tremors and movements, incoordination, paralysis, sensory loss, convulsions, respiratory dysfunction, and severe hemorrhages. Like other arthropod-borne viruses, the evolution and spread of flaviruses into new geographic areas, and the disease severity resulting from flavivirus infection present a serious public health issue in the absence of vaccines or anti-viral therapies. Useful targets for broad-spectrum anti-viral therapies are urgently required.

SUMMARY OF THE INVENTION

The present invention features compositions and methods for the prevention or treatment of a disease or disorder mediated by enveloped viruses (e.g., filoviruses EBOV and MARV; arenaviruses JUNV, MACV, AMAV, and TCRV; alphaviruses EEEV, CHKV, SINV, and RRV; and flaviviruses DENV and WNV).

As reported in detail below, use of anti-TIM1 or TIM4 antibodies, or TIM1- or TIM4-Ig blocked phosphatidylserine-mediated infection of a wide range of enveloped viruses including filoviruses, flaviviruses, arenaviruses, and alphaviruses. Advantageously, the disclosures herein show that the interaction between a wide range of viruses and a wide range of target-cell molecules can be blocked by antibodies to TIM proteins (anti-TIM1 or anti-TIM4) or TIM1- or TIM4-Ig fusion molecules, thus limiting viral infection. Previous reports either showed an incorrect mechanism, and/or focused on individual viruses and other target-cell interactions. The invention is based at least in part on these discoveries.

Accordingly, the invention provides agents that inhibit viral entry by inhibiting the interaction of the viral envelope with a TIM protein (e.g., TIM1, TIM3, TIM4) or other phosphatidylserine receptor.

In one aspect, the invention provides a method for treating or preventing a virus infection in a subject, involving administering to the subject an effective amount of an agent that inhibits viral entry.

In another aspect, the invention provides a method for treating or preventing viral entry of a cell, involving contacting the cell with an effective amount of an agent that inhibits viral entry.

In another aspect, the invention provides a kit containing an agent that inhibits viral entry, and directions for the use of the agent to treat or prevent viral infection in a subject.

In various embodiments of any of the aspects delineated herein, the agent inhibits viral entry via one or more of a T-cell Immunoglobulin and Mucin-domain containing protein (TIM protein) or a phosphatidylserine receptor. In various embodiments, the TIM protein is one or more of hTIM1, hTIM3, and hTIM4. In various embodiments of any of the aspects delineated herein, the agent is an inhibitory nucleic acid molecule that is complementary to at least a portion of a TIM protein. In various embodiments, the inhibitory nucleic acid molecule is one or more of an antisense molecule, an siRNA, or an shRNA. In various embodiments of any of the aspects delineated herein, the agent is an antibody or fragment thereof that selectively binds to a TIM protein. In various embodiments, the antibody is a monoclonal or polyclonal antibody. In various embodiments of any of the aspects delineated herein, the agent is an exogenous TIM protein or fragment thereof. In various embodiments of any of the aspects delineated herein, the agent is 1,2-diacyl-sn-glycero-3-phospho-L-serine (PS) or 1,2-diacyl-sn-glycero-3-phosphoethanolamine (PE).

In various embodiments of any of the aspects delineated herein, the virus is an enveloped virus. In various embodiments, the enveloped virus is an alphavirus, flavivirus, filovirus, or arenavirus. In particular embodiments, the virus is Ebola virus (EBOV), Marburg virus (MARV), Amapari virus (AMAV), Tacaribe virus (TCRV), Junin virus (JUNV), Machupo virus (MACV), Chikungunya virus (CHKV), Easter equine encephalitis virus (EEEV), Dengue virus (DENV), West Nile virus (WNV), Sinbis virus (STNV) or Ross River virus (RRV).

In various embodiments of any of the aspects delineated herein, the agent is administered in one or more doses. In various embodiments, the agent is administered at one, two, three, four, five, six, seven, or eight week intervals. In various embodiments of any of the aspects delineated herein, the agent reduces viral entry by at least 60%, 65%, 70%, 75%, 80%, 85%, 90%, 95%, 96%, 97%, 98%, 99%, or 100%. In various embodiments of any of the aspects delineated herein, the administration of the agent protects the subject against viremia or the inflammatory consequences of a viral infection. In various embodiments of any of the aspects delineated herein, the agent protects the subject or cell from lethality.

Compositions and articles defined by the invention were isolated or otherwise manufactured in connection with the examples provided below. Other features and advantages of the invention will be apparent from the detailed description, and from the claims.

Any compositions or methods provided herein can be combined with one or more of any of the other compositions and methods provided herein. The recitation of an embodiment for any aspect herein includes that embodiment as any single embodiment or in combination with any other embodiments or portions thereof.

Definitions

By "agent" is meant any small molecule chemical compound, antibody, nucleic acid molecule, or polypeptide, or fragments thereof.

As used herein, the term "adjuvant" is meant to refer to a compound that, when used in combination with a specific immunogen in a formulation, will augment, alter or modify the resultant immune response. Modification of the immune response includes intensification or broadening the specificity of either or both antibody and cellular immune responses. Modification of the immune response can also mean decreasing or suppressing certain antigen-specific immune responses.

As used herein "alphavirus" is meant to refer to RNA-containing viruses that belong to the Togaviridae family of viruses. Exemplary alphaviruses include but are not limited to Easter equine encephalitis virus (EEEV), Western equine encephalitis virus (WEEV), Venezuelan equine encephalitis virus (VEEV), Semliki forest virus (SFV), Chikungunya virus (CHKV), Sindbis virus (SINV), Mayaro virus (MAYV), Ross River virus (RRV), Barmah Forest virus (BFV), and Ockelbo virus (OCK).

As used herein "flavivirus" is meant to refer to RNA-containing viruses that belong to the group Flaviviridae family of viruses. Exemplary flaviviruses include but are not limited to yellow fever virus (YFV), Dengue virus (DENV), West Nile Virus (WNV), Japanese encephalitis virus (JEV), and Tickborne encephalitis virus (TBEV).

As used herein "arenavirus" is meant to refer to RNA-containing viruses that belong to the Arenaviridae family of viruses. Exemplary arenaviruses include but are not limited to Junin virus (JUNV), Machupo virus (MACV), Amapari virus (AMAV), Tacaribe virus (TCRV), Oliveros virus (OLIV), Lassa fever virus (LASV), and lymphocytic choriomeningitis virus (LCMV).

As used herein "filovirus" is meant to refer to RNA-containing viruses that belong to the Filoviridae family of viruses. Exemplary filoviruses include but are not limited to Ebola virus (EBOV) and Marburg virus (MARV).

As used herein "inducing immunity" is meant to refer to any immune response generated against an antigen. In one embodiment, immunity is mediated by antibodies against an infectious agent, which is exhibited by a vertebrate (e.g., a human), that prevents or ameliorates an infection or reduces at least one symptom thereof. Vaccines or immunogenic compositions can stimulate the production of antibodies that, for example, neutralize infectious agents, block infectious agents from entering cells, block replication of infectious agents, and/or protect host cells from infection and destruction. The term can also refer to an immune response that is mediated by T-lymphocytes and/or other white blood cells against an infectious agent, exhibited by a vertebrate (e.g., a human), that prevents or ameliorates an infection (e.g., alphavirus or flavivirus) or reduces at least one symptom thereof.

By "ameliorate" is meant decrease, suppress, attenuate, diminish, arrest, or stabilize the development or progression of a disease or a symptom thereof.

By "alteration" is meant a change in an amino acid or nucleotide at a specified position with reference to a polypeptide sequence or polynucleotide sequence. As used herein, an alteration includes a substitution, deletion, or insertion of an amino acid or nucleotide at a specified position of a polypeptide or polynucleotide. In some embodiments, an alteration is in a viral or host cell protein.

By "alteration" is meant a change (increase or decrease) with reference to the expression levels or activity of a gene or polypeptide as detected by standard art known methods, such as those described herein. As used herein, an alteration includes a 10%, 25%, 50%, 75%, 100% or greater change in expression levels. An alteration includes a 10-, 20-, 50-, 70-, 80-, 90-, 100-, 200-, 500-, 1000-fold or greater change in expression levels.

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "disease" is meant any condition or disorder that damages or interferes with the normal function of a cell, tissue, or organ. Examples of diseases include viral infections including but not limited to infection by enveloped viruses (e.g., filoviruses EBOV and MARV; arenaviruses JUNV, MACV, AMAV, and TCRV; alphaviruses EEEV, CHKV, SINV, and RRV; and flaviviruses DENV and WNV).

By "effective amount" is meant the amount of an agent required to ameliorate the symptoms of a disease relative to an untreated patient. The effective amount of active compound(s) used to practice the present invention for prevention or treatment of a disease varies depending upon the manner of administration, the age, body weight, and general health of the subject. Ultimately, the attending physician or veterinarian will decide the appropriate amount and dosage regimen. Such amount is referred to as an "effective" amount.

The invention provides a number of targets that are useful for the development of highly specific drugs to treat or prevent a diseases delineated herein. In addition, the methods of the invention provide a facile means to identify therapies that are safe for use in subjects. In addition, the methods of the invention provide a route for analyzing virtually any number of compounds for effects on a disease described herein with high-volume throughput, high sensitivity, and low complexity.

By "exogenous" is meant a portion of a membrane bound protein that is extracellular, outside the cell, or outside the plasma membrane of the cell. In one embodiment, the receptor binding domain of a TIM protein is exogenous.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

By "inhibits" or "reduces" is meant a negative alteration of at least 10%, 25%, 50%, 60%, 65%, 70%, 75%, 80%, 85%, 90%, 95%, 96%, 97%, 98%, 99%, or 100%.

By "inhibitory nucleic acid molecule" is meant a polynucleotide that disrupts the expression of a target nucleic acid molecule or an encoded polypeptide. Exemplary inhibitory nucleic acid molecules include, but are not limited to, shRNAs, siRNAs, antisense nucleic acid molecules, and analogs thereof.

By "isolated polynucleotide" is meant a nucleic acid molecule (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any protein or polynucleotide having an alteration in expression level or activity that is associated with a disease or disorder.

As used herein, "obtaining" as in "obtaining an agent" includes synthesizing, purchasing, or otherwise acquiring the agent.

By "phosphatidylserine receptor" is meant a polypeptide having binding activity to the phospholipid phosphatidylserine and which is involved in viral entry of enveloped viruses. In accordance with the invention, blocking the binding of phosphatidylserine receptor and phosphatidyl serine in an enveloped virus inhibits viral entry.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "specifically binds" is meant a compound or antibody that recognizes and binds a polypeptide of the invention, but which does not substantially recognize and bind other molecules in a sample, for example, a biological sample, which naturally includes a polypeptide of the invention.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/ PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "subject" is meant a mammal, including, but not limited to, a human or non-human mammal, such as a bovine, equine, canine, ovine, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

By "T-cell Immunoglobulin and Mucin-domain containing protein" or "TIM protein" is meant a polypeptide or fragment thereof having at least about 80% amino acid sequence identity to a naturally occurring TIM protein and having inhibitory activity on viral entry. TIM proteins may also have phosphatidylserine binding activity. In one embodiment, the TIM protein has at least about 85%, 90%, 95% or greater amino acid sequence identity with TIM1, TIM3, TIM4 or fragment thereof.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the term "vaccine" refers to a composition to be used in generating an immune response. In particular embodiments, a vaccine of the invention is in a form that is capable of being administered to a subject and which induces a protective immune response sufficient to induce immunity to prevent and/or ameliorate an infection and/or to reduce at least one symptom of an infection and/or to enhance the efficacy of another dose of VLPs or DNA vaccines. Typically, the vaccine comprises a pharmaceutically acceptable excipient, such as conventional saline or buffered aqueous solution medium in which the composition of the present invention is suspended or dissolved. In this form, the composition of the present invention can be used conveniently to prevent, ameliorate, or otherwise treat an infection. Upon introduction into a host, the vaccine induces an immune response including, but not limited to, the production of antibodies and/or cytokines and/or the activation of cytotoxic T cells, antigen presenting cells, helper T cells, dendritic cells and/or other cellular responses. In certain embodiments, a vaccine can also be a protein. For example, recombinant proteins have been produced by genetically engineering cells to produce one or more foreign genes, which in turn produce proteins that serve as the immunogen.

As used herein, the terms "virus-like particle" (VLP) or "pseudovirus" refer to a structure that in at least one attribute resembles a virus, but which has not been demonstrated to be infectious. Virus-like particles in accordance with the invention do not carry genetic information encoding the proteins of the virus-like particles. In general, virus-like particles lack a viral genome and, therefore, are noninfectious. In addition, virus-like particles can often be produced in large quantities by heterologous expression and can be easily purified.

As used herein, the term "viral entry" refers to the process of viral contact with the host cell and introduction of viral material into the cell. This process is an early stage of infection in the viral life cycle and includes steps associated with cell attachment (e.g., via a receptor), membrane fusion of viral and host membranes, entry pore formation, and viral penetration into the host cell or entry via endocytosis.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIGS. 1A-1F depict that hTIM1 promoted infection mediated by a range of viral entry proteins. FIG. 1A shows that human 293T cells do not express TIM1. 293T or 293T cells transfected with hTIM1 (hTIM1-293T) were stained with anti-hTIM1 antibody (R&D Systems) (red) or, as a negative control, with mFc (black). FIG. 1B shows that murine 3T3 cells do not express TIM1. 3T3 and mTIM1-transfected 293T (mTIM1-293T) cells were stained with anti-mTIM1-PE antibody (red). Unstained cells (black) and cells stained with anti-mIFNγ-PE (blue) served as negative controls. FIG. 1C shows that exogenous hTIM1 increased the entry of various pseudoviruses in 293T cells. 293T cells were transfected with plasmids expressing hTIM1 or, as a negative control, hACE2. Cells were infected 48 hr. later with the indicated MLV pseudoviruses or with WNV VLPs, both carrying the GFP reporter gene. The following day, GFP expression was quantified by flow cytometry. Fold changes in entry were calculated by dividing mean fluorescence intensity observed in hTIM1-expressing 293T cells by those in hACE2-expressing 293T cells. Figure shows mean+SD from three independent, duplicated experiments. FIG. 1D shows that exogenous hTIM1 modestly increased pseudovirus entry in 3T3 cells. 3T3 cells were transduced with hTIM1 or hACE2 and infected 48 hr. later as in FIG. 1C. Infection levels were assessed two days later and data presented as in FIG. 1C. FIG. 1C shows mean+SD from three independent, duplicated experiments. FIG. 1E shows that human Huh7 cells express high levels of TIM1. Huh7 cells and 293T cells were stained for TIM1 expression as in FIG. 1A. FIG. 1F shows that inhibition of entry by an anti-hTIM1 antibody paralleled use of hTIM1 by various viruses. Huh7 cells were preincubated for 30 min. at room temperature with medium alone (none), the anti-hTIM1 antibody 3D1 or purified mIgG (negative control), and incubated overnight at 37° C. with the indicated pseudoviruses in the presence of the respective blocking agents. Infection levels were assessed 48 hr. later as in FIG. 1C and normalized to those of untreated cells. FIG. 1F shows mean+SD from three independent, duplicated experiments.

FIG. 2A depicts hTIM1 use in 293T or 3T3 cells represented using % positive cells. In parallel with the mean fluorescence intensity (m.f.i.), infection levels were assessed using the percentage of GFP positive cells. Note that these graphs also show data for MLV pseudoviruses bearing no viral entry glycoproteins (no GP). FIG. 2A shows representative results of one of three experiments performed in duplicates. FIG. 2B shows results of 293T and 3T3 cells subject to a longer infection. In parallel with the short infection times used for assessing hTIM1 usage in FIGS. 1C and 1D, 293T and 3T3 cells were subject to a longer infection (4 hr. for 293T and 12 hr. for 3T3) to assess whether pseudovirus titers might be limiting, especially for viruses showing low or no TIM1 use. FIG. 2B shows representative results from one of three experiments performed in duplicates. FIG. 2C depicts hTIM1 use in 293T or 3T3 cells represented using % positive cells. In parallel with the mean fluorescence intensity (m.f.i.), infection levels were assessed using the percentage of GFP positive cells. Note that these graphs also show data for MLV pseudoviruses bearing no viral entry glycoproteins (no GP). FIG. 2C shows representative results of one of three experiments performed in duplicates. FIG. 2D shows results of 293T and 3T3 cells subject to a longer infection. In parallel with the short infection times used for assessing hTIM1 usage in FIGS. 1C and 1D, 293T and 3T3 cells were subject to a longer infection (4 hr. for 293T and 12 hr. for 3T3) to assess whether pseudovirus titers might be limiting, especially for viruses showing low or no TIM1 use. FIG. 2D shows representative results from one of three experiments performed in duplicates. FIG. 2E depicts that SARS (Tor2) pseudovirus entry is not enhanced by exogenous hTIM1 in 293T cells. SARS (Tor2) pseudovirus entry into 293T cells expressing the empty vector (mock), hTIM1 or the SARS-CoV receptor hACE2 was assessed as in FIG. 1C. Since 293T or 3T3 cells are completely refractory to SARS pseudovirus entry in the absence of exogenous hACE2, both positive and negative control cells were used, making it necessary to separate this data from FIGS. 1C and 1D. FIG. 2E shows mean+SD of three independent, duplicated experiments. FIG. 2F depicts that SARS (Tor2) pseudovirus entry is not enhanced by exogenous hTIM1 in 3T3 cells. SARS (Tor2) pseudovirus entry into 3T3 cells expressing the empty vector (mock), hTIM1 or the SARS-CoV receptor hACE2 was assessed as in FIG. 1C. Since 3T3 cells are completely refractory to SARS pseudovirus entry in the absence of exogenous hACE2, both positive and negative control cells were used, making it necessary to separate this data from FIGS. 1C and 1D. FIG. 2F shows mean+SD of three independent, duplicated experiments.

FIG. 3A depicts studies with infectious TCRV. Cells were trypsinized 2 days later and stained with immune ascitic fluids. Representative results of two duplicate experiments are shown. FIG. 3B depicts studies with infectious RRV. Cells were trypsinized 2 days later and stained with immune ascitic fluids. Representative results are shown of mean±SD from two independent, duplicate experiments. FIG. 3C depicts studies with infectious SINV. Cells were trypsinized 2 days later and stained with immune ascitic fluids. Representative results are shown of mean±SD from two independent, duplicate experiments. FIG. 3D depicts studies with infectious H1N1. Cells were trypsinized the following day and stained with anti-FLUAV antibodies. Representative results are shown of mean±SD from two independent, duplicate experiments. FIG. 3E depicts studies with infectious DENV. Cells were trypsinized the following day and stained with anti-DENV antibodies. Representative results are shown of mean±SD from two independent, duplicate experiments.

FIGS. 4A-4D depict studies of hTim1 use by infectious viruses. 293T cells transduced with hTIM1 or hACE2 were incubated with infectious virus, washed, and further incubated for one, two or three consecutive days. At the indicated days, cells were trypsinized, stained and infection levels were measured by flow cytometry. FIG. 4A depicts studies of hTim1 use by TCRV. Cells were incubated for 6 hr with infectious TCRV and stained with immune ascitic fluids. Representative results are shown of two duplicate experiments. FIG. 4B depicts studies of hTim1 use by RRV. Cells were incubated for 6 hr with infectious RRV and stained with immune ascitic fluids. Representative results are shown of mean±SD from two duplicate experiments. FIG. 4C depicts studies of hTim1 use by SINV. Cells were incubated for 6 hr with infectious SINV and stained with immune ascitic fluids. Representative results are shown of mean±SD from two duplicate experiments. FIG. 4D depicts studies of hTim1 use by DENV. Cells were incubated for 1 hr with infectious DENV and stained with immune ascitic fluids. Representative results are shown of mean±SD from two duplicate experiments.

FIG. 5A depicts a hTIM1 variant deficient in PS binding (AA-hTIM1) did not support viral entry. 293T cells were transduced with hACE2 (mock), hTIM1 or AA-hTIM1, and infected 2 days later with the indicated pseudoviruses or WNV VLPs. Entry was determined by GFP-expression measured by flow cytometry. FIG. 5A depicts representative results from one of three independent, duplicated experiments. M.f.i.: mean fluorescent intensity. FIG. 5B shows assessment of expression levels of hTIM1 and AA-hTIM1. In parallel with the infection in FIG. 5A, expression levels of hTIM1 and AA-hTIM1 were assessed as in FIG. 1A. FIG. 5C shows hTIM1-mediated virus entry enhancement was efficiently blocked by PS-containing liposomes. 293T cells transduced with hACE2 (mock) or hTIM1 were preincubated for 20 min. at room temperature with medium alone (none) or with liposomes consisting of either 50% PS and 50% PC (PS/PC) or PC alone (PC). Pseudoviruses or WNV VLPs were then added for a 30 min. infection at 37° C., after which unbound liposomes and viruses were washed away and cells supplemented with fresh medium. Entry was quantified as in FIG. 5A and normalized to those of untreated hTIM1-expressing cells. FIG. 5C shows mean+SD of three independent, duplicated experiments.

FIG. 6 depicts PE-containing liposomes also blocked hTIM1-mediated enhancement of viral entry. 293T cells transduced with hACE2 (mock) or hTIM1 were preincubated for 20 min. at room temperature with medium alone (none) or with liposomes consisting of either 50% PE and 50% PC (PE/PC) or PC alone (PC). Pseudoviruses or WNV VLPs were then added for a 30 min. infection at 37° C., after which unbound liposomes and viruses were washed off and cells supplemented with fresh medium. Infection levels were assessed the following day by measuring GFP expression, and normalized to those of untreated hTIM1-expressing cells. Mean+SD from three independent, duplicated experiments are shown.

FIGS. 7A-7D depict viral entry proteins were not required for hTim1-mediated internalization into cells. FIG. 7A shows that VP40-GFP VLPs lacking any viral entry protein were bound and internalized by hTIM1. 293T cells transduced with hACE2 (mock), hTIM1 or AA-hTIM1 were incubated for 6 hr. with VP40-GFP VLPs bearing EBOV GP or no GP. Being inherently fluorescent, these VLPs can be detected independently of whether they undergo fusion, in contrast to the pseudoviruses and VLPs used in previous figures. The supernatant of cells expressing only GFP (mock supernatant) served as negative control. Uninternalized VLPs were detached by acid-stripping and extensive trypsinization, after which internalized VLPs were detected by flow cytometry. FIG. 7A depicts results representative of three independent experiments performed in duplicates. FIG. 7B depicts assessment of expression levels of hTIM1 and AA-hTIM1. In parallel with the infection in FIG. 7A, expression levels of hTIM1 and AA-hTIM1 were assessed as in FIG. 1A. FIG. 7C depicts MLVgag-GFP pseudovirions lacking viral GPs were bound and internalized at least as efficiently as those bearing EBOV GP. 293T cells transduced with hACE2 (mock), hTIM1 or AA-hTIM1 were infected for 6 hr. with purified and RT-activity normalized MLVgag-GFP pseudovirions. The supernatant of cells expressing only GFP (mock supernatant) served as negative control. Cell surface-bound pseudovirions were detached by acid-stripping and extensive trypsinization, after which internalized virions were detected by flow cytometry. Data shown are representative of three independent experiments performed in duplicates. FIG. 7D depicts assessment of expression levels of hTIM1 and AA-hTIM1. In parallel with the infection in FIG. 7C, expression levels of hTIM1 and AA-hTIM1 were assessed as in FIG. 1A.

FIGS. 8A and 8B depict TIM1-mediated pseudovirus internalization did not always coincide with TIM1-mediated virus entry enhancement. FIG. 8A depicts that some pseudoviruses that do not use hTIM1 for productive entry were still efficiently internalized by hTIM1. Mock- or hTIM1-transduced 293T cells were infected for 2 hr. with purified, RT-activity normalized MLVgag-GFP pseudovirions. Uninternalized virions were detached by acid-stripping and extensive trypsinization, after which internalized virions were detected by flow cytometry. Data shown are representative of two independent experiments performed in duplicates. FIG. 8B depicts that hTIM1-mediated pseudovirus internalization was blocked by PS-containing liposomes. Mock- or hTIM1-transduced 293T cells were preincubated for 20 min. at room temperature with medium alone (none), or with liposomes consisting of either 50% PS and 50% PC (PS/PC) or PC alone (PC). MLVgag-GFP pseudovirions, prepared as in A, were then added for a 2 hr infection at 37° C., after which bound virions were detached and internalized virions were detected as in FIG. 8A. FIG. 8B shows mean+SD of two independent, duplicated experiments.

FIG. 9 depicts that receptor affinity did not determine SARS-CoV use of hTIM1. 293T cells were transduced with empty vector (mock) or hACE2, the receptor for SARS-CoV, followed by a second transduction with empty vector or hTIM1. These cells expressing hACE2 and/or hTIM1 were then infected with pseudoviruses carrying the GFP-reporter gene and the entry glycoprotein of the indicated SARS-CoV isolates that use hACE2 with varying efficiency

[36]. Comparable titers of these pseudoviruses were confirmed by infecting cells expressing civet cat ACE2, which is efficiently used by all SARS-CoV isolates [36]. Infection levels were assessed the following day by measuring GFP expression. Shown are representative results of one of three experiments performed in duplicates.

Figure 10:
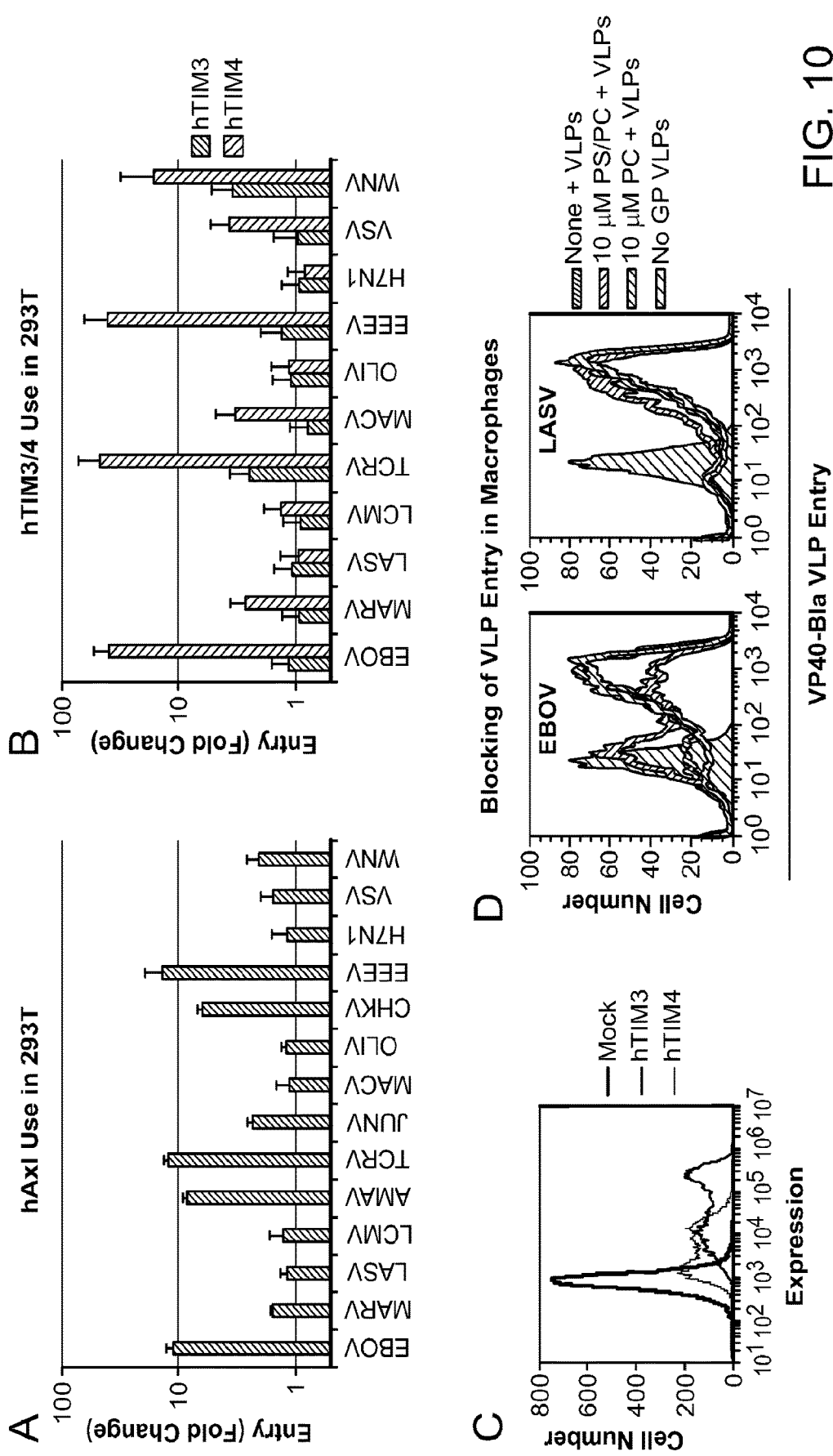

FIGS. 10A-10D depicts other PS-binding receptors similarly promoted entry of hTIM1-using pseudoviruses. FIG. 10A depicts exogenous hAxl usage in 293T cells. 293T cells were transfected with hAxl or hACE2, infected with pseudoviruses or WNV VLPs, both carrying a GFP reporter gene, and infection levels were assessed the following day by measuring GFP expression by flow cytometry. Fold changes in entry were calculated by dividing mean fluorescence intensity observed in hAxl-expressing 293T by those of hACE2-expressing 293T cells. FIG. 10A shows mean+SD from three independent, duplicated experiments. Note that the entry of WNV VLPs is slightly increased by hAxl. FIG. 10B depicts exogenous hTIM3 and hTIM4 use in 293T cells. 293T cells were transfected with plasmids expressing hTIM3, hTIM4 or hACE2, infected with the indicated pseudoviruses or WNV VLPs and infection levels were assessed as in FIG. 10A. Shown are mean+SD from three independent experiments. Note that, unlike hTIM1 and hTIM4, hTIM3 only weakly enhanced infection of TCRV pseudoviruses and WNV VLPs. FIG. 10C depicts that both hTIM3 and hTim4 were expressed efficiently. The same cells as in FIG. 10B were stained with anti-myc tag antibody. FIG. 10C shows representative results of one of three independent experiments. FIG. 10D shows that PS receptors contributed to EBOV VLP entry in macrophages. Mouse peritoneal macrophages plated the previous day were pre-incubated for 30 min at room temperature with medium alone (none) or with liposomes consisting of 50% PS and 50% PC (PS/PC) or PC alone (PC). VP40-Bla VLPs bearing the entry proteins of EBOV, LASV, or no GP (negative control) were then added for a 2 hr infection at 37° C., after which cells were detached, washed, loaded with the Bla substrate CCF2-AM, washed again and analyzed by flow cytometry. Data are representative of two experiments performed in duplicate.

Figure 11:
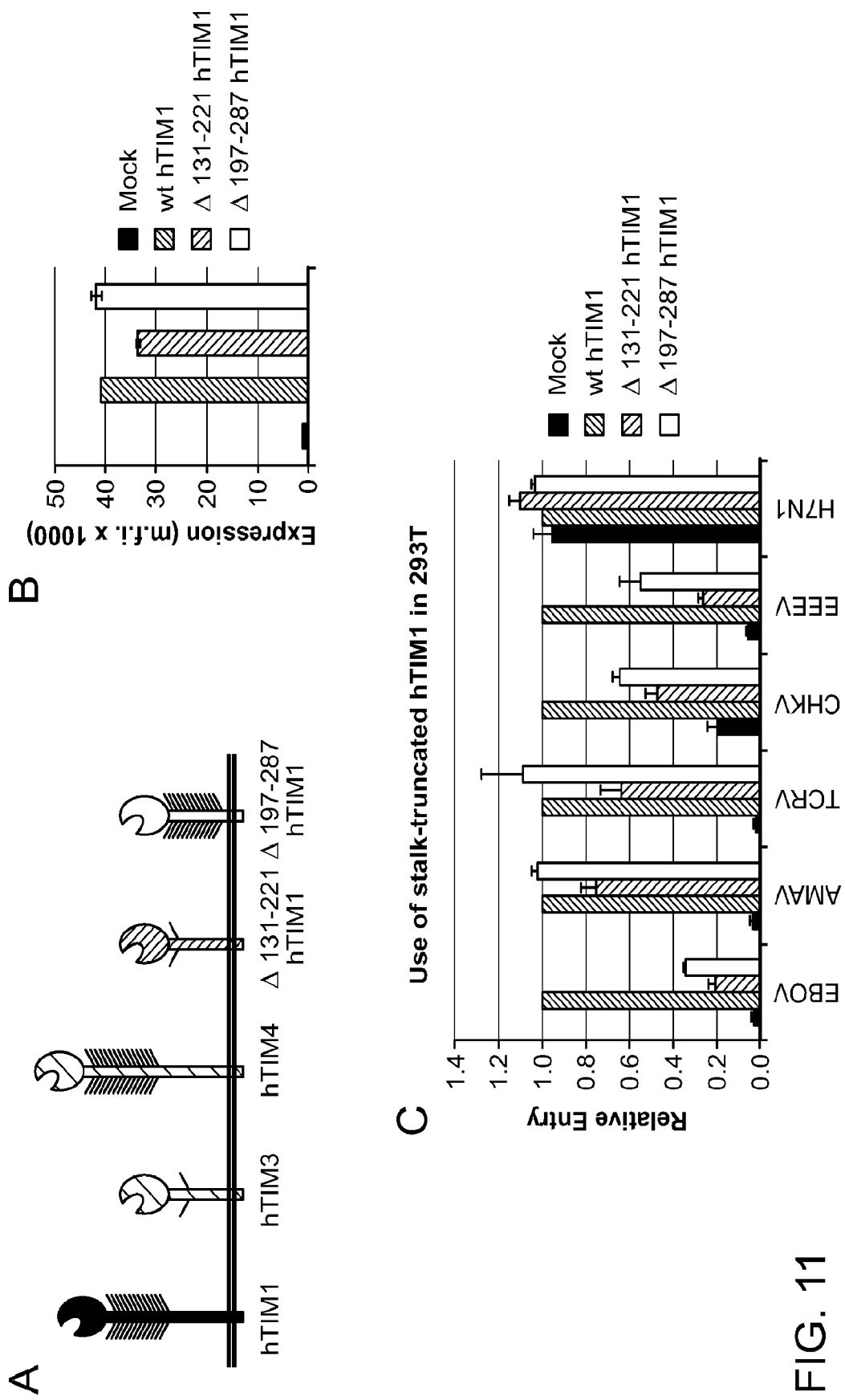

FIGS. 11A-11C depict contribution of stalk length and O-glycans of hTIMs to virus entry. FIG. 11A is a schematic representation of the three human TIM proteins and stalk-truncated hTIM1 variants used in FIGS. 11B-11C. hTIM3 differs from the other TIMs because its stalk is shorter and because it has a dramatically reduced number of 0-glycans [18]. The two truncation variants of hTIM1, A131-221 and A197-287 hTIM1, were made to resemble hTIM3 in stalk length and number of O-glycosylation sites. FIG. 11B depicts expression levels of stalk-truncated and wt hTIM1 were comparable. 293T cells were transfected with plasmids expressing hACE2 (mock), 4131-221 hTIM1, 4197-287 hTIM1 or wt hTIM1. Cells were stained 48 hr. later with the anti-hTIM1 antibody 3D1, which binds the IgV head domain of hTIM1 [21]. Representative results of one of three experiments performed in duplicate are shown. FIG. 11C depicts usage of stalk-truncated hTIM1 variants in 293T cells. The same cells as in FIG. 11B were infected with the indicated pseudoviruses carrying a GFP reporter gene. Infection levels were assessed the following day by flow cytometry and normalized to those of wt hTIM1-expressing cells. FIG. 11C shows representative results of one of three experiments performed in duplicate.

Figure 12:
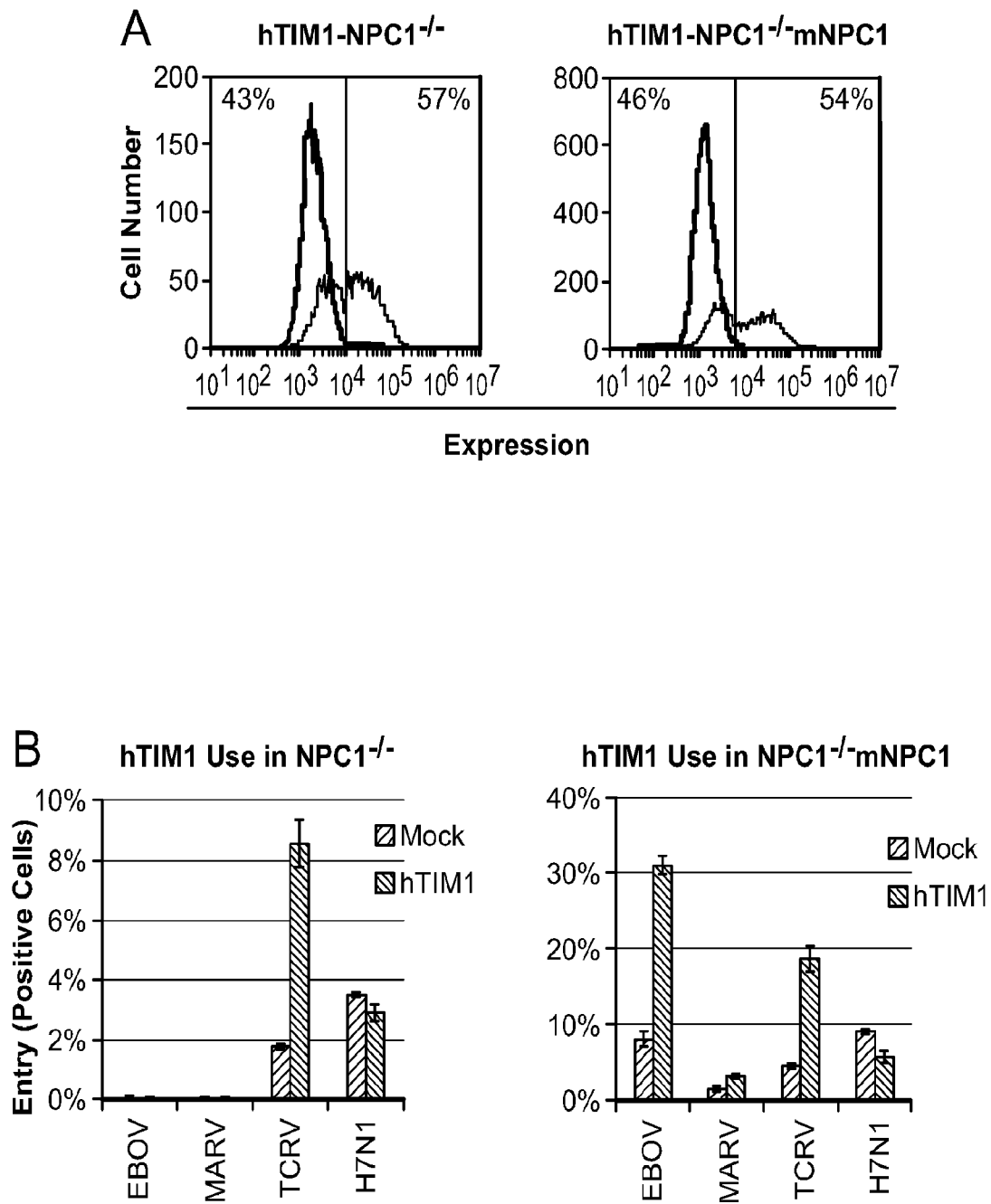

FIGS. 12A and 12B depict hTIM1-mediated EBOV and MARV entry was dependent on the presence of the intracellular receptor NPC1. CHO cells lacking NPC1 (NPC1-/-) and the same cells stably expressing mouse NPC1 (NPC-/-mNPC1) were mock transduced or transduced to express hTIM1. FIG. 12A depicts assessment of cells for hTIM1 expression levels using anti-hTIM1 antibody as in FIG. 1A. FIG. 12B depicts infection of cells for 0.5-1 hr. with EBOV or MARV pseudoviruses, which were concentrated 3-5 fold by ultracentrifugation, or with unconcentrated TCRV or H7N1 pseudoviruses as positive and negative controls for TIM1 use. Infection levels for all viruses were assessed 2 days after infection by measuring GFP expression. Regardless of hTIM1 expression, NPC1-/- cells showed no GFP positive cells with either EBOV or MARV infection when inspected by fluorescence microscopy. FIG. 12B depicts representative results of one of three experiments performed in duplicates.

Figure 13:
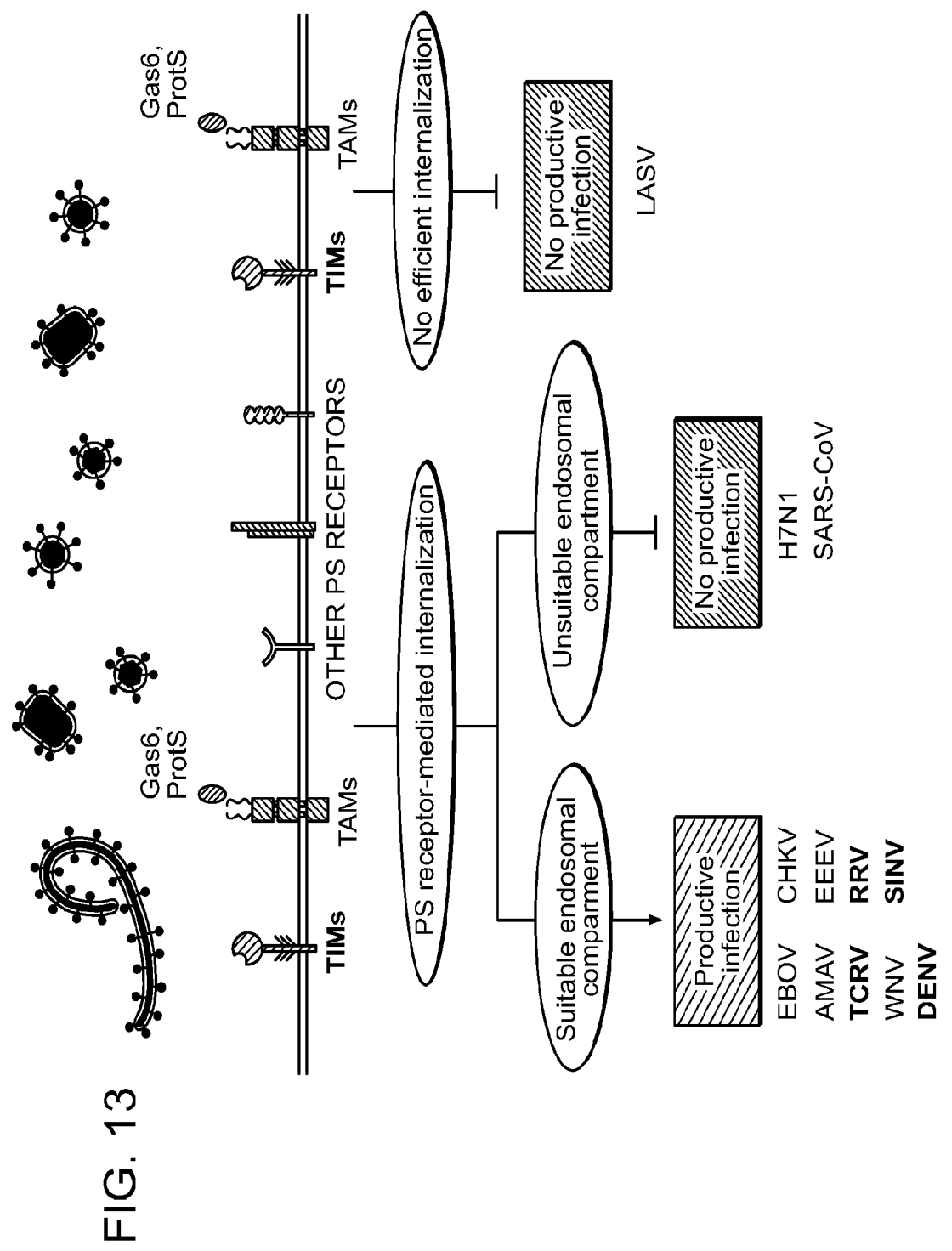

FIG. 13 depicts a model of viral PS receptor usage. Without being bound to a particular theory, human TIM proteins (TIMs) and other PS-binding receptors efficiently, but nonspecifically, promoted internalization of various enveloped viruses. The TAM receptors Axl, Mer and Tyro (TAMs) similarly bind and internalize many viruses, albeit indirectly via the PS-binding bridging proteins Gas6 and/or Protein S (Prot S) in serum [34]. For most viruses PS-dependent internalization results in moderate to strong increase of productive infection. Note that the degree of enhancement will depend on the cellular background in which experiments are performed. However, in the case of other viruses, PS receptor-mediated internalization may lead to a compartment that is not productive for infection. In addition, there is a third class of viruses which is not efficiently bound and/or internalized by PS receptors. The indicated viruses were categorized based on hTIM1 usage and internalization results obtained with pseudoviruses and VLPs (black) or replication-competent viruses (blue). Note that the consequences or efficiency of internalization can vary depending on the PS receptors and their expression levels.

Figure 14:
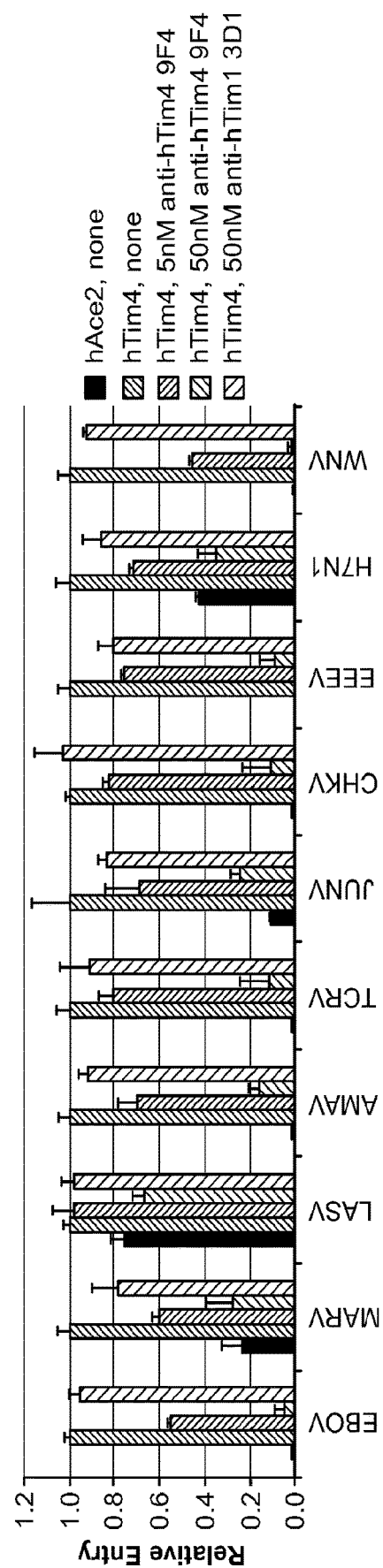

FIG. 14 depicts anti-hTim4 antibody 9F4 blocked the entry of various enveloped viruses. HEK 293T cells were transduced to express hTIM4 or a control receptor (hAce2). Cells were then preincubated for 30 min. at room temperature with medium alone (none), with anti-hTim4 antibody 9F4 or, as a negative control, with antihTim1 antibody 3D1. Then MLV pseudoviruses bearing the entry proteins of the indicated viruses or WNV virus like particles were added for overnight infection in the presence of the respective blocking agents. Infection levels were assessed the following day by flow cytometry.

FIG. 15 depicts TIM1-mFc inhibited the entry of various pseudoviruses. Huh7 cells were preincubated for 30 min at room temperature with medium alone (none), purified TIM1-mFc or purified mIgG (negative control), and incubated overnight at 37° C. with the indicated pseudoviruses in the presence of the respective blocking agents. Infection levels were assessed 48 hr. later by measuring GFP expression and normalized to those of untreated cells. Mean+SD from two independent, duplicate experiments are shown.

DETAILED DESCRIPTION OF THE INVENTION

The present invention provides compositions and methods for the prevention or treatment of a disease or disorder mediated by enveloped viruses (e.g., filoviruses EBOV and MARV; arenaviruses JUNV, MACV, AMAV, and TCRV; alphaviruses EEEV, CHKV, SINV, and RRV; and flaviviruses DENV and WNV).

As reported in detail below, use of anti-TIM1 or TIM4 antibodies, or TIM1- or TIM4-Ig blocked phosphatidylserine-mediated infection of a wide range of enveloped viruses including filoviruses, flaviviruses, arenaviruses, and alphaviruses. Advantageously, the disclosures herein show that the interaction between a wide range of viruses and a wide range of target-cell molecules can be blocked by antibodies to TIM proteins (anti-TIM1 or anti-TIM4) or TIM1- or TIM4-Ig fusion molecules, thus limiting viral infection. Previous reports either showed an incorrect mechanism, and/or focused on individual viruses and other target-cell interactions. The invention is based at least in part on these discoveries.

Viral Entry of Enveloped Viruses

The entry of enveloped viruses is a multi-stage process. Following attachment, some viruses fuse to cells at the plasma membrane, whereas others are internalized through various endocytic routes and, primed by low pH or compartment-resident factors, fuse at the endo/lysosomal membranes. Viruses attach to the cell surface through the binding of their entry glycoproteins (GPs) to specific receptors/coreceptors and also through less specific interactions with various attachment factors [1]. While the distinction between attachment factors and bona fide receptors has not always been carefully made, receptors typically involve necessary, specific, and high-affinity interactions that can prime the viral entry protein for subsequent fusion steps. Attachment factors, in contrast, are typically interchangeable, involve less specific interactions, and serve primarily to localize the virus to its receptor(s) and other cofactors necessary for fusion.

A recent study reported that human TIM1 (hTIM1), a protein previously implicated as a receptor for the non-enveloped hepatitis A virus [2,3,4], also functioned as a receptor for the enveloped viruses Ebola (EBOV) and Marburg (MARV) [5]. In contrast to the present disclosure, this study neither showed the effect of inhibiting TIM1 for a wide range of viruses, nor showed TIM1 effect was through phosphatidylserine binding. In the present disclosure, inhibiting TIM1 significantly inhibited alphavirus, flavivirus, filovirus, and arenavirus viral entry, and moderately inhibited orthomoxyvirus, rhabdovirus, coronavirus viral entry. Thus, hTIM1 is added to the long list of filovirus entry factors, which include 1-integrins [6,7], the folic acid receptor alpha, which was later disputed [8,9,10], the TAM receptors Axl, Mer and Tyro [11], various C-type lectins [12,13,14] and the intracellular receptor Niemann-Pick C1 (NPC1) [15,16,17]. hTIM1 was identified by correlating gene expression patterns of 60 cancer cell lines with their permissiveness to EBOV entry [5].

T-Cell Immunoglobulin and Mucin-Domain Containing Proteins (TIM Proteins)

The T-cell Immunoglobulin and Mucin-domain containing (TIM) protein family comprises three members in humans (hTIM1, 3, and 4) and eight in mice (mTIM1-8) that are implicated in the regulation of innate and adaptive immune responses [18]. Based on expression, functional and structural data hTIM1, 3, and 4 are considered direct orthologs of mTIM1, 3, and 4, respectively [19,20]. The ectodomain of TIM proteins includes an N terminal variable immunoglobulin-like (IgV) domain and a stalk-like mucin domain that varies in length and O-glycosylation [18]. Importantly, the IgV domains of all hTIM proteins contain a high-affinity binding site for PS, a phospholipid constituent of eukaryotic membranes [21,22]. Generally present on the cytosolic side of the plasma membrane lipid bilayer, PS flips to the outer leaflet upon the onset of apoptosis, where it acts as a phagocytic "eat me" signal for professional phagocytes (macrophages and dendritic cells) as well as non-professional phagocytes (e.g., epithelial cells) [23,24,25]. Consistent with a PS receptor function, one important role of TIM proteins is to initiate PS-mediated engulfment of apoptotic cells and debris [21,22,26]. Although this role may be more prominent for TIM3 and TIM4, which are expressed on dendritic cell and macrophage sub-populations [21,22,26,27], TIM1 is known to be expressed on various epithelial cells [5], which can also assume phagocytic roles. TIM1 and TIM3 are further expressed on subsets of activated T-cells, where they act as costimulatory and coinhibitory molecules, respectively [28,29,30].

TIM Proteins and Viral Entry

The results described herein indicate that hTIM1 is an efficient attachment factor for a range of enveloped viruses, and imply that hTIM1 promotes infection by associating with PS on the virions (see e.g., FIG. 13). PS dependency of TIM1 is supported by several independent lines of evidence. First, all pseudoviruses capable of using hTIM1 can also be enhanced by at least one other PS receptor, e.g., hTIM4 or hAxl (FIGS. 10A-10D). Second, a functional, hTIM1 PS-binding domain was an important prerequisite for viral hTIM1 usage (FIGS. 7A-7D). Finally, the interaction between hTIM1 and GP-free virions was sufficient to elicit attachment and internalization, and this internalization was blocked by PS-containing liposomes (FIGS. 7A-7D, 8A, and 8B).

The data described herein are noteworthy and surprising in a few respects. First, the finding that the entry efficiency of a large number of viruses can be enhanced by TIM1 or related receptors indicates that PS receptors play a more prominent role in viral entry than previously appreciated. This may appear difficult to reconcile with structural studies reporting that the membranes of flavi- and alphaviruses are occluded by tightly-arranged viral glycoproteins. However, flavivirus virions often incorporate immature glycoproteins [67], which could lead to gaps in the glycoprotein coat through which PS becomes accessible. The present findings are consistent with another recent report for a role of TIM proteins in flavivirus entry [68]. Second, as described below, the importance of PS receptors in viral entry is underscored by the fact that several viruses are known to initiate infections in PS receptor-rich cells. Finally, because the exposure of PS on virions is likely a common feature of enveloped viruses [32], it is perhaps most surprising that the entry of a number of viruses remains unaffected by TIM1 expression.

Without being bound to a particular theory, there are several explanations for why not every PS receptor supports the entry of every enveloped virus (FIG. 13). First, PS receptor usage could be affected by the endocytic routes of bona fide virus receptors. For example, the six arenaviruses used in FIG. 1C can be divided into three groups with respect to TIM1 use: LASV and LCMV, which use alpha-dystroglycan as their cellular receptor [52] only weakly utilize TIM1; MACV and JUNV whose receptor is transferrin receptor 1 [41,47] use TIM1 with moderate efficiency; and TCRV and AMAV, which lack a known human receptor, utilize TIM1 with exceptionally high efficiency. For TIM1 to enhance infection, the endocytic pathways of TIM1-mediated internalization may need to coincide with those of the primary receptors of these viruses. However, this explanation may not fully describe the clear differences in TIM1 usage among EBOV, MARV, H7N1 and SARS-CoV (FIGS. 1A-1F and 2A-2F), all of which need access to late endosomes/lysosomes for productive infection. A second possibility, suggested by Morizono and colleagues for hAxl, is that high-affinity receptors may render hTIM1 use ineffective for some viruses [34]. While this receptor-affinity hypothesis may explain the lack of TIM1 usage in the case of LASV (FIGS. 1A-1F and 8A), which has a high-affinity receptor, it cannot explain the absence of TIM1 usage for the SARS-CoV SZ isolate with low affinity to hACE2 (FIG. 9). A final possibility is that steric hindrance by individual viral entry proteins may affect TIM1-mediated enhancement. Specifically, long or densely packed entry proteins, which are usually covered with glycans, may prevent PS receptors from reaching PS on the viral membrane. Consistent with this hypothesis, truncated hTIM1 variants and hTIM3, which has a much shorter mucin stalk than hTIM1, were used less efficiently than wt hTIM1 by several pseudoviruses (FIGS. 10A-10D and 11A-11C).

Figure 1E:
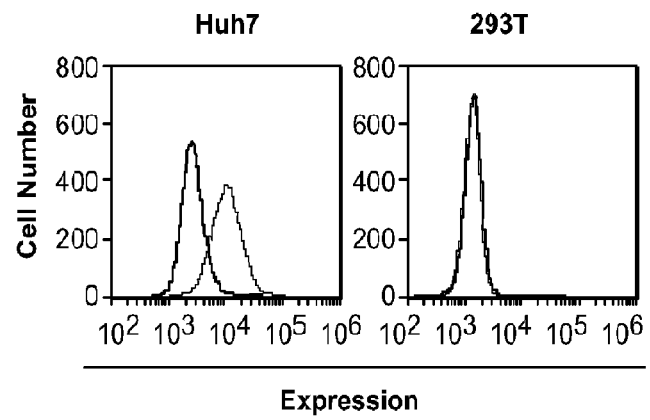

The efficiency with which viruses utilize PS receptors also appears to be dependent on the cellular background. For example, overexpression of hTIM1 had a lesser effect on viral entry in 3T3 compared to 293T cells (FIGS. 1A-1F). This difference may be due to cell-specific expression of various endogenous PS receptors. Consistent with this explanation, 3T3 cells express Axl [53,54], while 293T cells do not [11,34]. In addition, WNV, which does not efficiently utilize Axl (FIG. 10A), was the only virus showing strong TIM1-mediated entry enhancement in 3 T 3 cells (FIG. 1D). This example emphasizes that results obtained with specific cell lines need to be generalized with caution.

One important question concerning viral PS receptor usage is whether PS receptors are sufficient for productive infection or whether virus-specific receptors are still required. TIM1 was unable to enhance the infection of EBOV and MARV pseudoviruses in the absence of the intracellular filovirus entry factor NPC1 (FIGS. 12A and 12B), indicating that TIM1 functions solely as an attachment factor for filoviruses. On the other hand, some viruses were reported to fuse with receptor-free liposomes at low pH [55,56,57], raising the possibility that in a few specific cases PS receptor-mediated internalization may be sufficient for productive infection. Nevertheless, studies using liposomes that are unnaturally enriched with specific lipid components may not accurately represent physiological conditions.

PS receptors form a complementary, widely expressed network of receptors that is characterized by functional rather than structural conservation. These particular features of PS receptors likely contribute to their exploitation by viruses as attachment factors. Notably, several PS receptors, including TIM4, are highly expressed on mammalian macrophages and dendritic cells. These cells play critical roles in the initial stages of infection of filoviruses and flaviviruses in particular [58,59,60], and PS receptors may thus play correspondingly important roles in establishing these infections. PS receptors may be more important still for viruses like DENV, WNV, EEEV and CHKV, which are borne by insect vectors. The role of PS as apoptotic marker is conserved in insects [61], and the membranes of insect cells are generally enriched with anionic phospholipids compared to mammalian cells [62,63]. Thus mosquito-delivered virions may especially benefit from PS receptor-mediated enhancement of infection.

In summary, the results described herein indicate that hTIM1 and related proteins function as attachment factors for a full range of enveloped viruses. hTIM1, hTIM4, hAxl and potentially other PS-binding receptors enhanced the entry of a number of highly divergent viruses. As demonstrated for hTIM1, the enhancement conferred by all of these receptors is likely PS dependent and does not require any viral entry protein. Accordingly, these proteins may not properly be described as viral receptors, although the nature of the viral entry protein clearly impacts the relevance of PS receptors to infection. In some cases, PS receptors may play critical roles in establishing or maintaining an in vivo infection, which could affect disease severity. Thus, as was demonstrated for Pichinde virus and mouse cytomegalovirus [32], the results support the proposal that therapeutic strategies targeting PS and other anionic phospholipids may be broadly effective against a wide range of viruses.

Phospholipids and Viral Entry

Negatively-charged phospholipids like 1,2-diacyl-sn-glycero-3-phospho-L-serine (PS) and or 1,2-diacyl-sn-glycero-3-phosphoethanolamine (PE) have the potential to play a role in mediating virus entry. PS and other anionic phospholipids like PE are exposed on the membranes of various enveloped viruses, including Pichinde virus, vesicular stomatitis virus (VSV) and the intracellular mature virion form of Vaccinia virus [31,32]. This is likely a common feature of most enveloped viruses, as virus-infected cells were shown to overexpress PS on their plasma membranes [31,32,33]. In addition, the entry of pseudoviruses bearing the GPs of Sindbis, Ross River and Baculo virus was enhanced in a PS-dependent manner by the TAM receptor tyrosine kinase Axl [34]. Axl has also been shown to promote EBOV and MARV entry [11]. Finally, an antibody targeting anionic phospholipids effectively rescued rodents from lethal challenges by either Pichinde virus or mouse cytomegalovirus, demonstrating in vivo contribution of anionic phospholipids to the infectivity of these viruses [32].

Because hTIM1 binds PS with high affinity [21] and various viruses contain PS on their virion surfaces [31,32], the possibility that the reported hTIM1-mediated EBOV entry [5] is PS dependent was explored. Furthermore, using pseudoviruses, VLPs, and infectious viruses bearing the entry proteins of 19 viruses from 7 different families, the generality of PS-receptor usage and its underlying mechanisms was investigated. hTIM1 promoted infection by a range of viruses, including members of the Filovirus, flavivirus, alphavirus, and New World arenavirus families, and this enhancement required the PS-binding activity of hTIM1. Additional PS receptors, such as hTIM4 and hAxl enhanced the entry of most hTIM1-using pseudoviruses, and the efficiency of this enhancement largely correlated with that observed with hTIM1.

TIM Polypeptides and Analogs

The invention provides TIM polypeptides (e.g., TIM1, TIM3, TIM4) for inhibiting viral entry.

The amino acid sequence of TIM1 (SEQ ID NO: 1) is provided at GenBank Accession No. AF066592, which is reproduced below:

```
  1 mhpqvvilsl ilhladsvag svkvggeagp svtlpchysg avtsmcwnrg scslftcqng 61 ivwtngthvt yrkdtrykll gdlsrrdvsl tientavsds gvyccrvehr gwfndmkitv 121 sleivppkvt ttpivttvpt vttvrtsttv pttttvpttt vpttmsiptt ttvpttmtvs
```

```
181 tttsvpttts ipttsvpvt ttvstfvppm plprqnhepv atspsspgpa ethpttlqga 241 irreptsspl ysyttdgndt vtessdglwn nnqtqlfleh slltanttkg iyagvcisvl 301 vllallgvii akkyffkkev qqlsvsfssl qikalgnave kevqaedniy ienslyatd
```

TIM1 is a 359-amino acid polypeptide. The nucleotide sequence of human TIM1 (SEQ ID NO: 2) corresponds to GenBank Accession No. JX049978, which is reproduced below:

```
   1 atgcatcctc aagtggtcat cttaagcctc atcctacatc tggcagattc tgtagctggt 61 tctgtaaagg ttggtggaga ggcaggtcca tctgtcacac taccctgcca ctacagtgga 121 gctgtcacat caatgtgctg gaatagaggc tcatgttctc tattcacatg ccaaaatggc 181 attgtctgga ccaatggaac ccacgtcacc tatcggaagg acacacgcta taagctattg 241 ggggaccttt caagaaggga tgtctctttg accatagaaa atacagctgt gtctgacagt 301 ggcgtatatt gttgccgtgt tgagcaccgt gggtggttca atgacatgaa aatcaccgta 361 tcattggaga ttgtgccacc caaggtcacg actactccaa ttgtcacaac tgttccaacc 421 gtcacgactg ttcgaacgag caccactgtt ccaacgacaa cgactgttcc aacgacaact 481 gttccaacaa caatgagcat tccaacgaca acgactgttc cgacgacaat gactgtttca 541 acgacaacga gcgttccaac gacaacgagc attccaacaa caacaagtgt tccagtgaca 601 acaacggtct tacctttgt tcctccaatg cctttgccca ggcagaacca tgaaccagta 661 gccacttcac catcttcacc tcagccagca gaaacccacc tacgacact gcagggagca 721 ataaggagag aacccaccag ctcaccattg tactcttaca aacagatgg gaatgacacc 781 gtgacagagt cttcagatgg cctttggaat aacaatcaaa ctcaactgtt cctagaacat 841 agtctactga cggccaatac cactaaagga atctatgctg gagtctgtat ttctgtcttg 901 gtgcttcttg ctcttttggg tgtcatcatt gccaaaaagt atttcttcaa aaaggaggtt 961 caacaactaa gtgtttcatt tagcagcctt caaattaaag ctttgcaaaa tgcagttgaa 1021 aaggaagtcc aagcagaaga caatatctac attgagaata gtctttatgc cacggattaa
```

The amino acid sequence of TIM3 (SEQ ID NO: 3) is provided at GenBank Accession No. AF066593, which is reproduced below:

```
   1 mfshlpfdcv llllllltr sseveyraev gqnaylpcfy tpaapgnlvp vcwgkgacpv 61 fecgnvvlrt derdvnywts rywlngdfrk gdvsltienv tladsgiycc riqipgimnd 121 ekfnlklvik pakvtpaptl qrdftaafpr mlttrghgpa etqtlgslpd initqistla 181 nelrdsrlan dlrdsgatir igiyigagic aglalalifg alifkwyshs kekignlsli 241 slanlppsgl anavaegirs eeniytieen vyeveepney ycyvssrqqp sqplgcrfam 301 p
```

TIM3 is a 301-amino acid polypeptide. The nucleotide sequence of human TIM3 (SEQ ID NO: 4) corresponds to GenBank Accession No. JX049979, which is reproduced below:

```
   1 atgttttcac atcttccctt tgactgtgtc ctgctgctgc tgctgctact acttacaagg 61 tcctcagaag tggaatacag agcggaggtc ggtcagaatg cctatctgcc ctgcttctac 121 accccagccg ccccagggaa cctcgtgccc gtctgctggg gcaaggagc ctgtcctgtg
```

-continued

```
181 tttgaatgtg gcaacgtggt gctcaggact gatgaaaggg atgtgaatta ttggacatcc 241 agatactggc taaatgggga tttccgcaaa ggagatgtgt ccctgaccat agagaatgtg 301 actctagcag acagtgggat ctactgctgc cggatccaaa tcccaggcat aatgaatgat 361 gaaaaattta acctgaagtt ggtcatcaaa ccagccaagg tcacccctgc accgactctg 421 cagagagact tcactgcagc ctttccaagg atgcttacca ccaggggaca tggcccagca 481 gagacacaga cactggggag cctccctgat ataaatctaa cacaaatatc acattggcc 541 aatgagttac gggactctag attggccaat gacttacggg actctggagc aaccatcaga 601 ataggcatct acatcggagc agggatctgt gctgggctgg ctctggctct tatcttcggc 661 gctttaattt tcaaatggta ttctcatagc aaagagaaga tacagaattt aagcctcatc 721 tctttggcca acctccctcc ctcaggattg gcaaatgcag tagcagaggg aattcgctca 781 gaagaaaaca tctataccat gaagagaac gtatatgaag tggaggagcc caatgagtat 841 tattgctatg tcagcagcag gcagcaaccc tcacaacctt tgggttgtcg ctttgcaatg 901 ccatag
```

The amino acid sequence of TIM4 (SEQ ID NO: 5) is provided at NCBI Accession No. NP_612388, which is reproduced below:

```
  1 mskeplilwl miefwwlylt pvtsetvvte vlghrvtlpc lysswshnsn smcwgkdqcp 61 ysgckealir tdgmrvtsrk sakyrlqgti prgdvsltil npsesdsgvy ccrievpgwf 121 ndvkinvrln lqrastthr tattttrrtt tsptttrqm tttpaalptt vvttpdlttg 181 tplqmttiav fttantclsl tpstlpeeat glltpepske gpiltaeset vlpsdswssv 241 estsadtvll tskeskvwdl pstshvsmwk tsdsysspqp gasdtavpeq nkttktgqmd 301 gipmsmknem pisqllmiia pslgfvlfal fvafllrgkl metycsqkht rldyigdskn 361 vlndvqhgre dedglftl
```

TIM4 is a 378-amino acid polypeptide. The nucleotide sequence of human TIM4 (SEQ ID NO: 6) corresponds to Genbank Accession No. JX049980, which is reproduced below:

```
  1 atgtccaaag aacctctcat tctctggctg atgattgagt tttggtggct ttacctgaca 61 ccagtcactt cagagactgt tgtgacggag gttttgggtc accgggtgac tttgccctgt 121 ctgtactcat cctggtctca aacagcaac agcatgtgct ggggggaaaga ccagtgcccc 181 tactccggtt gcaaggaggc gctcatccgc actgatggaa tgagggtgac ctcaagaaag 241 tcagcaaaat atagacttca ggggactatc ccgagaggtg atgtctcctt gaccatctta 301 aaccccagtg aaagtgacag cggtgtgtac tgctgccgca tagaagtgcc tggctggttc 361 aacgatgtaa agataaacgt gcgcctgaat ctacagagag cctcaacaac cacgcacaga 421 acagcaacca ccaccacacg cagaacaaca acaagcc caccaccac ccgacaaatg 481 acaacaaccc cagctgcact tccaacaaca gtcgtgacca caccgatct cacaaccgga 541 acaccactcc agatgacaac cattgccgtc ttcacaacag caaacacgtg cctttcacta 601 accccaagca cccttccgga ggaagccaca ggtcttctga ctcccgagcc ttctaaggaa 661 gggcccatcc tcactgcaga atcagaaact gtcctcccca gtgattcctg gagtagtgct 721 gagtctactt ctgctgacac tgtcctgctg acatccaaag agtccaaagt ttgggatctc
```

```
 781 ccatcaacat cccacgtgtc aatgtggaaa acgagtgatt ctgtgtcttc tcctcagcct 841 ggagcatctg atacagcagt tcctgagcag aacaaaacaa caaaaacagg acagatggat 901 ggaataccca tgtcaatgaa gaatgaaatg cccatctccc aactactgat gatcatcgcc 961 ccctccttgg gatttgtgct cttcgcattg tttgtggcgt ttctcctgag agggaaactc 1021 atggaaacct attgttcgca gaaacacaca aggctagact acattggaga tagtaaaaat 1081 gtcctcaatg acgtgcagca tggaagggaa gacgaagacg gcctttttac cctctaa
```

In one embodiment, the invention provides methods for optimizing TIM polypeptide amino acid sequence or nucleic acid sequence by producing an alteration. Such alterations may include certain mutations, deletions, insertions, or post-translational modifications. The invention further includes analogs of any naturally-occurring polypeptide of the invention. Analogs can differ from the naturally-occurring the polypeptide of the invention by amino acid sequence differences, by post-translational modifications, or by both. Analogs of the invention will generally exhibit at least 85%, more preferably 90%, and most preferably 95% or even 99% identity with all or part of a naturally-occurring amino, acid sequence of the invention. The length of sequence comparison is at least 10, 13, 15 amino acid residues, preferably at least 25 amino acid residues, and more preferably more than 35 amino acid residues.

Alterations of a TIM polypeptide include but are not limited to site-directed, random point mutagenesis, homologous recombination (DNA shuffling), mutagenesis using uracil containing templates, oligonucleotide-directed mutagenesis, phosphorothioate-modified DNA mutagenesis, mutagenesis using gapped duplex DNA or the like. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, e.g., involving chimeric constructs, is also included in the present invention. In one embodiment, mutagenesis can be guided by known information of the naturally occurring molecule or altered or mutated naturally occurring molecule, e.g., sequence, sequence comparisons, physical properties, crystal structure or the like.

In one embodiment, the invention provides polypeptide variants that differ from a reference polypeptide. The term "variant" refers to an amino acid sequence that is altered by one or more amino acids with respect to a reference sequence. The variant can have "conservative" changes, wherein a substituted amino acid has similar structural or chemical properties, e.g., replacement of leucine with isoleucine. Alternatively, a variant can have "nonconservative" changes, e.g., replacement of a glycine with a tryptophan. Analogous minor variations can also include amino acid deletion or insertion, or both. Guidance in determining which amino acid residues can be substituted, inserted, or deleted without eliminating biological or immunological activity can be found using computer programs well known in the art, for example, DNASTAR software. Desirably, variants show substantial biological activity. In one embodiment, a protein variant elicits an antibody response when administered to a subject.

Natural variants can occur due to mutations in the proteins. These mutations may lead to antigenic variability within individual groups of infectious agents. Thus, a person infected with a particular strain develops antibody against that virus, as newer virus strains appear, the antibodies against the older strains no longer recognize the newer virus and reinfection can occur. The invention encompasses all antigenic and genetic variability of proteins from infectious agents.

Again, in an exemplary approach to determining the degree of identity, a BLAST program may be used, with a probability score between $e^{-3}$ and $e^{-100}$ indicating a closely related sequence. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring polypeptides of the invention by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, Molecular Cloning: A Laboratory Manual (2d ed.), CSH Press, 1989, or Ausubel et al., supra). Also included are cyclized peptides, molecules, and analogs which contain residues other than L-amino acids, e.g., D-amino acids or non-naturally occurring or synthetic amino acids, e.g., .beta. or .gamma. amino acids.

In addition to full-length polypeptides, the invention also includes fragments of any one of the polypeptides of the invention. As used herein, the term "a fragment" means at least 5, 10, 13, or 15. In other embodiments a fragment is at least 20 contiguous amino acids, at least 30 contiguous amino acids, or at least 50 contiguous amino acids, and in other embodiments at least 60 to 80 or more contiguous amino acids. Fragments of the invention can be generated by methods known to those skilled in the art or may result from normal protein processing (e.g., removal of amino acids from the nascent polypeptide that are not required for biological activity or removal of amino acids by alternative mRNA splicing or alternative protein processing events).

Non-protein analogs having a chemical structure designed to mimic TIM polypeptide functional activity can be administered according to methods of the invention. Methods of analog design are well known in the art, and synthesis of analogs can be carried out according to such methods by modifying the chemical structures such that the resultant analogs exhibit viral inhibitory activity. These chemical modifications include, but are not limited to, substituting alternative R groups and varying the degree of saturation at specific carbon atoms of the native TIM polypeptide molecule. Preferably, the analogs are relatively resistant to in vivo degradation, resulting in a more prolonged therapeutic effect upon administration. Assays for measuring functional activity include, but are not limited to, those described in the Examples below.

Polypeptide Expression

In general, VLPs comprising one or more viral polypeptides of the invention may be produced by transfection of a suitable host cell with all or part of a polypeptide-encoding nucleic acid molecule or fragment thereof in a suitable expression vehicle.

Those skilled in the field of molecular biology will understand that any of a wide variety of expression systems may be used to provide the recombinant protein. The precise host cell used is not critical to the invention. A polypeptide of the invention may be produced in a prokaryotic host (e.g., *E. coli*) or in a eukaryotic host (e.g., *Saccharomyces cerevisiae*, insect cells, e.g., Sf21 cells, or mammalian cells, e.g., NIH 3T3, HeLa, COS cells). Such cells are available from a wide range of sources (e.g., the American Type Culture Collection, Rockland, Md.; also, see, e.g., Ausubel et al., supra). Non limiting examples of insect cells are, *Spodoptera frugiperda* (Sf) cells, e.g., Sf9, Sf21, *Trichoplusia ni* cells, e.g., High Five cells, and *Drosophila* S2 cells. Examples of fungi (including yeast) host cells are *S. cerevisiae*, *Kluyveromyces lactis* (*K lactis*), species of *Candida* including *C. albicans* and *C. glabrata*, *Aspergillus nidulans*, *Schizosaccharomyces pombe* (*S. pombe*), *Pichia pastoris*, and *Yarrowia lipolytica*. Examples of mammalian cells are COS cells, baby hamster kidney cells, mouse L cells, LNCaP cells, Chinese hamster ovary (CHO) cells, human embryonic kidney (HEK) cells, African green monkey cells, CV1 cells, HeLa cells, MDCK cells, Vero and Hep-2 cells. *Xenopus laevis* oocytes, or other cells of amphibian origin, may also be used. Prokaryotic host cells include bacterial cells, for example, *E. coli*, *B. subtilis*, and mycobacteria.

Methods of cloning said proteins are known in the art. For example, the gene encoding a specific enveloped virus protein can be isolated by RT-PCR from polyadenylated mRNA extracted from cells which had been infected with said virus. The resulting product gene can be cloned as a DNA insert into a vector. The term "vector" refers to the means by which a nucleic acid can be propagated and/or transferred between organisms, cells, or cellular components. Vectors include plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. In many, but not all, common embodiments, the vectors of the present invention are plasmids or bacmids.

The invention further provides nucleotides that encode proteins, including chimeric molecules, cloned into an expression vector that can be expressed in a cell that provides for the formation of VLPs. An "expression vector" is a vector, such as a plasmid, that is capable of promoting expression, as well as replication of a nucleic acid incorporated therein. Typically, the nucleic acid molecule to be expressed is "operably linked" to a promoter and/or enhancer, and is subject to transcription regulatory control by the promoter and/or enhancer.

The method of transformation or transfection and the choice of expression vehicle will depend on the host system selected. Transformation and transfection methods are described, e.g., in Ausubel et al. (supra); expression vehicles may be chosen from those provided, e.g., in Cloning Vectors: A Laboratory Manual (P. H. Pouwels et al., 1985, Supp. 1987).

A variety of expression systems exist for the production of the polypeptides of the invention. Expression vectors useful for producing such polypeptides include, without limitation, chromosomal, episomal, and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof.

Constructs and/or vectors provided herein comprise polynucleotides of enveloped viruses that encode structural polypeptides, including envelope proteins, matrix proteins, or capsid proteins or portions thereof as described herein. The vector may be, for example, a phage, plasmid, viral, or retroviral vector. The constructs and/or vectors that comprise the nucleotides should be operatively linked to an appropriate promoter, such as the CMV promoter, phage lambda PL promoter, the *E. coli* lac, phoA and tac promoters, the SV40 early and late promoters, and promoters of retroviral LTRs are non-limiting examples. Other suitable promoters will be known to the skilled artisan depending on the host cell and/or the rate of expression desired. The expression constructs will further contain sites for transcription initiation, termination, and, in the transcribed region, a ribosome-binding site for translation. The coding portion of the transcripts expressed by the constructs will preferably include a translation initiating codon at the beginning and a termination codon appropriately positioned at the end of the polypeptide to be translated.

Expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Among vectors preferred are virus vectors, such as baculovirus, poxvirus (e.g., vaccinia virus, avipox virus, canarypox virus, fowlpox virus, raccoonpox virus, swinepox virus, etc.), adenovirus (e.g., canine adenovirus), herpesvirus, and retrovirus. Other vectors that can be used with the invention comprise vectors for use in bacteria, which comprise pQE70, pQE60 and pQE-9, pBluescript vectors, Phagescript vectors, pNH8A, pNH16a, pNH18A, pNH46A, ptrc99a, pKK223-3, pKK233-3, pDR540, pRIT5. Among preferred eukaryotic vectors are pFastBac1 pWINEO, pSV2CAT, pOG44, pXT1 and pSG, pSVK3, pBPV, pMSG, and pSVL. Other suitable vectors will be readily apparent to the skilled artisan.

Recombinant constructs can be prepared and used to transfect, infect, or transform and can express viral proteins, including those described herein, into eukaryotic cells and/or prokaryotic cells. Thus, the invention provides for host cells which comprise a vector (or vectors) that contain nucleic acids which code for genes of enveloped viruses, including envelope proteins, matrix proteins, or capsid proteins, or portions thereof, in said host cell under conditions which allow the formation of VLPs.

In one embodiment, said vector is a recombinant baculovirus. In another embodiment, said recombinant baculovirus is transfected into an insect cell. In a preferred embodiment, said cell is an insect cell. In another embodiment, said insect cell is a Sf9 cell.

In another embodiment, said vector and/or host cell comprises nucleotides that encode enveloped virus genes genes, including capsid, envelope, matrix proteins, or portions thereof as described herein. In another embodiment, said vector and/or host cell consists essentially of alphavirus, flavivirus, filovirus, or arenavirus capsid, envelope, matrix proteins, or portions thereof as described herein. These vector and/or host cell may contain additional cellular constituents such as cellular proteins, baculovirus proteins, lipids, carbohydrates etc.

One particular bacterial expression system for polypeptide production is the *E. coli* pET expression system (Novagen, Inc., Madison, Wis.). According to this expression system, DNA encoding a polypeptide is inserted into a pET vector in an orientation designed to allow expression. Since the gene encoding such a polypeptide is under the control of the T7 regulatory signals, expression of the polypeptide is achieved by inducing the expression of T7 RNA polymerase in the host cell. This is typically achieved using host strains that express T7 RNA polymerase in response to IPTG induction. Once produced, a recombinant polypeptide is then isolated according to standard methods known in the art, for example, those described herein.

Another bacterial expression system for polypeptide production is the pGEX expression system (Pharmacia). This system employs a GST gene fusion system that is designed for high-level expression of genes or gene fragments as fusion proteins with rapid purification and recovery of functional gene products. The protein of interest is fused to the carboxyl terminus of the glutathione S-transferase protein from *Schistosoma japonicum* and is readily purified from bacterial lysates by affinity chromatography using Glutathione Sepharose 4B. Fusion proteins can be recovered under mild conditions by elution with glutathione. Cleavage of the glutathione S-transferase domain from the fusion protein is facilitated by the presence of recognition sites for site-specific proteases upstream of this domain. For example, proteins expressed in pGEX-2T plasmids may be cleaved with thrombin; those expressed in pGEX-3X may be cleaved with factor Xa.

Once a recombinant polypeptide of the invention is expressed, it is isolated, e.g., using affinity chromatography. In one example, an antibody (e.g., produced as described herein) raised against a polypeptide of the invention may be attached to a column and used to isolate the recombinant polypeptide. Lysis and fractionation of polypeptide-harboring cells prior to affinity chromatography may be performed by standard methods (see, e.g., Ausubel et al., supra).

Once isolated, the recombinant protein can, if desired, be further purified, e.g., by high performance liquid chromatography (see, e.g., Fisher, Laboratory Techniques In Biochemistry and Molecular Biology, eds., Work and Burdon, Elsevier, 1980). Polypeptides of the invention, particularly short peptide fragments, can also be produced by chemical synthesis (e.g., by the methods described in Solid Phase Peptide Synthesis, 2nd ed., 1984 The Pierce Chemical Co., Rockford, Ill.). These general techniques of polypeptide expression and purification can also be used to produce and isolate useful peptide fragments or analogs (described herein).

Inhibitory Nucleic Acids

Inhibitory nucleic acid molecules are those oligonucleotides that selectively inhibit the expression or activity of a TIM protein (e.g., TIM1, TIM3, TIM4). Such oligonucleotides include single and double stranded nucleic acid molecules (e.g., DNA, RNA, and analogs thereof) that are complementary to or that bind a nucleic acid molecule that encodes a TIM polypeptide (e.g., antisense molecules, RNAi, siRNA, shRNA) as well as nucleic acid molecules that bind directly to a TIM polypeptide to modulate its biological activity (e.g., aptamers).

siRNA

Short twenty-one to twenty-five nucleotide double-stranded RNAs are effective at down-regulating gene expression (Zamore et al., Cell 101: 25-33; Elbashir et al., Nature 411: 494-498, 2001, hereby incorporated by reference). The therapeutic effectiveness of an siRNA approach in mammals was demonstrated in vivo by McCaffrey et al. (Nature 418: 38-39.2002).

Given the sequence of a target gene, siRNAs may be designed to inactivate that gene.

Such siRNAs, for example, could be administered directly to an affected tissue, or administered systemically. The nucleic acid sequence of TIM polypeptide (e.g., TIM1, TIM3, TIM4) gene can be used to design small interfering RNAs (siRNAs). The 21 to 25 nucleotide siRNAs may be used, for example, as therapeutics to treat radiation exposure or a disorder thereof.

The inhibitory nucleic acid molecules of the present invention may be employed as double-stranded RNAs for RNA interference (RNAi)-mediated knock-down of TIM polypeptide expression. RNAi is a method for decreasing the cellular expression of specific proteins of interest (reviewed in Tuschl, Chembiochem 2:239-245, 2001; Sharp, Genes & Devel. 15:485-490, 2000; Hutvagner and Zamore, Curr. Opin. Genet. Devel. 12:225-232, 2002; and Hannon, Nature 418:244-251, 2002). The introduction of siRNAs into cells either by transfection of dsRNAs or through expression of siRNAs using a plasmid-based expression system is increasingly being used to create loss-of-function phenotypes in mammalian cells.

Ribozymes

Catalytic RNA molecules or ribozymes that include an antisense TIM polypeptide (TIM', TIM3, TIM4) sequence of the present invention can be used to inhibit expression of a TIM nucleic acid molecule or polypeptide in vivo. The inclusion of ribozyme sequences within antisense RNAs confers RNA-cleaving activity upon them, thereby increasing the activity of the constructs. The design and use of target RNA-specific ribozymes is described in Haseloff et al., Nature 334:585-591. 1988, and U.S. Patent Application Publication No. 2003/0003469 A1, each of which is incorporated by reference.

Accordingly, the invention also features a catalytic RNA molecule that includes, in the binding arm, an antisense RNA having between eight and nineteen consecutive nucleobases. In preferred embodiments of this invention, the catalytic nucleic acid molecule is formed in a hammerhead or hairpin motif. Examples of such hammerhead motifs are described by Rossi et al., Aids Research and Human Retroviruses, 8:183, 1992. Example of hairpin motifs are described by Hampel et al., "RNA Catalyst for Cleaving Specific RNA Sequences," filed Sep. 20, 1989, which is a continuation-in-part of U.S. Ser. No. 07/247,100 filed Sep. 20, 1988, Hampel and Tritz, Biochemistry, 28:4929, 1989, and Hampel et al., Nucleic Acids Research, 18: 299, 1990. These specific motifs are not limiting in the invention and those skilled in the art will recognize that all that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule.

shRNA

Small hairpin RNAs consist of a stem-loop structure with optional 3' UU-overhangs. While there may be variation, stems can range from 21 to 31 bp (desirably 25 to 29 bp), and the loops can range from 4 to 30 bp (desirably 4 to 23 bp). In one embodiment of the invention, the shRNA molecule is made that includes between eight and twenty-one consecutive nucleobases of a TIM polypeptide (e.g., TIM1, TIM3, TIM 4) gene.

For expression of shRNAs within cells, plasmid vectors containing either the polymerase III H1-RNA or U6 promoter, a cloning site for the stem-looped RNA insert, and a 4-5-thymidine transcription termination signal can be employed (e.g., pGeneClip Neomycin Vector; Promega Corporation). The Polymerase III promoters generally have well-defined initiation and stop sites and their transcripts lack poly(A) tails. The termination signal for these promoters is defined by the polythymidine tract, and the transcript is typically cleaved after the second uridine. Cleavage at this position generates a 3' UU overhang in the expressed shRNA, which is similar to the 3' overhangs of synthetic siRNAs.

For expression of shRNAs within cells, plasmid vectors containing either the polymerase III H1-RNA or U6 promoter, a cloning site for the stem-looped RNA insert, and a 4-5-thymidine transcription termination signal can be employed. The Polymerase III promoters generally have well-defined initiation and stop sites and their transcripts lack poly(A) tails. The termination signal for these promoters is defined by the polythymidine tract, and the transcript is typically cleaved after the second uridine. Cleavage at this position generates a 3' UU overhang in the expressed shRNA, which is similar to the 3' overhangs of synthetic siRNAs. Additional methods for expressing the shRNA in mammalian cells are described in the references cited above.

Oligonucleotides and Other Nucleobase Oligomers

At least two types of oligonucleotides induce the cleavage of RNA by RNase H: polydeoxynucleotides with phosphodiester (PO) or phosphorothioate (PS) linkages. Although 2'-OMe-RNA sequences exhibit a high affinity for RNA targets, these sequences are not substrates for RNase H. A desirable oligonucleotide is one based on 2'-modified oligonucleotides containing oligodeoxynucleotide gaps with some or all internucleotide linkages modified to phosphorothioates for nuclease resistance. The presence of methylphosphonate modifications increases the affinity of the oligonucleotide for its target RNA and thus reduces the $IC_{50}$. This modification also increases the nuclease resistance of the modified oligonucleotide. It is understood that the methods and reagents of the present invention may be used in conjunction with any technologies that may be developed, including covalently-closed multiple antisense (CMAS) oligonucleotides (Moon et al., Biochem J. 346:295-303, 2000; PCT Publication No. WO 00/61595), ribbon-type antisense (RiAS) oligonucleotides (Moon et al., J. Biol. Chem. 275: 4647-4653, 2000; PCT Publication No. WO 00/61595), and large circular antisense oligonucleotides (U.S. Patent Application Publication No. US 2002/0168631 A1).

As is known in the art, a nucleoside is a nucleobase-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric structure can be further joined to form a circular structure; open linear structures are generally preferred. Within the oligonucleotide structure, the phosphate groups are commonly referred to as forming the backbone of the oligonucleotide. The normal linkage or backbone of RNA and DNA is a 3' to 5' phosphodiester linkage.

Specific examples of preferred nucleobase oligomers useful in this invention include oligonucleotides containing modified backbones or non-natural internucleoside linkages. As defined in this specification, nucleobase oligomers having modified backbones include those that retain a phosphorus atom in the backbone and those that do not have a phosphorus atom in the backbone. For the purposes of this specification, modified oligonucleotides that do not have a phosphorus atom in their internucleoside backbone are also considered to be nucleobase oligomers.

Nucleobase oligomers that have modified oligonucleotide backbones include, for example, phosphorothioates, chiral phosphorothioates, phosphorodithioates, phosphotriesters, aminoalkyl-phosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriest-ers, and boranophosphates having normal 3'-5' linkages, 2'-5' linked analogs of these, and those having inverted polarity, wherein the adjacent pairs of nucleoside units are linked 3'-5' to 5'-3' or 2'-5' to 5'-2'. Various salts, mixed salts and free acid forms are also included. Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Nucleobase oligomers having modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Representative United States patents that teach the preparation of the above oligonucleotides include, but are not limited to, U.S. Pat. Nos. 5,034, 506; 5,166,315; 5,185,444; 5,214,134; 5,216,141; 5,235, 033; 5,264,562; 5,264,564; 5,405,938; 5,434,257; 5,466, 677; 5,470,967; 5,489,677; 5,541,307; 5,561,225; 5,596, 086; 5,602,240; 5,610,289; 5,602,240; 5,608,046; 5,610, 289; 5,618,704; 5,623,070; 5,663,312; 5,633,360; 5,677, 437; and 5,677,439, each of which is herein incorporated by reference.

In other nucleobase oligomers, both the sugar and the internucleoside linkage, i.e., the backbone, are replaced with novel groups. The nucleobase units are maintained for hybridization with a nucleic acid molecule encoding a p75/TNF-α receptor or p55/TNF-α receptor. One such nucleobase oligomer, is referred to as a Peptide Nucleic Acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Methods for making and using these nucleobase oligomers are described, for example, in "Peptide Nucleic Acids: Protocols and Applications" Ed. P. E. Nielsen, Horizon Press, Norfolk, United Kingdom, 1999. Representative United States patents that teach the preparation of PNAs include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

In particular embodiments of the invention, the nucleobase oligomers have phosphorothioate backbones and nucleosides with heteroatom backbones, and in particular —$CH_2$—NH—O—$CH_2$—, —$CH_2$—N($CH_3$)—O—$CH_2$— (known as a methylene (methylimino) or MMI backbone), —$CH_2$—O—N($CH_3$)—$CH_2$—, —$CH_2$—N($CH_3$)—N($CH_3$)—$CH_2$—, and —O—N($CH_3$)—$CH_2$—$CH_2$—. In other embodiments, the oligonucleotides have morpholino backbone structures described in U.S. Pat. No. 5,034,506.

Nucleobase oligomers may also contain one or more substituted sugar moieties. Nucleobase oligomers comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl, and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_n$$CH_3$, O($CH_2$)$_n$O$CH_3$, O($CH_2$)$_n$$NH_2$, O($CH_2$)$_n$$CH_3$, O($CH_2$)$_n$O$NH_2$, and O($CH_2$)$_n$ON[($CH_2$)$_n$$CH_3$)]$_2$, where n and m are from 1 to about 10. Other preferred nucleobase oligomers include one of the following at the 2' position: $C_1$ to $C_{10}$ lower alkyl, substituted lower alkyl, alkaryl, aralkyl, O-alkaryl, or O-aralkyl, SH, $SCH_3$, OCN, Cl, Br, CN, $CF_3$, $OCF_3$, $SOCH_3$, $SO_2CH_3$, $ONO_2$, $NO_2$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of a nucleobase oligomer, or a group for improving the pharmacodynamic properties of an nucleobase oligomer, and other substituents having similar properties. Preferred modifications are 2'-O-methyl and 2'-methoxyethoxy (2'-O—$CH_2CH_2OCH_3$, also known as 2'-O-(2-methoxyethyl) or 2'-MOE). Another desirable modification is 2'-dimethylaminooxyethoxy (i.e., O($CH_2$)$_2$ON($CH_3$)$_2$), also known as 2'-DMAOE. Other modifications include, 2'-aminopropoxy (2'-O$CH_2CH_2CH_2NH_2$) and 2'-fluoro (2'-F). Similar modifications may also be made at other positions on an oligonucleotide or other nucleobase oligomer, particularly the 3' position of the sugar on the 3' terminal nucleotide or in 2'-5' linked oligonucleotides and the 5' position of 5' terminal nucleotide. Nucleobase oligomers may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

Nucleobase oligomers may also include nucleobase modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases, such as 5-methylcytosine (5-me-C), 5-hydroxymethyl cytosine, xanthine, hypoxanthine, 2-aminoadenine, 6-methyl and other alkyl derivatives of adenine and guanine; 2-propyl and other alkyl derivatives of adenine and guanine; 2-thiouracil, 2-thiothymine and 2-thiocytosine; 5-halouracil and cytosine; 5-propynyl uracil and cytosine; 6-azo uracil, cytosine and thymine; 5-uracil (pseudouracil); 4-thiouracil; 8-halo, 8-amino, 8-thiol, 8-thioalkyl, 8-hydroxyl and other 8-substituted adenines and guanines; 5-halo (e.g., 5-bromo), 5-trifluoromethyl and other 5-substituted uracils and cytosines; 7-methylguanine and 7-methyladenine; 8-azaguanine and 8-azaadenine; 7-deazaguanine and 7-deazaadenine; and 3-deazaguanine and 3-deazaadenine. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are particularly useful for increasing the binding affinity of an antisense oligonucleotide of the invention. These include 5-substituted pyrimidines, 6-azapyrimidines, and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, 1993, pp. 276-278) and are desirable base substitutions, even more particularly when combined with 2'-O-methoxyethyl or 2'-O-methyl sugar modifications. Representative United States patents that teach the preparation of certain of the above noted modified nucleobases as well as other modified nucleobases include U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; and 5,750,692, each of which is herein incorporated by reference.

Another modification of a nucleobase oligomer of the invention involves chemically linking to the nucleobase oligomer one or more moieties or conjugates that enhance the activity, cellular distribution, or cellular uptake of the oligonucleotide. Such moieties include but are not limited to lipid moieties such as a cholesterol moiety (Letsinger et al., Proc. Natl. Acad. Sci. USA, 86:6553-6556, 1989), cholic acid (Manoharan et al., Bioorg. Med. Chem. Let, 4:1053-1060, 1994), a thioether, e.g., hexyl-S-tritylthiol (Manoharan et al., Ann. N.Y. Acad. Sci., 660:306-309, 1992; Manoharan et al., Bioorg. Med. Chem. Let., 3:2765-2770, 1993), a thiocholesterol (Oberhauser et al., Nucl. Acids Res., 20:533-538: 1992), an aliphatic chain, e.g., dodecandiol or undecyl residues (Saison-Behmoaras et al., EMBO J., 10:1111-1118, 1991; Kabanov et al., FEBS Lett., 259:327-330, 1990; Svinarchuk et al., Biochimie, 75:49-54, 1993), a phospholipid, e.g., di-hexadecyl-rac-glycerol or triethylammonium 1,2-di-O-hexadecyl-rac-glycero-3-H-phosphonate (Manoharan et al., Tetrahedron Lett., 36:3651-3654, 1995; Shea et al., Nucl. Acids Res., 18:3777-3783, 1990), a polyamine or a polyethylene glycol chain (Manoharan et al., Nucleosides & Nucleotides, 14:969-973, 1995), or adamantane acetic acid (Manoharan et al., Tetrahedron Lett., 36:3651-3654, 1995), a palmityl moiety (Mishra et al., Biochim. Biophys. Acta, 1264:229-237, 1995), or an octadecylamine or hexylamino-carbonyl-oxycholesterol moiety (Crooke et al., J. Pharmacol. Exp. Ther., 277:923-937, 1996. Representative United States patents that teach the preparation of such nucleobase oligomer conjugates include U.S. Pat. Nos. 4,587,044; 4,605,735; 4,667,025; 4,762,779; 4,789,737; 4,824,941; 4,828,979; 4,835,263; 4,876,335; 4,904,582; 4,948,882; 4,958,013; 5,082,830; 5,109,124; 5,112,963; 5,118,802; 5,138,045; 5,214,136; 5,218,105; 5,245,022; 5,254,469; 5,258,506; 5,262,536; 5,272,250; 5,292,873; 5,317,098; 5,371,241, 5,391,723; 5,414,077; 5,416,203, 5,451,463; 5,486,603; 5,510,475; 5,512,439; 5,512,667; 5,514,785; 5,525,465; 5,541,313; 5,545,730; 5,552,538; 5,565,552; 5,567,810; 5,574,142; 5,578,717; 5,578,718; 5,580,731; 5,585,481; 5,587,371; 5,591,584; 5,595,726; 5,597,696; 5,599,923; 5,599,928; 5,608,046; and 5,688,941, each of which is herein incorporated by reference.

The present invention also includes nucleobase oligomers that are chimeric compounds. "Chimeric" nucleobase oligomers are nucleobase oligomers, particularly oligonucleotides, that contain two or more chemically distinct regions, each made up of at least one monomer unit, i.e., a nucleotide in the case of an oligonucleotide. These nucleobase oligomers typically contain at least one region where the nucleobase oligomer is modified to confer, upon the nucleobase oligomer, increased resistance to nuclease degradation, increased cellular uptake, and/or increased binding affinity for the target nucleic acid. An additional region of the nucleobase oligomer may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of nucleobase oligomer inhibition of gene expression. Consequently, comparable results can often be obtained with shorter nucleobase oligomers when chimeric nucleobase oligomers are used, compared to phosphorothioate deoxyoligonucleotides hybridizing to the same target region.

Chimeric nucleobase oligomers of the invention may be formed as composite structures of two or more nucleobase oligomers as described above. Such nucleobase oligomers, when oligonucleotides, have also been referred to in the art as hybrids or gapmers. Representative United States patents that teach the preparation of such hybrid structures include U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference in its entirety.

The nucleobase oligomers used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The nucleobase oligomers of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include U.S. Pat. Nos. 5,108,921; 5,354,844; 5,416, 016; 5,459,127; 5,521,291; 5,543,158; 5,547,932; 5,583, 020; 5,591,721; 4,426,330; 4,534,899; 5,013,556; 5,108, 921; 5,213,804; 5,227,170; 5,264,221; 5,356,633; 5,395, 619; 5,416,016; 5,417,978; 5,462,854; 5,469,854; 5,512, 295; 5,527,528; 5,534,259; 5,543,152; 5,556,948; 5,580, 575; and 5,595,756, each of which is herein incorporated by reference.

Delivery of Nucleobase Oligomers

Naked inhibitory nucleic acid molecules, or analogs thereof, are capable of entering mammalian cells and inhibiting expression of a gene of interest. Nonetheless, it may be desirable to utilize a formulation that aids in the delivery of oligonucleotides or other nucleobase oligomers to cells (see, e.g., U.S. Pat. Nos. 5,656,611, 5,753,613, 5,785,992, 6,120, 798, 6,221,959, 6,346,613, and 6,353,055, each of which is hereby incorporated by reference).

Antibodies

Antibodies that selectively bind a TIM polypeptide (e.g., TIM1, TIM3, TIM4), phosphatidylserine, or a phosphatidylserine receptor, and inhibit its activity are useful in the methods of the invention. In one embodiment, selective binding of antibody to a TIM polypeptide reduces biological activity of the receptor, respectively, e.g., as assayed by analyzing binding to a ligand for the receptor. In another embodiment, selective binding of antibody to TIM polypeptide reduces the biological activity of its ligand, e.g., binding to its receptor.

Methods of preparing antibodies are well known to those of ordinary skill in the science of immunology. As used herein, the term "antibody" means not only intact antibody molecules, but also fragments of antibody molecules that retain immunogen-binding ability. Such fragments are also well known in the art and are regularly employed both in vitro and in vivo. Accordingly, as used herein, the term "antibody" means not only intact immunoglobulin molecules but also the well-known active fragments F(ab')$_2$, and Fab. F(ab')$_2$, and Fab fragments that lack the Fc fragment of intact antibody, clear more rapidly from the circulation, and may have less non-specific tissue binding of an intact antibody (Wahl et al., J. Nucl. Med. 24:316-325 (1983). The antibodies of the invention comprise whole native antibodies, bispecific antibodies; chimeric antibodies; Fab, Fab', single chain V region fragments (scFv), fusion polypeptides, and unconventional antibodies.

In one embodiment, an antibody that bind a TIM polypeptide is a polyclonal antibody. The preparation and use of polyclonal antibodies are known to the skilled artisan. The invention also encompasses hybrid antibodies, in which one pair of heavy and light chains is obtained from a first antibody, while the other pair of heavy and light chains is obtained from a different second antibody. Such hybrids may also be formed using humanized heavy and light chains. Such antibodies are often referred to as "chimeric" antibodies.

In general, intact antibodies are said to contain "Fc" and "Fab" regions. The Fc regions are involved in complement activation and are not involved in antigen binding. An antibody from which the Fc' region has been enzymatically cleaved, or which has been produced without the Fc' region, designated an "F(ab')$_2$" fragment, retains both of the antigen binding sites of the intact antibody. Similarly, an antibody from which the Fc region has been enzymatically cleaved, or which has been produced without the Fc region, designated an "Fab'" fragment, retains one of the antigen binding sites of the intact antibody. Fab' fragments consist of a covalently bound antibody light chain and a portion of the antibody heavy chain, denoted "Fd." The Fd fragments are the major determinants of antibody specificity (a single Fd fragment may be associated with up to ten different light chains without altering antibody specificity). Isolated Fd fragments retain the ability to specifically bind to immunogenic epitopes.

Antibodies can be made by any of the methods known in the art utilizing a TIM polypeptide, or fragments thereof. One method of obtaining antibodies is to immunize suitable host animals with an immunogen and to follow standard procedures for polyclonal or monoclonal antibody production. The immunogen will facilitate presentation of the immunogen on the cell surface. Immunization of a suitable host can be carried out in a number of ways. Nucleic acid sequences encoding TIM polypeptide or immunogenic fragments thereof, can be provided to the host in a delivery vehicle that is taken up by immune cells of the host. The cells will in turn express the receptor on the cell surface generating an immunogenic response in the host. Alternatively, nucleic acid sequences encoding a TIM polypeptide or immunogenic fragments thereof, can be expressed in cells in vitro, followed by isolation of the polypeptide and administration of the polypeptide to a suitable host in which antibodies are raised.

Alternatively, antibodies against a TIM polypeptide may, if desired, be derived from an antibody phage display library. A bacteriophage is capable of infecting and reproducing within bacteria, which can be engineered, when combined with human antibody genes, to display human antibody proteins. Phage display is the process by which the phage is made to 'display' the human antibody proteins on its surface. Genes from the human antibody gene libraries are inserted into a population of phage. Each phage carries the genes for a different antibody and thus displays a different antibody on its surface.

Antibodies made by any method known in the art can then be purified from the host. Antibody purification methods may include salt precipitation (for example, with ammonium sulfate), ion exchange chromatography (for example, on a cationic or anionic exchange column preferably run at neutral pH and eluted with step gradients of increasing ionic strength), gel filtration chromatography (including gel filtration HPLC), and chromatography on affinity resins such as protein A, protein G, hydroxyapatite, and anti-immunoglobulin. Antibodies can be conveniently produced from hybridoma cells engineered to express the antibody. Methods of making hybridomas are well known in the art. The hybridoma cells can be cultured in a suitable medium, and spent medium can be used as an antibody source. Polynucleotides encoding the antibody of interest can in turn be obtained from the hybridoma that produces the antibody, and then the antibody may be produced synthetically or recombinantly from these DNA sequences. For the production of large amounts of antibody, it is generally more convenient to obtain an ascites fluid. The method of raising ascites generally comprises injecting hybridoma cells into an immunologically naive histocompatible or immunotolerant mammal, especially a mouse. The mammal may be primed for ascites production by prior administration of a suitable composition (e.g., Pristane).

Monoclonal antibodies (Mabs) produced by methods of the invention can be "humanized" by methods known in the art. "Humanized" antibodies are antibodies in which at least part of the sequence has been altered from its initial form to render it more like human immunoglobulins. Techniques to humanize antibodies are particularly useful when non-human animal (e.g., murine) antibodies are generated.

Examples of methods for humanizing a murine antibody are provided in U.S. Pat. Nos. 4,816,567, 5,530,101, 5,225,539, 5,585,089, 5,693,762 and 5,859,205.

In other embodiments, the invention provides "unconventional antibodies." Unconventional antibodies include, but are not limited to, nanobodies, linear antibodies (Zapata et al., Protein Eng. 8(10): 1057-1062,1995), single domain antibodies, single chain antibodies, and antibodies having multiple valencies (e.g., diabodies, tribodies, tetrabodies, and pentabodies). Nanobodies are the smallest fragments of naturally occurring heavy-chain antibodies that have evolved to be fully functional in the absence of a light chain. Nanobodies have the affinity and specificity of conventional antibodies although they are only half of the size of a single chain Fv fragment. The consequence of this unique structure, combined with their extreme stability and a high degree of homology with human antibody frameworks, is that nanobodies can bind therapeutic targets not accessible to conventional antibodies. Recombinant antibody fragments with multiple valencies provide high binding avidity and unique targeting specificity to cancer cells. These multimeric scFvs (e.g., diabodies, tetrabodies) offer an improvement over the parent antibody since small molecules of ~60-100 kDa in size provide faster blood clearance and rapid tissue uptake See Power et al., (Generation of recombinant multimeric antibody fragments for tumor diagnosis and therapy. Methods Mol Biol, 207, 335-50, 2003); and Wu et al. (Anti-carcinoembryonic antigen (CEA) diabody for rapid tumor targeting and imaging. Tumor Targeting, 4, 47-58, 1999).

Various techniques for making unconventional antibodies have been described. Bispecific antibodies produced using leucine zippers are described by Kostelny et al. (J. Immunol. 148(5):1547-1553, 1992). Diabody technology is described by Hollinger et al. (Proc. Natl. Acad. Sci. USA 90:6444-6448, 1993). Another strategy for making bispecific antibody fragments by the use of single-chain Fv (sFv) diners is described by Gruber et al. (J. Immunol. 152:5368, 1994). Trispecific antibodies are described by Tutt et al. (J. Immunol. 147:60, 1991). Single chain Fv polypeptide antibodies include a covalently linked VH::VL heterodimer which can be expressed from a nucleic acid including VH- and VL-encoding sequences either joined directly or joined by a peptide-encoding linker as described by Huston, et al. (Proc. Nat. Acad. Sci. USA, 85:5879-5883, 1988). See, also, U.S. Pat. Nos. 5,091,513, 5,132,405 and 4,956,778; and U.S. Patent Publication Nos. 20050196754 and 20050196754.

Methods of Treatment

The invention provides methods of treating viral diseases and/or disorders or symptoms thereof which comprise administering a therapeutically effective amount of an agent that inhibits viral entry as described herein to a subject (e.g., a mammal such as a human). Thus, one embodiment is a method of treating a subject suffering from or susceptible to a viral infection, viral disease or disorder or symptom thereof. The method includes the step of administering to the mammal a therapeutic or prophylactic amount of an amount of a compound herein sufficient to treat the disease or disorder or symptom thereof, under conditions such that the disease or disorder is prevented or treated.

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g., opinion) or objective (e.g., measurable by a test or diagnostic method).

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

The therapeutic methods of the invention (which include prophylactic treatment) in general comprise administration of a therapeutically effective amount of the agents herein, to a subject (e.g., animal, human) in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). The agents herein may be also used in the treatment of any other disorders in which an alphavirus may be implicated.

In one embodiment, the invention provides a method of monitoring treatment progress. The method includes the step of determining a level of diagnostic marker (Marker) (e.g., any target delineated herein modulated by a compound herein, a protein or indicator thereof, etc.) or diagnostic measurement (e.g., screen, assay) in a subject suffering from or susceptible to a disorder or symptoms thereof associated with an alphavirus, in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

Pharmaceutical Compositions and Administration

The invention features pharmaceutical compositions that comprise agents that inhibit viral entry as described herein. The pharmaceutical compositions useful herein contain a pharmaceutically acceptable carrier, including any suitable diluent or excipient, which includes any pharmaceutical agent that does not itself induce the production of an immune response harmful to the vertebrate receiving the composition, and which may be administered without undue toxicity and an agent of the invention. As used herein, the term "pharmaceutically acceptable" means being approved by a regulatory agency of the Federal or a state government or listed in the U.S. Pharmacopia, European Pharmacopia or other generally recognized pharmacopia for use in mammals, and more particularly in humans. These compositions can be useful as a vaccine and/or antigenic compositions for inducing a protective immune response in a vertebrate.

Pharmaceutically acceptable carriers include but are not limited to saline, buffered saline, dextrose, water, glycerol, sterile isotonic aqueous buffer, and combinations thereof. A thorough discussion of pharmaceutically acceptable carriers, diluents, and other excipients is presented in Remington's Pharmaceutical Sciences (Mack Pub. Co. N.J. current edition). The formulation should suit the mode of administration. In a preferred embodiment, the formulation is suitable for administration to humans, preferably is sterile, non-particulate and/or non-pyrogenic.

The composition, if desired, can also contain minor amounts of wetting or emulsifying agents, or pH buffering agents. The composition can be a solid form, such as a lyophilized powder suitable for reconstitution, a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

In certain embodiments, the VLP composition is supplied in liquid form, for example in a sealed container indicating the quantity and concentration of the VLP composition. Preferably, the liquid form of the VLP composition is supplied in a hermetically sealed container at least about 50 µg/ml, more preferably at least about 100 µg/ml, at least about 200 µg/ml, at least 500 µg/ml, or at least 1 mg/ml.

Generally, agents of the invention are administered in an effective amount or quantity (as described herein) sufficient to inhibit viral entry. Preferably, administration of the VLP of the invention elicits immunity against a virus. Typically, the dose can be adjusted within this range based on, e.g., age, physical condition, body weight, sex, diet, time of administration, and other clinical factors. The prophylactic vaccine formulation is systemically administered, e.g., by subcutaneous or intramuscular injection using a needle and syringe, or a needle-less injection device. Alternatively, the vaccine formulation is administered intranasally, either by drops, large particle aerosol (greater than about 10 microns), or spray into the upper respiratory tract or small particle aerosol (less than 10 microns) or spray into the lower respiratory tract. While any of the above routes of delivery results in an immune response, intranasal administration confers the added benefit of eliciting mucosal immunity at the site of entry of many viruses, including alphaviruses, flaviviruses, filoviruses, or arenviruses.

Thus, the invention also comprises a method of formulating a composition that induces immunity to an infection or at least one symptom thereof to a mammal, comprising adding to said formulation an effective dose of an agent that inhibits viral entry. In one embodiment, the infection is an infection by an enveloped virus (e.g., filoviruses EBOV and MARV; arenaviruses JUNV, MACV, AMAV, and TCRV; alphaviruses EEEV, CHKV, SINV, and RRV; and flaviviruses DENV and WNV).

In certain cases, stimulation of immunity with a single dose is preferred, however additional dosages can be also be administered, by the same or different route, to achieve the desired effect. In neonates and infants, for example, multiple administrations may be required to elicit sufficient levels of immunity. Administration can continue at intervals throughout childhood, as necessary to maintain sufficient levels of protection against infections. Similarly, adults who are particularly susceptible to repeated or serious infections, such as, for example, health care workers, day care workers, family members of young children, the elderly, and individuals with compromised cardiopulmonary function or immune systems may require multiple immunizations to establish and/or maintain protective immune responses. Levels of induced immunity can be monitored, for example, by measuring amounts of neutralizing secretory and serum antibodies, and dosages adjusted or vaccinations repeated as necessary to elicit and maintain desired levels of protection.

Methods of Delivery

Agents of the invention are useful for preparing compositions that inhibit viral entry. Such compositions are useful for the treatment or prevention of an infection by an enveloped virus (e.g., filoviruses EBOV and MARV; arenaviruses JUNV, MACV, AMAV, and TCRV; alphaviruses EEEV, CHKV, SINV, and RRV; and flaviviruses DENV and WNV). In one embodiment, the invention encompasses a method of inhibiting viral entry by administering an inhibitory nucleic acid molecule (e.g., an antisense molecule, an siRNA, of shRNA). In another embodiment, the invention encompasses a method of inhibiting viral entry by administering an antibody or antibody fragment (e.g., a monoclonal or polyclonal antibody or Fc fragment). In another embodiment, the invention encompasses a method of inhibiting viral entry by administering an an exogenous TIM protein or fragment thereof. In another embodiment, the invention encompasses a method of inhibiting viral entry by administering a phospholipid (e.g., 1,2-diacyl-sn-glycero-3-phospho-L-serine (PS) or 1,2-diacyl-sn-glycero-3-phosphoethanolamine (PE)).

The invention also provides a method to induce or provide immunity to viral infection or at least one symptom thereof in a subject, comprising administering at least one effective dose of an agent as described herein. In another embodiment, the method comprises inducing immunity to a viral infection, e.g., alphavirus or flavivirus infection, or at least one symptom thereof by administering said formulation in multiple doses.

Agents of the invention can induce substantial immunity in a vertebrate (e.g., a human) when administered to said vertebrate. The substantial immunity protects or ameliorates infection or at least reduces a symptom of infection in said vertebrate. In some instances, if the said vertebrate is infected, said infection will be asymptomatic. The response may not be a fully protective response. In this case, if said vertebrate is infected with an infectious agent, the vertebrate will experience reduced symptoms or a shorter duration of symptoms compared to a non-immunized vertebrate.

In another embodiment, the invention comprises a method of vaccinating a mammal against a virus comprising administering to said mammal an agent that inhibits viral entry. In one embodiment, the invention encompasses a method of inhibiting viral entry by administering an inhibitory nucleic acid molecule (e.g., an antisense molecule, an siRNA, of shRNA). In another embodiment, the invention encompasses a method of inhibiting viral entry by administering an antibody or antibody fragment (e.g., a monoclonal or polyclonal antibody or Fc fragment). In another embodiment, the invention encompasses a method of inhibiting viral entry by administering an an exogenous TIM protein or fragment thereof. In another embodiment, the invention encompasses a method of inhibiting viral entry by administering a phospholipid (e.g., 1,2-diacyl-sn-glycero-3-phospho-L-serine (PS) or 1,2-diacyl-sn-glycero-3-phosphoethanolamine (PE)).

In another embodiment, the invention comprises a method of inducing a protective cellular response to a viral infection or at least one symptom thereof in a subject, comprising administering at least one effective dose of an agent that inhibits viral entry. In one embodiment, the invention encompasses a method of inhibiting viral entry by administering an inhibitory nucleic acid molecule (e.g., an antisense molecule, an siRNA, of shRNA). In another embodiment, the invention encompasses a method of inhibiting viral entry by administering an antibody or antibody fragment (e.g., a monoclonal or polyclonal antibody or Fc fragment). In another embodiment, the invention encompasses a method of inhibiting viral entry by administering an an exogenous TIM protein or fragment thereof. In another embodiment, the invention encompasses a method of inhibiting viral entry by administering a phospholipid (e.g., 1,2-diacyl-sn-glycero-3-phospho-L-serine (PS) or 1,2-diacyl-sn-glycero-3-phosphoethanolamine (PE)).

As mentioned above, the agents of the invention prevent or reduce at least one symptom of an infection in a subject. A reduction in a symptom may be determined subjectively or objectively, e.g., self assessment by a subject, by a clinician's assessment or by conducting an appropriate assay or measurement (e.g., body temperature), including, e.g., a quality of life assessment, a slowed progression of viral infection or additional symptoms, a reduced severity of viral symptoms or a suitable assays (e.g., antibody titer and/or T-cell activation assay). The objective assessment comprises both animal and human assessments.

The invention also provides assays to identify inhibitors of viral entry comprising, in at least one embodiment, genetically modified target cells expressing at least one viral receptor (e.g., TIM proteins), together with any co-receptors which might be required for infection or entry. These cells are genetically modified in the sense that they express a reporter gene, such as an affinity tag, a fluorogenic protein or an enzyme able to convert substrates into fluorogenic, chromogenic or luminometric products. Coupling this type of reporter signal to an inhibition of viral infection is accomplished by arranging the expression of the reporter gene to be strongly decreased (downregulated) upon infection with the virus of interest. In principle, this can be ensured by any suitable means, but especially preferred are GFP reporter genes, where, for example viral entry levels can assessed by measuring GFP expression.

The reporter gene product itself is fused to a cellular protein which, upon infection with the virus of interest is itself downregulated. For example, the reporter gene product can be fused to the corresponding viral receptor, which in many cases is downregulated upon infection.

Thus in one aspect a compound library may be screened for the ability to inhibit the infection of cells with an enveloped virus (e.g., filoviruses EBOV and MARV; arenaviruses JUNV, MACV, AMAV, and TCRV; alphaviruses EEEV, CHKV, SINV, and RRV; and flaviviruses DENV and WNV). An appropriate indicator cell line is generated that stably expresses a reporter gene. In one example, these cells are seeded in microtiter plates and incubated with virus or virus-like particles (VLPs) in the presence of different compounds, e.g., antibodies, in each well. Upon infection, the fusion protein is downregulated due to the expression of the viral genes. Consequently, only cells that have not been infected with virus will express the reporter gene. Thus, wells that exhibit a positive reporter signal contain compounds that inhibit infection. Variations and modifications of these assays will be apparent from the relevant sections of the description which explain individual parts of the assay in more detail. Specifically, in one embodiment, the reporter gene can be expressed when infection occurs rather than the reporter gene being downregulated upon infection.

In another embodiment, the invention provides methods for identifying inhibitors of viral entry using a reporter gene system as exemplified herein. Briefly, cells are plated into microtiter plates one day prior to infection. Pseudoviruses or VLPs encoding the reporter gene are first titrated by serial dilution. Similar amounts of pseudoviruses or VLPs are then incubated with the cells in presence of various candidate inhibitors. Cells are then analyzed for reporter gene activity by an appropriate method, such as flow cytometry. Inhibitors of viral entry are identified based on the expression of the reporter gene.

Kits

The invention also provides for a pharmaceutical pack or kit comprising one or more containers filled with one or more of the ingredients of the vaccine formulations of the invention. In a preferred embodiment, the kit comprises a containers, containing an agent that inhibits viral entry. Associated with such container(s) can be a notice in the form prescribed by a governmental agency regulating the manufacture, use or sale of pharmaceuticals or biological products, which notice reflects approval by the agency of manufacture, use or sale for human administration.

The invention also provides that the formulation be packaged in a hermetically sealed container such as an ampoule or sachette indicating the quantity of composition. In one embodiment, the composition is supplied as a liquid, in another embodiment, as a dry sterilized lyophilized powder or water free concentrate in a hermetically sealed container and can be reconstituted, e.g., with water or saline to the appropriate concentration for administration to a subject. The invention also features a kit comprising an agent that inhibits viral entry as described herein.

The following examples are offered by way of illustration, not by way of limitation. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the above description, but instead should be determined with reference to the appended claims along with their full scope of equivalents.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Figure 2A:
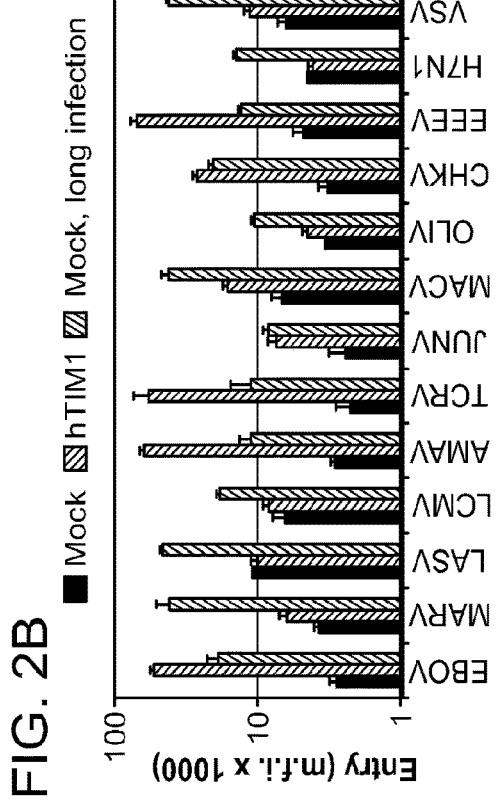
FIGS. 2A-2F depict studies of exogenous hTIM1 use in 293T and 3T3 cells.
Figure 2B:
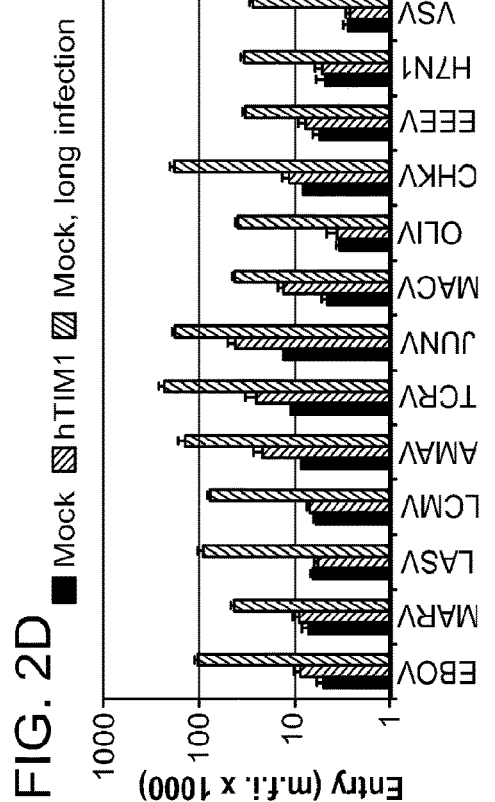
Figure 2C:
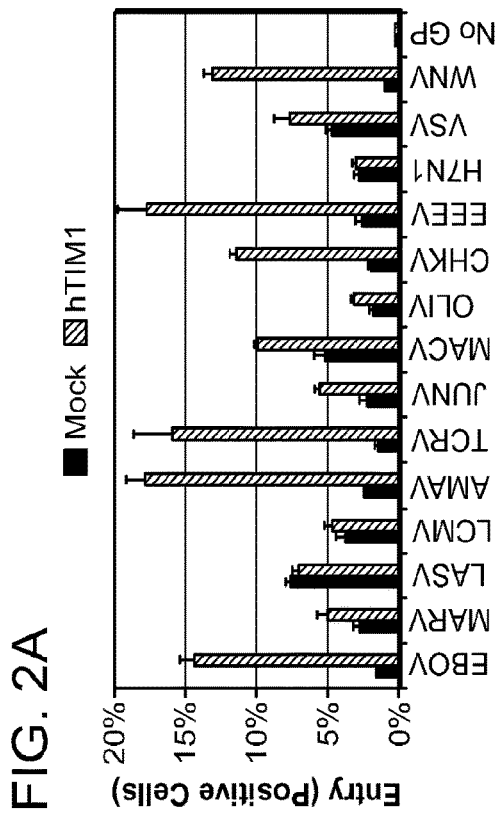
Figure 2D:
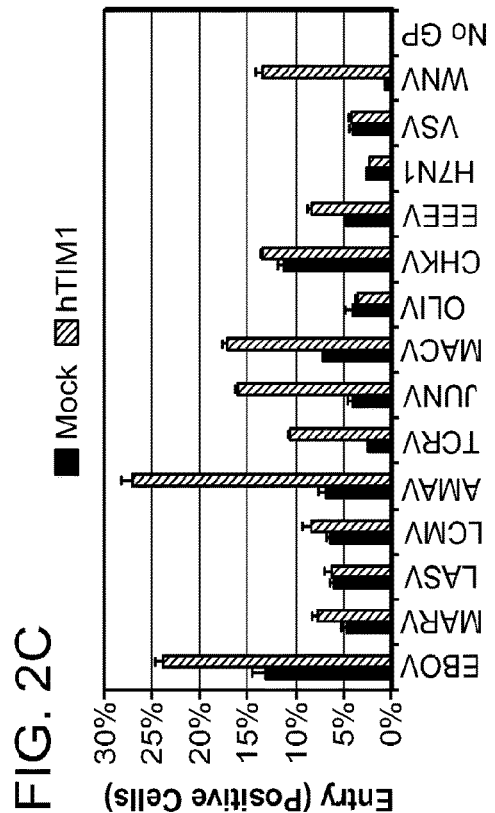
Figures 2E, 2F:
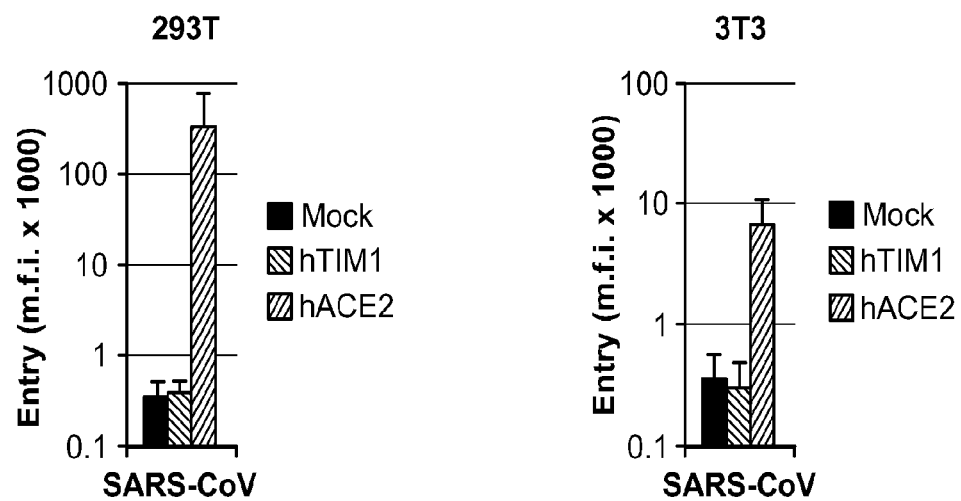
Figure 3B:
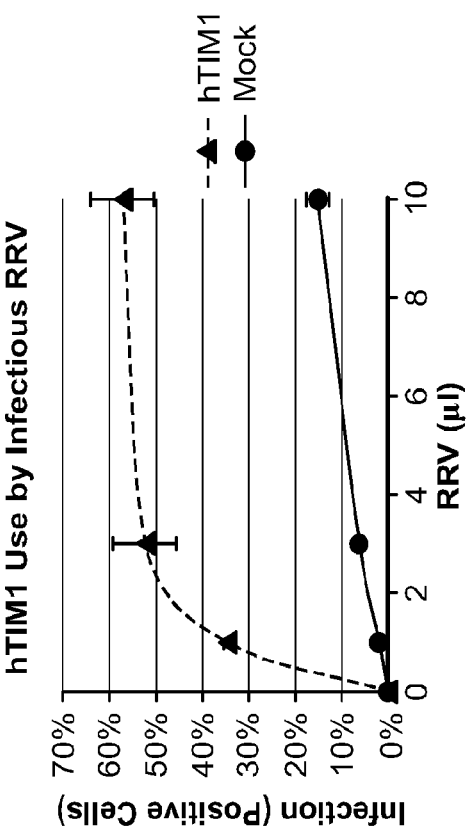
FIGS. 3A-3E show that hTIM1 increased the infection of diverse replication-competent viruses. 293T cells transduced with hTIM1 or hACE2 (mock) were infected for 1-6 hr. with infectious virus at increasing titers.
Figure 3D:
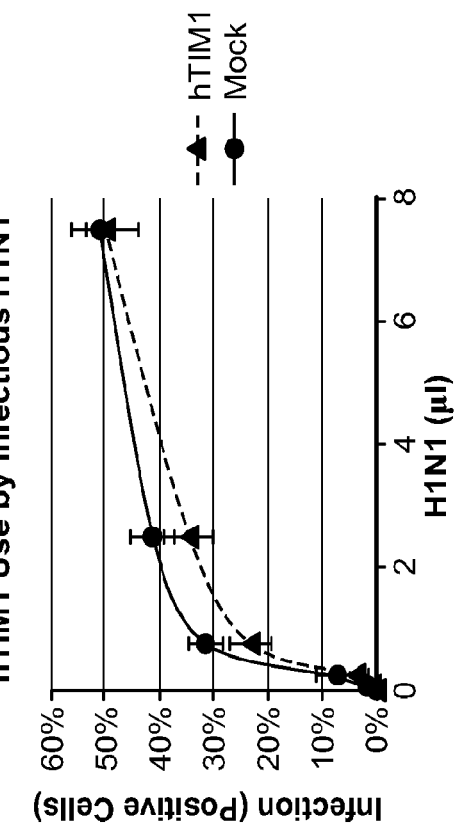
Figure 3A:
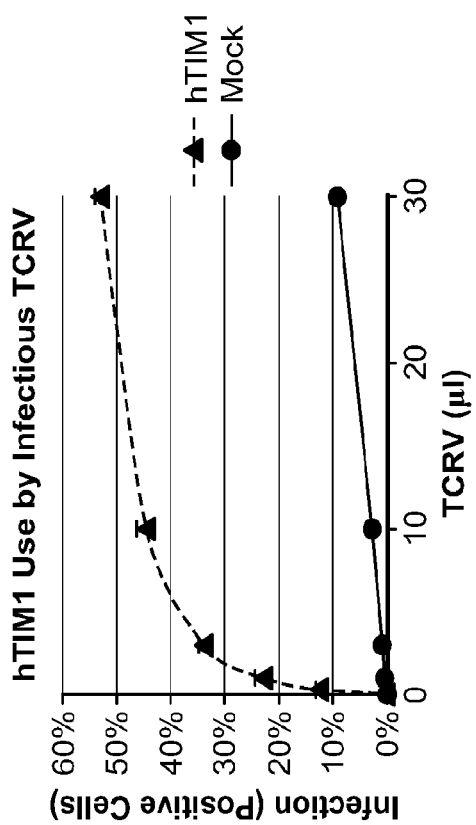
Figure 3C:
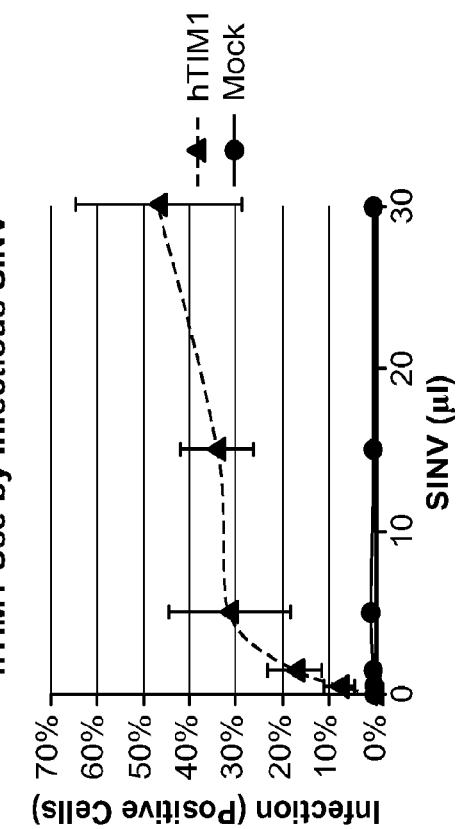
Figure 3E:
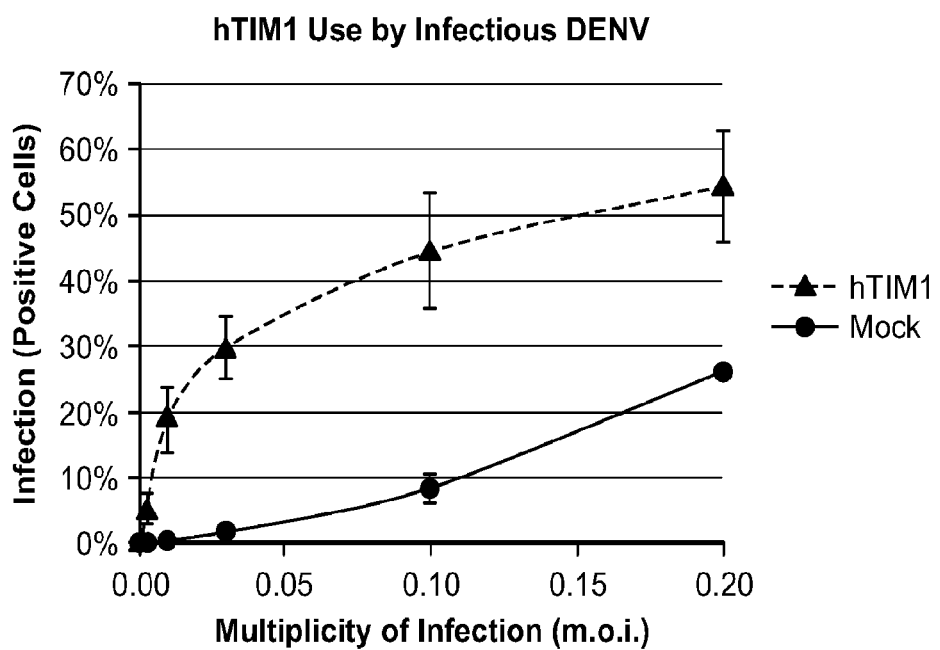

Example 1: hTIM1 Promoted Pseudovirus and VLP Entry Mediated by a Range of Viral Entry Proteins The specificity of viral use of hTIM1 was tested in two cell lines that express little or no endogenous TIM1: human 293T and murine 3T3 cells (FIGS. 1A and 1B). Cells engineered to overexpress hTIM1 or hACE2, a control receptor, were infected with a panel of 14 MLV pseudoviruses bearing the GPs of the filoviruses Ebola virus (EBOV) and Marburg virus (MARV), the arenaviruses Lassa virus (LASV), Lymphocytic choriomeningitis (LCMV), Amapari virus (AMAV), Tacaribe virus (TCRV), Junin virus (JUNV), Machupo virus (MACV) and Olifantsvlei (OLIV), the alphaviruses Chikungunya virus (CHKV) and Easter equine encephalitis virus (EEEV), the orthomyxovirus Influenza A (FLUAV) H7N1, the rhabdovirus Vesicular stomatitis virus (VSV) or the coronavirus Severe acute respiratory syndrome coronavirus (SARS-CoV). In addition, cells were infected with VLPs bearing the entry proteins of WNV, a member of the flavivirus family. As shown in FIGS. 1C and 2E, relative to control cells, many pseudoviruses infected hTIM1-expressing 293T cells more efficiently. The entry of EBOV, AMAV, TCRV and EEEV pseudoviruses as well as WNV VLPs was strongly increased by hTIM1 (over ~15 fold), that of CHKV considerably (~8 fold) and that of MARV, JUNV, MACV and VSV moderately (~2-5 fold). The entry of the remaining pseudoviruses tested—LASV, LCMV, OLIV, H7N1 and SARS-CoV—was increased by less than twofold, with LASV, H7N1 and SARS-CoV being the least affected. Unlike in 293T cells, hTIM1 overexpression in 3T3 cells had a less dramatic impact on viral entry (FIGS. 1D and 2F): Only WNV VLPs showed a strong increase in entry in hTIM1-expressing 3T3 cells relative to control 3T3 cells, while EBOV, AMAV, TCRV, JUNV and MACV pseudoviruses showed a moderate increase. In both experiments virus titers were not limiting for non-hTIM1-using viruses, since longer infection times yielded higher levels of entry in the control cells (FIGS. 2B and 2D). Furthermore, pseudovirus preparations bearing no viral GPs did not yield any positive cells (FIGS. 2A and 2C), indicating that all observed entry was dependent on the presence of viral entry proteins. Without being bound to a particular theory, together these data suggest that hTIM1 supports the entry of a wide range of pseudoviruses, in particular those for which no high-affinity cell surface receptor has been identified. In addition, the effect of hTIM1 is dependent on the cellular background in which the experiment is performed.

Figure 1F:
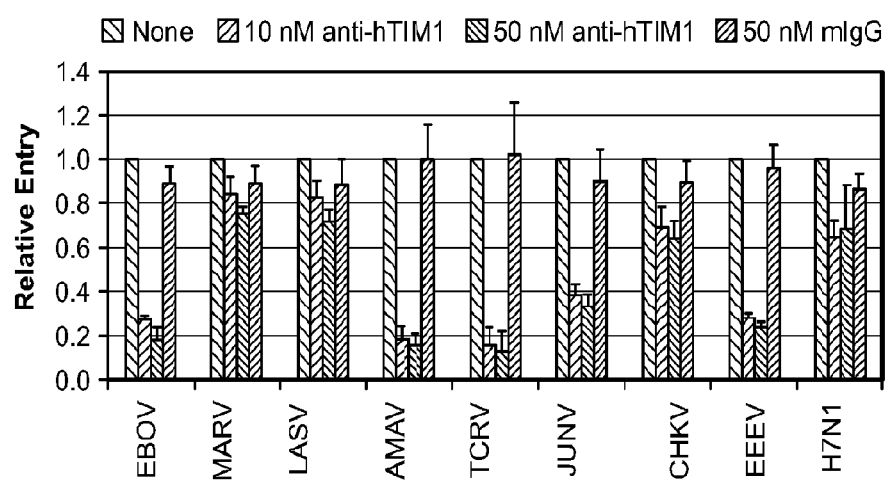

To further assess the role of TIM1, the ability of an anti-hTIM1 antibody to inhibit infection of Huh7 cells, a human cell line with high endogenous hTIM1 expression, was tested (FIG. 1E). As shown in FIG. 1F the mouse monoclonal anti-hTIM1 antibody 3D1 [21] inhibited the entry of EBOV, AMAV, TCRV and EEEV pseudoviruses by over 70% at a 10 nM concentration, indicating that hTIM1 serves as a major entry factor for these viruses in Huh7 cells. JUNV pseudovirus entry was also considerably inhibited by anti-hTIM1 3D1 (by 60%), indicating that hTIM1 can contribute to the entry of this virus in Huh7 cells, although JUNV is known to predominantly enter other human cells via transferrin receptor 1 [41,47,48]. In contrast, the other pseudoviruses tested, including CHKV and MARV, were only moderately affected by the presence of anti-hTIM1 3D1. Thus, hTIM1 is not an important entry factor for these viruses in Huh7 cells. The results of these entry blocking experiments are consistent with the gain-of-entry experiments in 293T cells (FIG. 1A), except that Huh7 cells were not efficiently infected by WNV VLPs.

The role of hTim1 in virus infection was confirmed, using replication-competent viruses. To circumvent the need for BSL3 or 4 laboratories (required for infectious MACV, JUNV, CHKV, EEEV or WNV), TCRV was chosen to represent the arenavirus family, RRV and SINV were chosen to represent the alphavirus family, and DENV was chosen to represent the flavivirus family. In addition, FLUAV H1N1 was used as a negative control. When hTim1-293T cells and the control hACE2-293T cells were infected with serially diluted viruses, infection levels were markedly enhanced in hTim1-293T cells across the board, except for H1N1 (FIGS. 3A-3E), which is consistent with the pseudovirus entry data shown in FIGS. 1A-1F. Of note, the magnitude of infection enhancement of DENV infection was greater at low virus titers. Without being bound to a particular theory, TIM1 may play a more important role when virus titers are limiting, for example at the initial phases of infection. This initial advantage conferred by hTIM1 was further amplified during the first few cycles of replication (FIG. 4B). As a surrogate for replication-competent EBOV, EBOV VP40-based VLPs [8] bearing the wildtype EBOV entry protein was used, and it was confirmed that hTIM1 efficiently enhanced their entry.

Figure 5B:
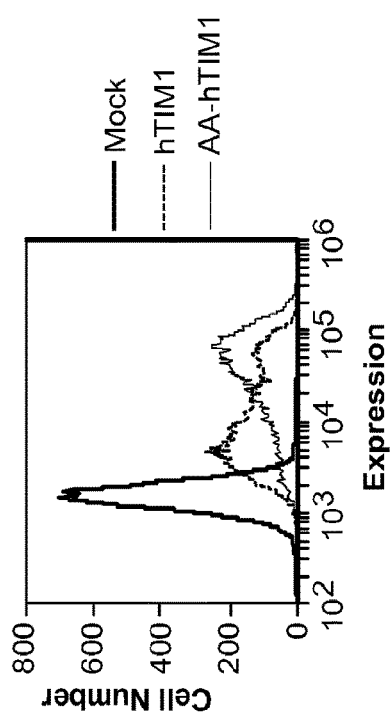
FIGS. 5A-5C depict that hTIM1-mediated viral entry was PS dependent.
Figure 5A:
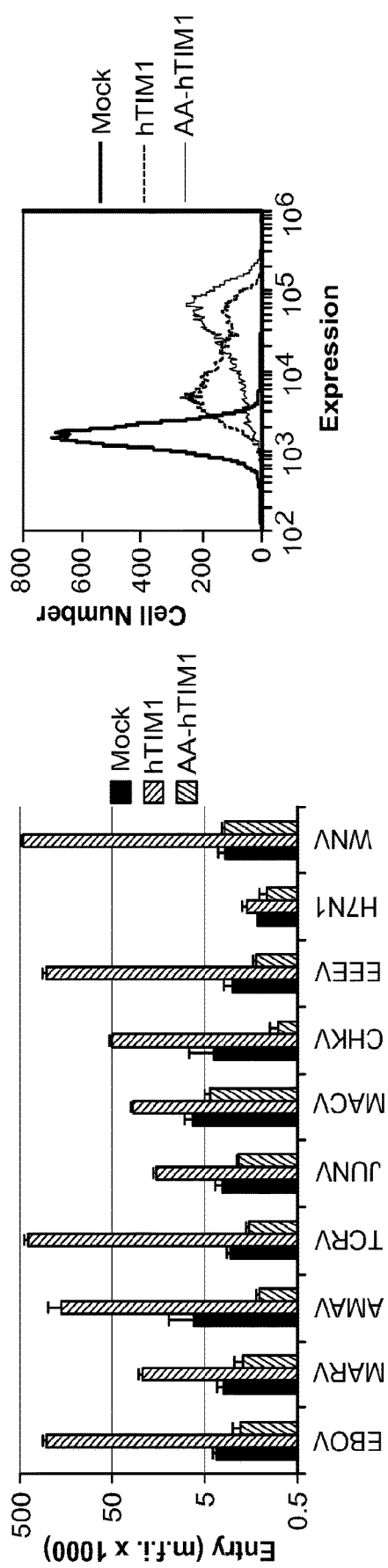

Example 2: hTIM1-Mediated Enhancement of Viral Entry was PS Dependent hTIM1 is a receptor involved in the PS-mediated uptake of apoptotic cells [21]. To test the hypothesis that hTIM1 may broadly increase viral entry because it binds 1,2-diacyl-sn-glycero-3-phospho-L-serine (PS) on viral membranes rather than to specific viral glycoproteins, viral usage of a hTIM1 variant defective in binding PS was compared with that of wt hTIM1. The mutant variant, hereafter referred to as AA-hTIM1, has two mutations in the PS-binding pocket that are known to nearly abrogate PS binding [19,21]. Indeed, when these receptors were overexpressed in 293T cells, AA-hTIM1 was unable to enhance the entry of any pseudovirus tested (FIG. 5A) despite efficient AA-hTIM1 expression (FIG. 5B). This indicates that viral hTIM1 usage is PS-dependent.

Figure 5C:
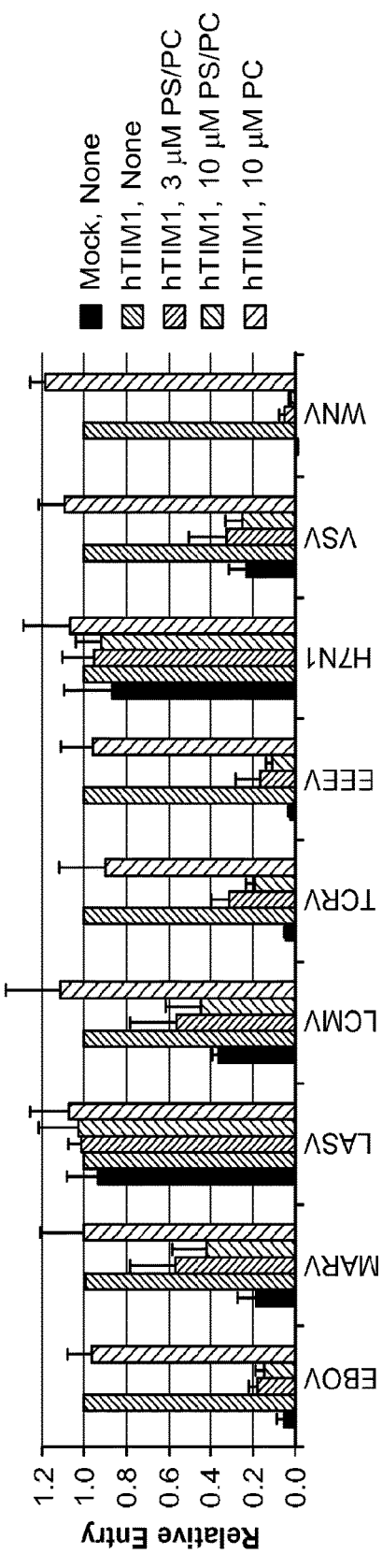
Figure 6:
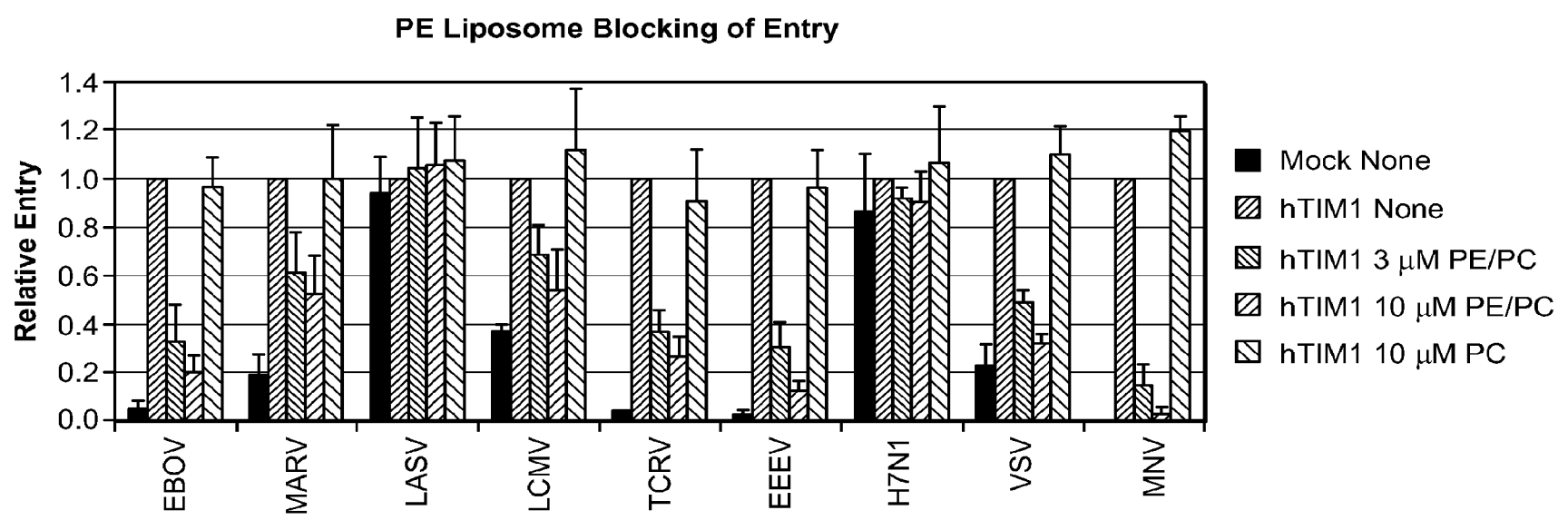

To further assess the role of PS, we tested whether various liposomes are able to block hTIM1-mediated viral entry (FIG. 5C). Consistent with a PS-dependent mechanism, liposomes consisting of 50% PS and 50% PC, but not those consisting of PC alone, efficiently blocked the entry of all hTIM1-using pseudoviruses into hTIM1-expressing 293T cells at 3 µM concentration. In contrast, the entry of LASV and H7N1 pseudoviruses, whose entry was not enhanced by hTIM1, were not affected by either liposomes. Unexpectedly, PE-containing liposomes were also able to inhibit hTIM1-mediated viral entry (FIG. 6). Without being bound to a particular theory, this observation raises the possibility that PE, another marker of apoptotic cells [49], which shares structural similarities with PS, may also play a role in viral hTIM1 usage.

Example 3: TIM1-Mediated Virion Internalization was Independent of Viral Entry Proteins PS dependency of viral hTIM1 usage indicated that virions lacking any viral entry protein should also bind to and internalize into the intracellular compartments of hTIM1-expressing cells. To test this hypothesis GFP-fused matrix proteins [45,46] were used that allow, when incorporated into the virions, the detection of prefusion stages of viral entry. As shown in FIGS. 7A and 7B, when 293T cells expressing hTIM1, AA-hTIM1 or a control receptor were infected with EBOV VP40-matrix-based VLPs (VP40-GFP VLPs), those bearing no GPs were readily internalized by hTIM1, provided that the TIM1 PS-binding domain was functional. Although EBOV GP-bearing VP40-GFP VLPs appeared to be internalized more efficiently than those lacking GP, this bias is most likely due to the fact that the latter are released 3 to 5 times less efficiently from the producer cells [50,51]. Consistent with this explanation, when the internalization experiment was repeated with RT-activity normalized MLVgag-GFP virions, even higher internalization efficiencies were obtained for GP-free than EBOV GP-bearing virions (FIGS. 7C and 7D). Thus, results presented in FIGS. 7A-7D demonstrate that virions bind to and internalize via hTIM1 in a manner that was independent of specific viral entry proteins, but instead was dependent on components of the viral membrane.

Example 4: Differing Mechanisms Underlie the Inability of hTIM1 to Promote Infection of Some Pseudoviruses Whether the observation that GP-free MLVgag-GFP virions are readily internalized by hTIM1 could be extended to the same virions bearing the GPs of LASV, H7N1 and SARS-CoV was tested. These viruses were unaffected by hTIM1 expression in the entry assays that rely on a post-fusion readout (FIGS. 1 and 2). As shown in FIG. 8A, the internalization of H7N1 and SARS MLVgag-GFP virions, normalized for RT-activity, considerably increased in the presence of hTIM1, albeit less than that of EBOV and GP-free virions. Moreover, this internalization was blocked by PS-containing liposomes, but not by those consisting of only PC (FIG. 8B). These findings indicate that hTIM1 promotes the PS-dependent internalization of H7N1 and SARS-CoV virions without leading to productive infection (compare with FIGS. 1C, 2E, and 8B). In contrast, internalization of LASV MLVgag-GFP virions was only minimally increased by hTIM1 (FIG. 8A) and was not blocked by PS-containing liposomes (FIG. 8B). Without being bound to a particular theory, the molecular mechanism responsible for the lack of hTIM1-mediated entry for LASV was distinct from those of H7N1 and SARS-CoV. As suggested by Morizono et al. [34], PS receptor usage by viruses may be influenced by their affinity for other cell surface receptors. For instance, LASV internalization via alpha dystroglycan, its primary receptor, may be too efficient for PS receptors to compete with.

This receptor-affinity hypothesis was tested using GPs from various SARS-CoV isolates; Tor2, isolated from the major SARS-CoV outbreak, GD from a minor one, and SZ, from a reservoir species civet cat, respectively show high, moderate and low affinity to hACE2 [36]. 293T cells expressing hACE2, with or without hTIM1, were infected with pseudoviruses bearing these GPs. As shown in FIG. 9, infection levels reached by these three viruses corresponded to their reported affinities to hACE2, showing ~20 fold difference between Tor2 and SZ. However, no TIM1-mediated entry increase was observed with any of these SARS-CoV GPs, while the entry of the control virus TCRV was substantially enhanced. These results indicate that receptor affinity cannot explain the inability of hTIM1 to promote infection in the case of SARS-CoV.

Example 5: Viral Usage of the PS Receptors hAxl and hTIM4 Paralleled that of hTIM1

Since a number of human PS receptors have been described [25], PS receptors other than hTIM1 were examined to determine whether they have a similarly broad impact on viral entry. For example, hAxl was recently shown to enhance the infection mediated by the entry proteins of Sindbis, Ross River and Baculo viruses in a PS-dependent manner by binding the serum proteins Gas-6 and Protein S, which in turn bind PS displayed on these viruses' membranes [34]. As shown in FIG. 10A, the infection of 293T cells expressing exogenous hAxl with the panel of pseudoviruses and VLPs used in FIG. 1 yielded a pattern almost identical to that observed with hTIM1. One exception, however, was that WNV VLP entry was not much enhanced by hAxl, indicating that Gas-6 and Protein S from FBS might bind PS differently compared to TIM proteins. Whether hTIM3 and 4, also shown to be PS receptors [21,22], similarly enhance viral entry was tested. Again, 293T cells expressing hTIM3, hTIM4 or a control receptor were infected with various pseudoviruses and WNV VLPs (FIGS. 10B and 10C). While hTIM4 expression resulted in a pattern of entry enhancement similar to that of hTIM1, hTIM3 showed moderate support of TCRV pseudovirus and WNV VLP entry. Thus, the mechanisms underlying inefficient viral TIM3 usage seem to be complex (see, e.g., FIGS. 11A-11C). Collectively, these data indicated that different PS receptors tend to enhance infection of the same viruses—although not every virus uses every PS receptor—and indicate that PS receptors other than TIMs and Axl are also likely to increase the entry of a wide range of viruses using a common mechanism.

Although hTIM3 binds PS, it differs from hTIM1 and 4 in several aspects that could explain why it does not efficiently support viral entry. First, based on results obtained with the corresponding mouse TIM orthologs, its affinity for PS is lower than that of TIM1 and 4 [22]. Second, as illustrated in FIG. 11A, its stalk is much shorter than that of the other TIMs, which may prevent its PS-binding IgV domain from effectively reaching the GP-studded viral membranes. Finally, the stalk of TIM3 bears only a few O-glycosylation sites, whereas those of TIM1 and 4 are heavily covered with O-linked carbohydrates that could potentially participate in virus binding. To distinguish among these possible explanations, two stalk-truncated hTIM1 variants were produced, each similar in stalk length, but with very different numbers of O-glycosylation sites (FIG. 11A). These hTIM1 variants were expressed in 293T cells along with wt hTIM1 and a control receptor and infected with various hTIM1-using pseudoviruses, as well as with H7N1 pseudoviruses as a negative control. As shown in FIGS. 11B and 11C, truncation of the hTIM1 stalk affected entry of hTIM1-using viruses to varying degrees, with a considerable effect on EBOV, CHKV and EEEV and marginal effects on AMAV and TCRV. Hence, while a long stalk helped support the entry of some viruses, it was not a major determinant of TIM protein usage for others. These findings also show that the 0-glycans on the stalk play little or no role in determining viral TIM-protein usage, since the entry enhancements conferred by the heavily glycosylated 4197-287 and the sparsely glycosylated 4131-221 hTIM1 variants were similar when taking the minor difference in expression into account.

Experimental infections in animal models have shown that macrophages are early targets for the replication of several viruses [60,68]. Therefore the contribution of PS receptors to viral entry in mouse peritoneal macrophages, which are known to express TIM4 [21] and other PS receptors, was assessed. To be able to detect viral entry instantaneously, VLPs consisting of EBOV VP40 matrix proteins fused to β-lactamase (VP40-Bla VLPs [8]) were used for infection. As shown in FIG. 10D, the entry of VP40-Bla VLPs bearing EBOV GP was inhibited by 45% in the presence of PS-containing liposomes at 10 μM, reflecting as expected that other host cell molecules also play a role in virus infection. In contrast, the entry of the same VLPs bearing LASV GP was only little inhibited (by 8%). The blocking effect was specific for PS, as liposomes consisting of only PC did not inhibit either VLPs. These data are consistent with the notion that PS receptors can help potentiate viral infection in macrophages.

Example 6: hTIM1-Mediated EBOV Pseudovirus Entry was Dependent on NPC1

EBOV and MARV entry was recently shown to critically depend on NPC1, a cholesterol-transporting protein located in the endo/lysosomal compartment [15,16,17]. To test whether hTIM1 usage by EBOV and MARV is dependent on NPC1, NPC1-null CHO cells (NPC1$^{-/-}$) were used, as well as NPC1-null CHO cells engineered to overexpress mouse NPC1 (NPC1$^{-/-}$mNPC1) [35]. As expected based on earlier results (FIG. 1), EBOV pseudovirus entry, and to a lesser extent MARV entry, in NPC1$^{-/-}$mNPC1 cells was increased in the presence of hTIM1 (right panels of FIGS. 12A and 12B). In contrast, the previously reported non-permissiveness of NPC1$^{-/-}$ cells to EBOV and MARV [15] was not circumvented by hTIM1 overexpression (left panels of FIGS. 12A and 12B). These data indicate that hTIM1 expression cannot overcome NPC1 dependence, confirm the role of NPC1 as a Filovirus entry factor, and suggest that hTIM1 itself may best be regarded as an attachment factor.

Example 7: Antibodies or Antibody Fragments to hTIM1 Inhibited Infection Mediated by a Range of Viral Entry Proteins To assess the role of TIM1, the ability of an anti-hTIM1 antibody to inhibit infection of Huh7 cells, a human cell line with high endogenous hTIM1 expression, was tested (FIG. 14). As shown in FIG. 14 the mouse monoclonal anti-hTIM1 antibody 9F4 inhibited the entry of EBOV, MARV, AMAV, TCRV, JUNV, CHKV, EEEV, and WNV by over 70% at a 50 nM concentration, indicating that hTIM1 serves as a major entry factor for these viruses in 293T cells. H7N1 entry was also considerably inhibited by anti-hTIM1 9F4 (by 60%), indicating that hTIM1 can contribute to the entry of this virus in 293T cells. In contrast, LASV was only moderately affected by the presence of anti-hTIM1 9F4. Thus, hTIM1 is not an important entry factor for this virus in 293T cells.

To assess the role of TIM1, the ability of an anti-hTIM1 antibody to inhibit infection of Huh7 cells, a human cell line with high endogenous hTIM1 expression, was tested (FIG. 15). As shown in FIG. 15, TIM1-mFc inhibited the entry of EBOV, AMAV, TCRV, JUNV, and EEEV by over 70% at a 50 nM concentration, indicating that hTIM1 serves as a major entry factor for these viruses in Huh7 cells. H7N1 entry was also considerably inhibited by anti-hTIM1 3D1 (by 60%), indicating that hTIM1 can contribute to the entry of this virus in Huh7 cells. In contrast, the other pseudoviruses tested, including CHKV and MARV, were only moderately affected by the presence of TIM1-mFc. Thus, hTIM1 is not an important entry factor for these viruses in Huh7 cells. The results of these entry blocking experiments are generally consistent with the gain-of-entry experiments in Huh7 cells.

The results reported herein were obtained using the following methods and materials.

Cell Lines and Plasmids

HEK293T cells (human embryonic kidney; ATCC CRL-11268); Huh7 cells (human hepatocarcinoma); 3T3 cells (murine embryonic fibroblast; ATCC CCL-92); and MDCK (canine kidney) cells were grown at 37° C. in DMEM supplemented with 10% fetal bovine serum (FBS), 1 mM sodium pyruvate and 1% penicillin/streptomycin (P/S). $NPC1^{-/-}$ and $NPC1^{-/-}$mNPC1 CHO cells (also referred to as M12 and wt8, respectively [35]) were kept at 37° C. in DMEM/F12 with 5% FBS and 1% P/S (Daniel S. Ory at Washington University School of Medicine). C6/36 Aedes albopictus mosquito cells were maintained at 28° C. in DMEM containing 10% FBS, 1 mM sodium pyruvate and 1% P/S.

Coding sequences of hTIM1, hTIM3 and hTIM4 (without signal peptides) were PCR amplified from human T-cell or macrophage cDNA libraries and cloned into the retroviral expression vector pQCXIX (BD Biosciences) downstream of the signal peptide of mouse angiotensin-converting enzyme 2 (ACE2) and a myc-tag. Their sequences were deposited to the Genbank under accession numbers JX049978, JX049979 and JX049980, respectively. hAxl cDNA (clone 5205825, Invitrogen) was purchased and similarly cloned into pQCXIX with an N-terminal myc-tag. The PS-binding deficient variant of hTIM1 (AA-hTIM1) was created by site-directed mutagenesis. It carries W112A and F113A mutations based on the previously-described equivalent mutations in other TIM proteins [19,21]. The stalk-truncated 4131-221 hTIM1 and 4197-287 hTIM1 variants were obtained using deletion mutagenesis.

The plasmids encoding N-terminally myc-tagged human ACE2 (hACE2) and civet cat ACE2 were previously described [36]. Also previously described were the expression plasmids encoding the entry glycoprotein precursors of Zaire EBOV (Mayinga) and Lake Victoria MARV (Musoke), both lacking the mucin domains, Amapari virus (AMAV, BeAn 7063), Tacaribe virus (TCRV), Junin virus (JUNV, MC2), Machupo virus (MACV, Carvallo), Lassa fever virus (LASV, Josiah), lymphocytic choriomeningitis virus (LCMV, Armstrong), Chikungunya virus (CHKV, 37997), Eastern Equine Encephalitis virus (EEEV, FL91-4697), influenza A virus (FLUAV, H7: Rostock, N1: Puerto Rico), Vesicular stomatitis virus (VSV, Indiana), SARS coronavirus (SARS-CoV; Tor2, GD and SZ) and West Nile Virus (WNV, lineage 1, NY99) [36,37,38,39,40,41,42]. The precursor of the Oliveros virus (OLIV) entry protein was synthesized by GenScript based on Genbank ID AAC54654.1 and was cloned into pCAGGS.

Assessment of Receptor Expression

The expression of various receptors was assessed with monoclonal antibodies and detected using the Accuri C6 flow cytometer (BD Biosciences). To measure endogenous hTIM1 expression, cells were stained with mouse anti-hTIM1 antibody (clone 219211, R&D Systems) or purified mouse Fc (mFc) as a negative control. Primary antibody binding was detected with a phycoerythrin (PE)-conjugated goat anti-mouse antibody (Jackson ImmunoResearch Laboratories). To assess endogenous mouse TIM1 (mTIM1) expression, cells were stained with anti-mTIM1-PE, a PE-conjugated rat anti-mTIM1 antibody (clone RMT1-4, BioLegend) or with anti-mIFNγ-PE, a PE-conjugated rat anti-mouse interferon gamma antibody (BioLegend) used as negative control. Cells transfected or transduced to express exogenous receptors were stained with various antibodies. While the antibody used to detect wildtype (wt) hTIM1 and the AA-hTIM1 variant was the anti-hTIM1 antibody described above, that used in the hTIM1 stalk truncation experiment was anti-hTIM1 antibody 3D1, which specifically recognizes the IgV head domain of hTIM1 [21]. Expression of N-terminally myc-tagged hAxl, hTIM3/4, hACE2 and civet cat ACE2 was assessed using anti-myc antibody 9E10.

MLV Pseudovirus and WNV VLP Entry Assays

Pseudoviruses bearing various viral entry proteins were produced in 293T cells as described [38] by calcium-phosphate transfection of a retroviral vector pQCXIX (BD Biosciences) encoding eGFP together with two other plasmids, separately encoding a viral entry protein and the Moloney murine leukemia virus (MLV) gag and pol. For FLUAV H7N1, an additional plasmid encoding N1 neuraminidase (Puerto Rico) was co-transfected [40]. Pseudovirus-containing culture supernatants were harvested at 32-34 hrs post-transfection, filtered through a 0.45 µm PES membrane, stored at 4° C., and used within 2 weeks. WNV VLPs were produced and harvested in the same way after co-transfecting a plasmid encoding the WNV structural proteins (capsid and entry glycoproteins prM and E) and a WNV replicon encoding the non-structural proteins NS1-5 and GFP [42].

For infection, cells were plated on poly-lysine-coated (293T) or uncoated 48-well plates and incubated at 37° C. with pseudovirus- or VLP-containing supernatants diluted to yield comparable levels of infection. In order for virus entry enhancement not to be limited by virus titers, cells were generally incubated with virus supernatants for less than 1 hour, unless mentioned otherwise. Supernatants were then replaced with fresh medium, incubated for one (293T) or two (3T3, Huh? and $NPC1^{-/-}$) days to allow for eGFP reporter expression and infection levels were assessed by measuring GFP fluorescence with the Accuri C6 flow cytometer (BD Biosciences). Independent experiments were performed with independent pseudovirus and VLP preparations. In addition, all pseudoviruses and VLPs used in a given experiment were produced in parallel.

Infection Assays with Replication-Competent Viruses

Lyophilized infectious TCRV (TRVL 11573), passaged in suckling mice and Vero cells, and RRV (T-48) and SINV (Ar-339), both passaged in suckling mice, were purchased from ATCC, and resuspended in PBS according to the instructions. Type 2 infectious dengue virus (DENV, New Guinea C) was obtained by passaging in C6/36 Aedes albopictus mosquito cells. Virus-containing culture supernatants were 0.45 µm-filtered, stored at −80° C. and virus titers determined using plaque assays in baby hamster kidney cells as described [43]. Infectious FLUAV (H1N1, A/PR/8/34) was propagated in MDCK cells and cell debris were removed through a 0.45 µm filter [65]. For infection, cells were incubated for 1-6 hr. at 37° C. with viruses serially diluted in DMEM containing 10% FBS, washed and supplemented with fresh medium. At indicated days post-infection, cells were detached by trypsinization, washed, fixed with 1% formaldehyde in PBS and permeabilized with 0.1% saponin in PBS containing 2% goat serum. Cells were then stained with immune ascitic fluids (ATCC) for TCRV, RRV, and SINV; anti-FLUAV antibody C111 (Clontech); or anti-anti-DENV antibody 2H2 (Millipore) [44] followed by an Alexa 649- or PE-conjugated goat anti-mIgG antibody (Jackson ImmunoResearch Laboratories) and analyzed by flow cytometry.

Internalization Assays

VP40-GFP VLPs were produced in 293T cells by co-transfecting a pCAGGS-based plasmid encoding a previously described GFP-fusion version of the EBOV VP40 matrix protein [45] (Christopher F. Basler at Mount Sinai School of Medicine) with a plasmid encoding mucin-domain-deleted EBOV GP at 3:1 ratio. To make VP40-GFP VLPs bearing no entry protein, the VP40-GFP plasmid was similarly cotransfected with an empty plasmid. VLP-containing culture supernatants were harvested at 36 hr post-transfection and cell debris removed by two consecutive centrifugations at 900×g. The presence of fluorescent filo-virus-like particles in the supernatants was confirmed by fluorescence microscopy.

MLVgag-GFP pseudovirions were produced similarly as described for the non-fluorescent pseudoviruses, except that 25% of the MLV gag-pol plasmid DNA was replaced with plasmid DNA encoding a MLV gag-GFP fusion protein [46] (Walther Mothes at Yale University School of Medicine). Also, pQCXIX-eGFP was replaced with the same vector encoding a non-fluorescent protein. Virus supernatants were harvested at 34-36 hr post-transfection, 0.45 μm-filtered, purified by ultracentrifugation (SW40Ti rotor, 70,000×g for 2 hr at 10° C.) and resuspended in a small volume of DMEM containing 10% FBS.

To assess VLP/pseudovirion internalization, cells were incubated for 2-6 hr at 37° C. with VP40-GFP VLPs, with MLVgag-GFP virions normalized for MLV reverse-transcriptase (RT) activity or with mock supernatants obtained from cells transfected with a plasmid expressing eGFP alone. Uninternalized VLPs and virions were removed with two 1 min acid-washes (200 mM glycine, 150 mM NaCl, pH 3.0) followed by trypsinization at 37° C. for 15 min. Internalization of VLPs or pseudovirions was assessed by flow cytometry.

Entry Assays with VP40-β-Lactamase VLPs and Macrophages

VLPs made with EBOV VP40 matrix proteins fused to β-lactamase (Bla) and bearing EBOV GP, LASV GP or no GP were produced as described above for VP40-GFP VLPs. The VP40-Bla fusion construct was a gift from Paul Bates at University of Pennsylvania [8]. Naive peritoneal macrophages were obtained from wildtype BALB/cBYJ mice. Briefly, peritoneal cavity cells were plated in 12-well plates at $10^6$ per well and incubated for 1 hr. at room temperature to let macrophages adhere. After removing non-adherent cells by washing twice in PBS/2% FBS, macrophages were incubated overnight at 37° C. in RPMI containing 10% FBS, 1% P/S and 50 μM β-mercaptoethanol and infected the following day for 2 hr. at 37° C. with VP40-Bla VLPs. Infected cells were detached by scraping in trypsin/EDTA, washed and loaded with the Bla substrate CCF2-AM, as previously described [66]. The conversion of substrate by cytoplasmic esterases and Bla, which reflects VP40-Bla VLP entry, was detected using the LSR II flow cytometer (BD Biosciences).

Liposome Blocking Assays 1, 2-diacyl-sn-glycero-3-phospho-L-serine (PS), 1,2-diacyl-sn-glycero-3-phosphocholine (PC) and 1,2-diacyl-sn-glycero-3-phosphoethanolamine (PE) were purchased from Sigma and resuspended at 10 mg/ml in chloroform. Aliquots of PC alone or PC mixed with PS or PE at 1:1 molar ratios were dried under argon and then in a SpeedVac for 1 hr, followed by hydration in PBS at a concentration of 1 mM total lipids. Liposomes were made by sonicating these milky lipid suspensions to clarity, stored at 4° C., and used within a week. For both entry and internalization blocking assays, liposome preparations were diluted in appropriate medium (e.g., DMEM) containing 10% FBS and preincubated with cells for 20-30 min. at room temperature. Pseudoviruses or VLPs were then added and culture plates shifted to 37° C. for infection. Independent experiments were performed with independent liposome preparations.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

REFERENCES

The following documents are cited herein.
1. Helenius A (2007) Virus Entry and Uncoating. In: Knipe D M, Howley P M, editors. Fields Virology. 5 ed. Philadelphia, USA: Lippincott Williams & Wilkins. pp. 99-118.
2. Kaplan G, Totsuka A, Thompson P, Akatsuka T, Moritsugu Y, et al. (1996) Identification of a surface glycoprotein on African green monkey kidney cells as a receptor for hepatitis A virus. EMBO J 15: 4282-4296.
3. Silberstein E, Dveksler G, Kaplan G G (2001) Neutralization of hepatitis A virus (HAV) by an immunoadhesin containing the cysteine-rich region of HAV cellular receptor-1. J Virol 75: 717-725.
4. Feigelstock D, Thompson P, Mattoo P, Zhang Y, Kaplan G G (1998) The human homolog of HAVcr-1 codes for a hepatitis A virus cellular receptor. J Virol 72: 6621-6628.
5. Kondratowicz A S, Lennemann N J, Sinn P L, Davey R A, Hunt C L, et al. (2011) T-cell immunoglobulin and mucin domain 1 (TIM-1) is a receptor for Zaire Ebolavirus and Lake Victoria Marburgvirus. Proc Natl Acad Sci USA 108: 8426-8431.
6. Schornberg K L, Shoemaker C J, Dube D, Abshire M Y, Delos S E, et al. (2009) Alpha5beta1-integrin controls ebolavirus entry by regulating endosomal cathepsins. Proc Natl Acad Sci USA 106: 8003-8008.
7. Takada A, Watanabe S, Ito H, Okazaki K, Kida H, et al. (2000) Downregulation of beta1 integrins by Ebola virus glycoprotein: implication for virus entry. Virology 278: 20-26.
8. Simmons G, Rennekamp A J, Chai N, Vandenberghe L H, Riley J L, et al. (2003) Folate receptor alpha and caveolae are not required for Ebola virus glycoprotein-mediated viral infection. J Virol 77: 13433-13438.
9. Sinn P L, Hickey M A, Staber P D, Dylla D E, Jeffers S A, et al. (2003) Lentivirus vectors pseudotyped with filoviral envelope glycoproteins transduce airway epithelia from the apical surface independently of folate receptor alpha. J Virol 77: 5902-5910.

10. Chan S Y, Empig C J, Welte F J, Speck R F, Schmaljohn A, et al. (2001) Folate receptor-alpha is a cofactor for cellular entry by Marburg and Ebola viruses. Cell 106: 117-126.
11. Shimojima M, Takada A, Ebihara H, Neumann G, Fujioka K, et al. (2006) Tyro3 family-mediated cell entry of Ebola and Marburg viruses. J Virol 80: 10109-10116.
12. Simmons G, Reeves J D, Grogan C C, Vandenberghe L H, Baribaud F, et al. (2003) DC-SIGN and DC-SIGNR bind ebola glycoproteins and enhance infection of macrophages and endothelial cells. Virology 305: 115-123.
13. Takada A, Fujioka K, Tsuiji M, Morikawa A, Higashi N, et al. (2004) Human macrophage C-type lectin specific for galactose and N-acetylgalactosamine promotes filovirus entry. J Virol 78: 2943-2947.
14. Gramberg T, Hofmann H, Moller P, Lalor P F, Marzi A, et al. (2005) LSECtin interacts with filovirus glycoproteins and the spike protein of SARS coronavirus. Virology 340: 224-236.
15. Carette J E, Raaben M, Wong A C, Herbert A S, Obernosterer G, et al. (2011) Ebola virus entry requires the cholesterol transporter Niemann-Pick C1. Nature 477: 340-343.
16. Cote M, Misasi J, Ren T, Bruchez A, Lee K, et al. (2011) Small molecule inhibitors reveal Niemann-Pick C1 is essential for Ebola virus infection. Nature 477: 344-348.
17. Miller E H, Obernosterer G, Raaben M, Herbert A S, Deffieu M S, et al. (2012) Ebola virus entry requires the host-programmed recognition of an intracellular receptor. EMBO J 31: 1947-1960.
18. Freeman G J, Casasnovas J M, Umetsu D T, DeKruyff R H (2010) TIM genes: a family of cell surface phosphatidylserine receptors that regulate innate and adaptive immunity. Immunol Rev 235: 172-189.
19. Santiago C, Ballesteros A, Martinez-Munoz L, Mellado M, Kaplan G G, et al. (2007) Structures of T cell immunoglobulin mucin protein 4 show a metal-Ion-dependent ligand binding site where phosphatidylserine binds. Immunity 27: 941-951.
20. Kuchroo V K, Umetsu D T, DeKruyff R H, Freeman G J (2003) The TIM gene family: emerging roles in immunity and disease. Nat Rev Immunol 3: 454-462.
21. Kobayashi N, Karisola P, Pena-Cruz V, Dorfman D M, Jinushi M, et al. (2007) TIM-1 and TIM-4 glycoproteins bind phosphatidylserine and mediate uptake of apoptotic cells. Immunity 27: 927-940.
22. DeKruyff R H, Bu X, Ballesteros A, Santiago C, Chim Y L, et al. (2010) T cell/transmembrane, Ig, and mucin-3 allelic variants differentially recognize phosphatidylserine and mediate phagocytosis of apoptotic cells. J Immunol 184: 1918-1930.
23. Schlegel R A, Williamson P (2001) Phosphatidylserine, a death knell. Cell Death Differ 8: 551-563.
24. Frey B, Gaipl U S (2011) The immune functions of phosphatidylserine in membranes of dying cells and microvesicles. Semin Immunopathol 33: 497-516.
25. Ravichandran K S (2011) Beginnings of a good apoptotic meal: the find-me and eat-me signaling pathways. Immunity 35: 445-455.
26. Miyanishi M, Tada K, Koike M, Uchiyama Y, Kitamura T, et al. (2007) Identification of Tim4 as a phosphatidylserine receptor. Nature 450: 435-439.
27. Nakayama M, Akiba H, Takeda K, Kojima Y, Hashiguchi M, et al. (2009) Tim-3 mediates phagocytosis of apoptotic cells and cross-presentation. Blood 113: 3821-3830.
28. Ichimura T, Bonventre J V, Bailly V, Wei H, Hession C A, et al. (1998) Kidney injury molecule-1 (KIM-1), a putative epithelial cell adhesion molecule containing a novel immunoglobulin domain, is up-regulated in renal cells after injury. J Biol Chem 273: 4135-4142.
28. Umetsu S E, Lee W L, McIntire J J, Downey L, Sanjanwala B, et al. (2005) TIM-1 induces T cell activation and inhibits the development of peripheral tolerance. Nat Immunol 6: 447-454.
29. Zhu C, Anderson A C, Schubart A, Xiong H, Imitola J, et al. (2005) The Tim-3 ligand galectin-9 negatively regulates T helper type 1 immunity. Nat Immunol 6: 1245-1252.
30. Monney L, Sabatos C A, Gaglia J L, Ryu A, Waldner H, et al. (2002) Th1-specific cell surface protein Tim-3 regulates macrophage activation and severity of an autoimmune disease. Nature 415: 536-541.
31. Mercer J, Helenius A (2008) Vaccinia virus uses macropinocytosis and apoptotic mimicry to enter host cells. Science 320: 531-535.
32. Soares M M, King S W, Thorpe P E (2008) Targeting inside-out phosphatidylserine as a therapeutic strategy for viral diseases. Nat Med 14: 1357-1362.
33. Gautier I, Coppey J, Durieux C (2003) Early apoptosis-related changes triggered by HSV-1 in individual neuron-like cells. Exp Cell Res 289: 174-183.
34. Morizono K, Xie Y, Olafsen T, Lee B, Dasgupta A, et al. (2011) The soluble serum protein Gas6 bridges virion envelope phosphatidylserine to the TAM receptor tyrosine kinase Axl to mediate viral entry. Cell Host Microbe 9: 286-298.
35. Millard E E, Srivastava K, Traub L M, Schaffer J E, Ory D S (2000) Niemann-pick type C1 (NPC1) overexpression alters cellular cholesterol homeostasis. J Biol Chem 275: 38445-38451.
36. Li W, Zhang C, *Sui* J, Kuhn J H, Moore M J, et al. (2005) Receptor and viral determinants of SARS-coronavirus adaptation to human ACE2. EMBO J 24: 1634-1643.
37. Kuhn J H, Radoshitzky S R, Guth A C, Warfield K L, Li W, et al. (2006) Conserved receptor-binding domains of Lake Victoria marburgvirus and Zaire ebolavirus bind a common receptor. J Biol Chem 281: 15951-15958.
38. Abraham J, Kwong J A, Albarino C G, Lu J G, Radoshitzky S R, et al. (2009) Host-species transferrin receptor 1 orthologs are cellular receptors for nonpathogenic new world Glade B arenaviruses. PLoS Pathog 5: e1000358.
39. Li W, Moore M J, Vasilieva N, *Sui* J, Wong S K, et al. (2003) Angiotensin-converting enzyme 2 is a functional receptor for the SARS coronavirus. Nature 426: 450-454.
40. McKay T, Patel M, Pickles R J, Johnson L G, Olsen J C (2006) Influenza M2 envelope protein augments avian influenza hemagglutinin pseudotyping of lentiviral vectors. Gene Ther 13: 715-724.
41. Radoshitzky S R, Abraham J, Spiropoulou C F, Kuhn J H, Nguyen D, et al. (2007) Transferrin receptor 1 is a cellular receptor for New World haemorrhagic fever arenaviruses. Nature 446: 92-96.
42. Pierson T C, Sanchez M D, Puffer B A, Ahmed A A, Geiss B J, et al. (2006) A rapid and quantitative assay for measuring antibody-mediated neutralization of West Nile virus infection. Virology 346: 53-65.
43. Diamond M S, Edgil D, Roberts T G, Lu B, Harris E (2000) Infection of human cells by dengue virus is modulated by different cell types and viral strains. J Virol 74: 7814-7823.

44. Tassaneetrithep B, Burgess T H, Granelli-Piperno A, Trumpfheller C, Finke J, et al. (2003) DC-SIGN (CD209) mediates dengue virus infection of human dendritic cells. J Exp Med 197: 823-829.
45. Huang I C, Li W, Sui J, Marasco W, Choe H, et al. (2008) Influenza A virus neuraminidase limits viral superinfection. J Virol 82: 4834-4843.
45. Martinez O, Valmas C, Basler C F (2007) Ebola virus-like particle-induced activation of NF-kappaB and Erk signaling in human dendritic cells requires the glycoprotein mucin domain. Virology 364: 342-354.
46. Sherer N M, Lehmann M J, Jimenez-Soto L F, Ingmundson A, Horner S M, et al. (2003) Visualization of retroviral replication in living cells reveals budding into multivesicular bodies. Traffic 4: 785-801.
47. Flanagan M L, Oldenburg J, Reignier T, Holt N, Hamilton G A, et al. (2008) New world clade B arenaviruses can use transferrin receptor 1 (TfR1)-dependent and -independent entry pathways, and glycoproteins from human pathogenic strains are associated with the use of TfR1. J Virol 82: 938-948.
48. Helguera G, Jemielity S, Abraham J, Cordo S M, Martinez M G, etal. (2012) An antibody recognizing the apical domain of human transferrin receptor 1 efficiently inhibits the entry of all new world hemorrhagic Fever arenaviruses. J Virol 86: 4024-4028.
49. Emoto K, Toyama-Sorimachi N, Karasuyama H, Inoue K, Umeda M (1997) Exposure of phosphatidylethanolamine on the surface of apoptotic cells. Exp Cell Res 232: 430-434.
50. Licata J M, Johnson R F, Han Z, Harty R N (2004) Contribution of ebola virus glycoprotein, nucleoprotein, and VP24 to budding of VP40 virus-like particles. J Virol 78: 7344-7351.
51. Kallstrom G, Warfield K L, Swenson D L, Mort S, Panchal R G, etal. (2005) Analysis of Ebola virus and VLP release using an immunocapture assay. J Virol Methods 127: 1-9.
52. Cao W, Henry M D, Borrow P, Yamada H, Elder J H, etal. (1998) Identification of alpha-dystroglycan as a receptor for lymphocytic choriomeningitis virus and Lassa fever virus. Science 282: 2079-2081.
53. Bellosta P, Costa M, Lin D A, Basilico C (1995) The receptor tyrosine kinase ARK mediates cell aggregation by homophilic binding. Mol Cell Biol 15: 614-625.
54. Goruppi S, Ruaro E, Varnum B, Schneider C (1997) Requirement of phosphatidylinositol 3-kinase-dependent pathway and Src for Gas6-Axl mitogenic and survival activities in NIH 3T3 fibroblasts. Mol Cell Biol 17: 4442-4453.
55. Smit J M, Bittman R, Wilschut J (1999) Low-pH-dependent fusion of Sindbis virus with receptor-free cholesterol- and sphingolipid-containing liposomes. J Virol 73: 8476-8484.
56. White J, Helenius A (1980) pH-dependent fusion between the Semliki Forest virus membrane and liposomes. Proc Natl Acad Sci USA 77: 3273-3277.
57. Stegmann T, Hoekstra D, Scherphof G, Wilschut J (1985) Kinetics of pH-dependent fusion between influenza virus and liposomes. Biochemistry 24: 3107-3113.
58. Geisbert T W, Hensley L E, Larsen T, Young H A, Reed D S, et al. (2003) Pathogenesis of Ebola hemorrhagic fever in cynomolgus macaques: evidence that dendritic cells are early and sustained targets of infection. Am J Pathol 163: 2347-2370.
59. Hensley L E, Alves D A, Geisbert J B, Fritz E A, Reed C, etal. (2011) Pathogenesis of Marburg hemorrhagic fever in cynomolgus macaques. J Infect Dis 204 Suppl 3: S1021-1031.
60. Kyle J L, Beatty P R, Harris E (2007) Dengue virus infects macrophages and dendritic cells in a mouse model of infection. J Infect Dis 195: 1808-1817.
61. van den Eijnde S M, Boshart L, Baehrecke E H, De Zeeuw C I, Reutelingsperger C P, etal. (1998) Cell surface exposure of phosphatidylserine during apoptosis is phylogenetically conserved. Apoptosis 3: 9-16.
62. Fast P G (1966) A comparative study of the phospholipids and fa acids of some insects. Lipids 1: 209-215.
63. Butters T D, Hughes R C (1981) Phospholipids and glycolipids in subcellular fractions of mosquito *Aedes aegypti* cells. In Vitro 17: 831-838.
64. Ichimura T, Bonventre J V, Bailly V, Wei H, Hession C A, et al. (1998) Kidney injury molecule-1 (KIM-1), a putative epithelial cell adhesion molecule containing a novel immunoglobulin domain, is up-regulated in renal cells after injury. J Biol Chem 273: 4135-4142.
65. Huang I C, Li W, Sui J, Marasco W, Choe H, et al. (2008) Influenza A virus neuraminidase limits viral superinfection. J Virol 82: 4834-4843.
66. Tscherne D M, Manicassamy B, Garcia-Sastre A (2010) An enzymatic virus-like particle assay for sensitive detection of virus entry. J Virol Methods 163: 336-343.
67. van der Schaar H M, Rust M J, Waarts B L, van der Ende-Metselaar H, Kuhn R J, et al. (2007) Characterization of the early events in dengue virus cell entry by biochemical assays and single-virus tracking. J Virol 81: 12019-12028.
68. Meertens L, Carnec X, Lecoin M P, Ramdasi R, Guivel-Benhassine F, et al. (2012) The TIM and TAM Families of Phosphatidylserine Receptors Mediate Dengue Virus Entry. Cell Host Microbe 12: 544-557.

What is claimed is:

1. A method for inhibiting viral entry of an enveloped virus to a cell, comprising contacting the cell with an effective amount of an agent that inhibits viral entry via a T-cell Immunoglobulin and Mucin-domain containing protein 1 (TIM-1), TIM3, TIM4 or phosphatidylserine (PS) receptor, wherein the agent consists of an inhibitory nucleic acid molecule or an antibody or fragment thereof, 1,2-diacyl-sn-glycero-3-phospho-L-serine (PS), 1,2-diacyl-sn-glycero-3-phosphoethanolamine (PE) and a liposome consisting of 1, 2-diacyl-sn-glycero-3-phospho-L-serine (PS) and 1,2-diacyl-sn-glycero-3-phosphocholine (PC), wherein the enveloped virus is an alphavirus, flavivirus, filovirus, or arenavirus.

2. The method of claim 1, wherein the inhibitory nucleic acid molecule is selected from the group consisting of an antisense molecule, an siRNA, and an shRNA.

3. The method of claim 1, wherein the antibody or fragment thereof that selectively binds to the TIM-1, TIM3 or TIM4.

4. The method of claim 3, wherein the antibody is a monoclonal or polyclonal antibody.

5. The method of claim 1, wherein the agent reduces viral entry by at least 60%, 65%, 70%, 75%, 80%, 85%, 90%, 95%, 96%, 97%, 98%, 99%, or 100%.

6. The method of claim 1, wherein the agent protects the cell from lethality.

7. The method of claim 1, wherein the virus is selected from the group consisting of Ebola virus (EBOV), Marburg virus (MARY), Amapari virus (AMAV), Tacaribe virus (TCRV), Junin virus (JUNV), Machupo virus (MACV), Chikungunya virus (CHKV), Eastern equine encephalitis virus (EEEV), Dengue virus (DENV), West Nile virus (WNV), Sinbis virus (SINN) or Ross River virus (RRV).

* * * * *